US011744470B2

(12) United States Patent
Hui et al.

(10) Patent No.: US 11,744,470 B2
(45) Date of Patent: Sep. 5, 2023

(54) METHODS AND SYSTEMS FOR ELECTROMAGNETIC NEAR-FIELD COHERENT SENSING

(71) Applicant: Cornell University, Ithaca, NY (US)

(72) Inventors: Xiaonan Hui, Ithaca, NY (US); Edwin C. Kan, Ithaca, NY (US)

(73) Assignee: Cornell University, Ithaca, NY (US)

( * ) Notice: Subject to any disclaimer, the term of this patent is extended or adjusted under 35 U.S.C. 154(b) by 566 days.

(21) Appl. No.: 16/623,141

(22) PCT Filed: Jun. 18, 2018

(86) PCT No.: PCT/US2018/038121
§ 371 (c)(1),
(2) Date: Dec. 16, 2019

(87) PCT Pub. No.: WO2018/232414
PCT Pub. Date: Dec. 20, 2018

(65) Prior Publication Data
US 2020/0170514 A1    Jun. 4, 2020

Related U.S. Application Data

(60) Provisional application No. 62/618,352, filed on Jan. 17, 2018, provisional application No. 62/521,163, filed on Jun. 16, 2017.

(51) Int. Cl.
*A61B 5/0205* (2006.01)
*A61B 5/00* (2006.01)
(Continued)

(52) U.S. Cl.
CPC .......... *A61B 5/0205* (2013.01); *A61B 5/0015* (2013.01); *A61B 5/0026* (2013.01);
(Continued)

(58) Field of Classification Search
CPC .......... G06F 21/31; G06F 1/16; H01Q 1/273; H01Q 1/2208; A61B 2562/08; A61B 5/00; A61B 5/0004; A61B 5/0015
See application file for complete search history.

(56) References Cited

U.S. PATENT DOCUMENTS 5,640,683 A   6/1997  Gifford et al.
5,777,561 A   7/1998  Chieu et al.
(Continued)

FOREIGN PATENT DOCUMENTS

CN   103198283 A   7/2013
CN   102307518 B   11/2015
(Continued)

OTHER PUBLICATIONS

Hui, X. and Kan, E.C., Monitoring vital signs over multiplexed radio by near-field coherent sensing, Nature Electronics, Nov. 27, 2017, vol. 1, pp. 74-78.
(Continued)

*Primary Examiner* — Deborah L Malamud
(74) *Attorney, Agent, or Firm* — Barnes & Thornburg LLP

(57) ABSTRACT

The present disclosure may be embodied as methods and/or systems for non-contact measuring of an on-body and/or inside-body motion of an individual. A sensing signal is provided within a near-field coupling range of a motion to be measured. In this way, a measurement signal may be generated as the sensing signal modulated by the motion. The sensing signal may be an ID-modulated signal. In some embodiments, the sensing signal is a backscattered RFID link provided a wireless tag. A downlink signal may be provided to power the wireless tag. The sensing signal may be a harmonic of the downlink signal. The measurement signal is detected. The motion is measured based on the measurement signal. The measurement signal may be
(Continued)

detected as far-field radiation after transmission through a source of the motion. The measurement signal may be detected as reflected from a source of the motion as antenna reflection.

20 Claims, 42 Drawing Sheets

(51) Int. Cl.
 *A61B 5/0507* (2021.01)
 *A61B 5/11* (2006.01)
 *H04B 5/00* (2006.01)
(52) U.S. Cl.
 CPC .......... *A61B 5/0507* (2013.01); *A61B 5/1126* (2013.01); *H04B 5/0062* (2013.01)

(56) References Cited

U.S. PATENT DOCUMENTS

| | | | |
|---|---|---|---|
| 5,873,025 A | 2/1999 | Gifford et al. |
| 5,935,077 A | 8/1999 | Ogle |
| 5,952,922 A | 9/1999 | Shober |
| 6,650,230 B1 | 11/2003 | Gifford et al. |
| 7,096,133 B1 | 8/2006 | Martin et al. |
| 7,603,894 B2 | 10/2009 | Breed |
| 7,693,626 B2 | 4/2010 | Breed et al. |
| 7,938,013 B2 | 5/2011 | Hughes et al. |
| 3,024,084 A1 | 9/2011 | Breed |
| 8,267,325 B2 | 9/2012 | Phaneuf |
| 8,286,887 B2 | 10/2012 | Wilkinson |
| 8,665,098 B2 | 3/2014 | Jau et al. |
| 8,721,559 B2 | 5/2014 | Peterson et al. |
| 8,989,867 B2 | 3/2015 | Chow et al. |
| 9,314,648 B2 | 4/2016 | Li et al. |
| 9,330,561 B2 | 5/2016 | Proud |
| 9,443,358 B2 | 9/2016 | Breed |
| 9,477,812 B2 | 10/2016 | Lin et al. |
| 9,489,813 B1 | 11/2016 | Beigel |
| 9,645,234 B2 | 5/2017 | Khan et al. |
| 9,744,369 B2 | 8/2017 | Poon et al. |
| 9,949,691 B2 | 4/2018 | Huppert et al. |
| 10,863,313 B2 | 12/2020 | Markhovsky et al. |
| 2003/0139691 A1 | 7/2003 | Kumar et al. |
| 2004/0032363 A1 | 2/2004 | Schantz et al. |
| 2005/0190098 A1 | 9/2005 | Bridgelall et al. |
| 2005/0206555 A1 | 9/2005 | Bridgelall et al. |
| 2006/0012476 A1 | 1/2006 | Markhovsky |
| 2006/0022800 A1 | 2/2006 | Krishna et al. |
| 2006/0224048 A1 | 10/2006 | Devaul et al. |
| 2006/0284727 A1 | 12/2006 | Steinke |
| 2007/0222560 A1 | 9/2007 | Posamentier |
| 2007/0279194 A1 | 12/2007 | Carrender et al. |
| 2008/0030244 A1 | 2/2008 | Leifso |
| 2008/0299933 A1 | 12/2008 | Chang et al. |
| 2009/0167699 A1 | 7/2009 | Rosenblatt et al. |
| 2010/0039228 A1 | 2/2010 | Sadr et al. |
| 2010/0060424 A1 | 3/2010 | Wild et al. |
| 2010/0152600 A1 | 6/2010 | Droitcour et al. |
| 2010/0201492 A1 | 8/2010 | Koo et al. |
| 2010/0214065 A1 | 8/2010 | Maltseff et al. |
| 2010/0292568 A1 | 11/2010 | Droitcour et al. |
| 2011/0012713 A1 | 1/2011 | Wilkinson |
| 2011/0028854 A1 | 2/2011 | Addison et al. |
| 2011/0148710 A1 | 6/2011 | Smid et al. |
| 2011/0187600 A1 | 8/2011 | Landt |
| 2012/0235689 A1 | 9/2012 | Jau et al. |
| 2012/0235856 A1 | 9/2012 | Nogami et al. |
| 2012/0249302 A1 | 10/2012 | Szu |
| 2012/0256730 A1 | 10/2012 | Scott et al. |
| 2013/0030257 A1 | 1/2013 | Nakata et al. |
| 2013/0030259 A1 | 1/2013 | Thomsen et al. |
| 2013/0043981 A1 | 2/2013 | Wang et al. |
| 2013/0165770 A1 | 6/2013 | Li et al. |
| 2013/0237798 A1* | 9/2013 | Pal ........................ A61B 5/1102 600/407 |
| 2013/0289379 A1 | 10/2013 | Song et al. |
| 2014/0292491 A1 | 10/2014 | Maltseff et al. |
| 2014/0330540 A1 | 11/2014 | Lin et al. |
| 2015/0198708 A1 | 7/2015 | Khan et al. |
| 2015/0282711 A1 | 10/2015 | Thomas et al. |
| 2016/0143557 A1 | 5/2016 | Kahlman et al. |
| 2016/0166160 A1 | 6/2016 | Casale |
| 2016/0338798 A1 | 11/2016 | Vora et al. |
| 2017/0055872 A1 | 3/2017 | Tupin, Jr. |
| 2017/0065184 A1 | 3/2017 | Barak |
| 2017/0082741 A1 | 3/2017 | Adib et al. |
| 2017/0108452 A1 | 4/2017 | Carlson |
| 2017/0367619 A1 | 12/2017 | Zhan |
| 2019/0261137 A1 | 8/2019 | Markhovsky et al. |

FOREIGN PATENT DOCUMENTS

| | | |
|---|---|---|
| CN | 106102566 A | 11/2016 |
| EP | 0853392 A2 | 7/1998 |
| EP | 0670558 B1 | 5/2000 |
| EP | 1744267 A2 | 1/2007 |
| WO | 2016065368 A1 | 4/2016 |
| WO | 2017/093391 A1 | 6/2017 |
| WO | 2017/153907 A1 | 9/2017 |
| WO | 2018/011697 A1 | 1/2018 |

OTHER PUBLICATIONS

Saccone, L., Near-Field Coherent Sensing Used to Monitor Vital Signs, Engineering News, Nov. 30, 2017, 4 pages.
Taiwan Office Action for Application No. 107121019, dated May 17, 2022, 15 pages.
Taiwan Office Action for Application No. 107121019, dated Jun. 26, 2023, 16 pages.

* cited by examiner

METHODS AND SYSTEMS FOR ELECTROMAGNETIC NEAR-FIELD COHERENT SENSING

CROSS-REFERENCE TO RELATED APPLICATIONS

This application claims priority to U.S. Provisional Application No. 62/521,163, filed on Jun. 16, 2017, now pending, and 62/618,352, filed on Jan. 17, 2018, now pending, the disclosures of which are incorporated herein by reference.

STATEMENT REGARDING FEDERALLY SPONSORED RESEARCH

This invention was made with government support under contract no. DE-AR0000528 awarded by the Department of Energy. The government has certain rights in the invention.

FIELD OF THE DISCLOSURE

The present disclosure relates to detection of motion, and in particular, detecting vital signs without a need for physical contact.

BACKGROUND OF THE DISCLOSURE

The monitoring of vital signs, such as, for example, heart rate, blood pressure, respiration rate, and breath effort is a critical procedure for patient management and pathological recording. Current practices based on body electrodes, optical absorption, pressure or strain gauge, and ultrasound or radio frequency (RF) backscattering have respective limitations on the sensing capabilities and sampling rates. The measurement process can also be uncomfortable due to direct skin contact or motion restriction for the individual under test, or disruptive to the individual's circadian rhythm. This inconvenience adds significant work load to care givers and discourages continuous long-term monitoring.

Due to the strong reflection of the body surface and the geometric average of the reflected signal, conventional techniques for radio frequency ("RF")-based far-field vital signal detection can pick up breath motion readily, but these techniques have difficulty distinguishing the small mechanical vibration details such as the heartbeat and wrist-pulse waveforms with low RF frequency. Although the heart rate can be retrieved after careful filtering, estimation of blood pressure and simultaneous monitoring of multiple free-moving people remain unachievable.

There remains a long-felt need for less invasive techniques for detecting vital signs.

BRIEF SUMMARY OF THE DISCLOSURE

A method of RF near-field coherent sensing (NCS), without immediate skin contact, is provided. The present method may be used to directly modulate the real-time mechanical motion on and/or inside the body onto a multiplexed radio, which may contain a unique identification (ID). Two exemplary embodiments are described herein to offer flexibility in deployment and operation: passive and active tags in the vicinities of the heart and wrist. To reduce deployment and maintenance cost, passive RFID tags can be integrated into garments at the chest and wrist areas, where two multiplexed far-field backscattering waveforms may be collected at the reader to retrieve the heart rate, the respiration rate, the breath effort, and the blood pressure. To improve reading range and immunity to indoor motion, active tags can be placed in, for example, a front pocket and in a wrist cuff to measure the antenna reflection due to NCS, and then the vital signals may be sampled and transmitted entirely in digital format to negate the indoor multi-path interference. The presently-disclosed vital sign monitoring system may be used for multiple individuals simultaneously, and can bring forth cost-effective automation in care facilities. Furthermore, the elimination of direct skin contact and motion restriction will enhance comfort to patients, which can enable long-term monitoring for improved pathological analyses.

Through an implementation of NCS using an exemplary harmonic RFID system for vital-sign monitoring, breath, heartbeat, and wrist pulse can be monitored to derive the breath rates, heart rates, and blood pressure. In some embodiments, spectral equalization may be applied to NCS signals to recover accurate heartbeat intervals in time domain.

Sensing antenna impedance matching effects are shown for NCS, wherein a tissue-matched antenna is shown to provide improved NCS signal quality and waveform details. The performance of the vital-sign waveform retrieval was analyzed and the design strategy was discussed.

In another embodiment, the high-frequency components of a heartbeat signal may be used to mitigate body movement interference on heart rate estimate. By benchmark against ECG, NCS was shown to be sufficiently accurate for real-time heartrate and heartrate variability with normal body motion.

In another aspect, the present disclosure may be embodied as a method for non-contact measuring of an on-body and/or inside-body motion of an individual. A first radiofrequency ("RF") sensing signal is provided within a near-field coupling range of a first motion to be measured. In this way, a first measurement signal may be generated as the first sensing signal modulated by the first motion. The first sensing signal may be an ID-modulated signal. The first sensing signal may be an active radio link. The first sensing signal may be a backscattered RFID link. The first sensing signal may be provided by a wireless tag. A downlink signal may be provided to power the wireless tag. The first sensing signal may be a harmonic of the downlink signal.

The first measurement signal is detected. The first motion is measured based on the first measurement signal. The first measurement signal may be detected as far-field radiation after transmission through a source of the first motion. The first measurement signal may be detected as reflected from a source of the first motion as antenna reflection. Measuring the first motion further may further comprises filtering the first measurement signal to obtain a first motion signal through timing and waveforms.

In some embodiments, the method further includes providing a second RF sensing signal within a near-field coupling range of a second motion to be measured. In this way, a second measurement signal may be generated as the second sensing signal modulated by the second motion. The second measurement signal is detected. The second motion is measured based on the second measurement signal. A derivative value may be measured based on the synchronized measured first motion and second motion.

In another aspect, a system is provided for measuring motion of an individual. The system includes a first signal source for generating a first sensing signal. A first antenna is in electrical communication with the first signal source. The first sensing signal may be an ID-modulated wave. The first sensing signal may be an active radio link. The first sensing signal may be a backscattered RFID link. The first antenna is configured to be disposed within a near-field coupling range of a first motion to be measured. The first antenna may be configured to be disposed within a coupling range of a heart motion, a pulse, a respiration motion, a bowel motion, an eye motion, etc. In this way, a first measurement signal is generated as the first sensing signal modulated by the first motion. The system includes a first receiver for detecting a first measurement signal. The first receiver may be configured to detect the first measurement signal as a transmitted signal. The first receiver may be configured to detect the first measurement signal as a reflected signal.

The first signal source and first antenna may be configured as a wireless tag. A tag reader is configured to transmit a downlink signal to the wireless tag. The receiver may be a part of the tag reader. The wireless tag may be configured to be powered by the downlink signal. The first sensing signal may have a frequency which is a harmonic of a frequency of the downlink signal. For example, the first sensing signal may be a second harmonic of the downlink signal. The wireless tag may modulate the downlink signal with an orthogonal ID, such that the first sensing signal is a CDMA signal.

In some embodiments, the system may further include a second signal source for generating a second sensing signal. A second antenna is in electrical communication with the second signal source. The second antenna is configured to be disposed within a near-field coupling range of a second motion to be measured to generate a second measurement signal as the second sensing signal modulated by the second motion. The receiver may be further configured to detect the second measurement signal.

In some embodiments, a filter is in communication with the receiver. The filter may be configured to demodulate and filter the first and/or second measurement signal to obtain a corresponding first and/or second motion signal. The filter may be, for example, a processor programmed to sample, demodulate, and filter the first and/or second measurement signal to derive motion. In some embodiments, a processor is programmed to measure a derivative value based on the detected coupled signal and second coupled signal.

DESCRIPTION OF THE DRAWINGS

For a fuller understanding of the nature and objects of the disclosure, reference should be made to the following detailed description taken in conjunction with the accompanying drawings, in which.

DETAILED DESCRIPTION OF THE DISCLOSURE

Vital signs are not only important for pathological studies, but also widely referenced by wearable devices to infer behavior, emotion, and wellness. Although many of these devices are well established and widely applied, the current devices have drawbacks that that limit their sensing accuracy or long-term convenience. The present disclosure may be embodied as a method for near-field coherent sensing ("NCS"), which modulates the movement of an individual onto radio frequency ("RF") signals, which can be multiplexed RF signals. Movements of an individual may include, for example, movements related to vital signs—e.g., heartbeat, pulse, breathing, etc. Embodiments of the present method may directly modulate mechanical motion on the body surface or inside the body of the individual onto RF signals in the near-field range. The motion can be modulated onto multiplexed harmonic RF Identification ("RFID") backscattering signals with unique digital identification ("ID").

The "near field" of an antenna is a region where induction characteristics dominate over radiation characteristics and the relationship between the electric field (E field) and the magnetic field (H field) is not well defined. In embodiments of the present disclosure, "near-field" may refer to the close-in region of an antenna where angular field distribution is dependent upon the distance from the antenna. In embodiments, the near-field extends to the region within one wavelength ($\lambda$) of the antenna. In other embodiments, the near-field extends to the region within $\lambda/2$, $\lambda/3$, $\lambda/4$, or $\lambda/2\pi$ of the antenna, where $\lambda$ is the operating wavelength of the antenna. Other embodiments will be apparent to one having skill in the art with the benefit of the present disclosure.

Figure 21:
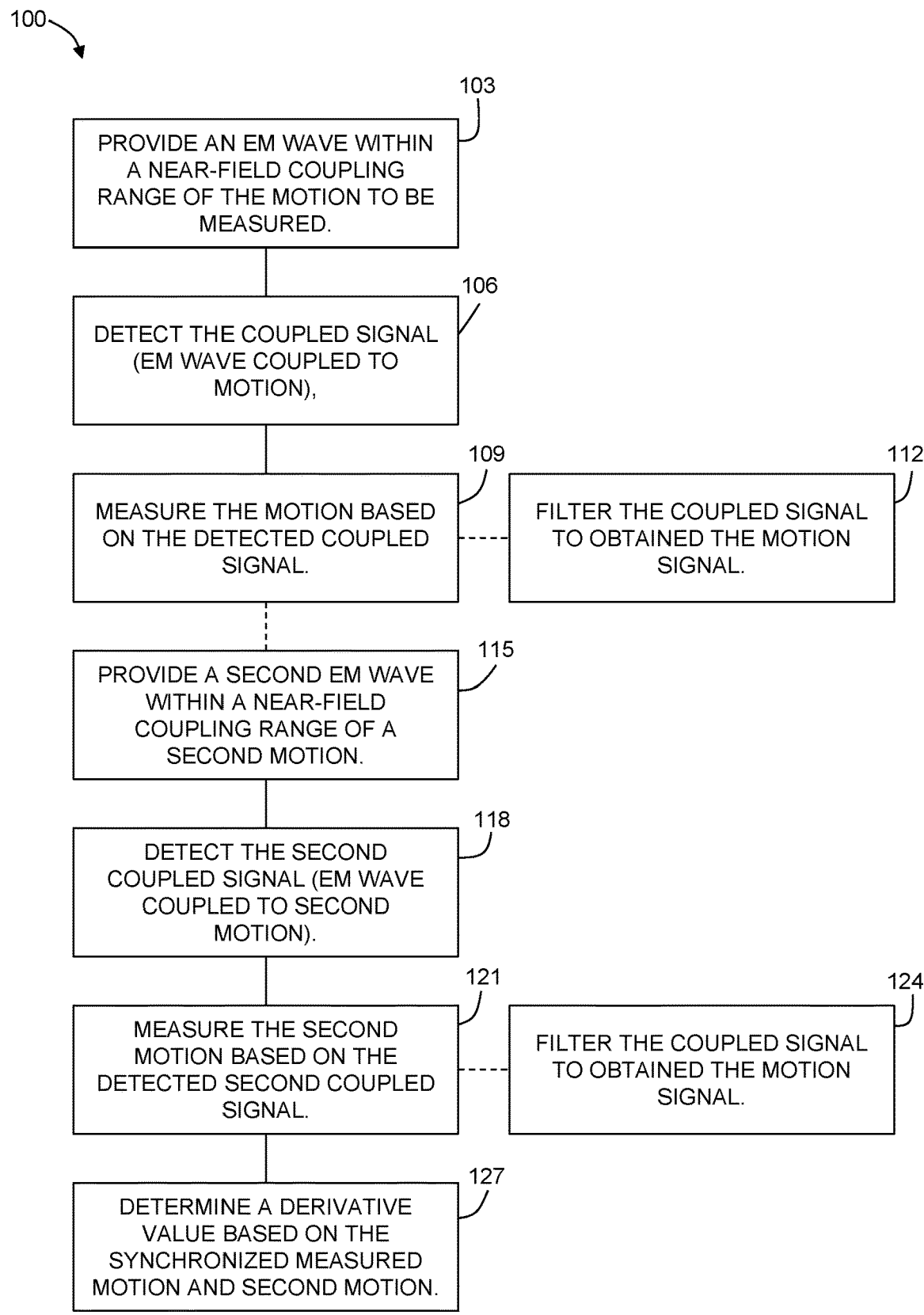
FIG. 21 is a flowchart showing a method according to another embodiment of the present disclosure.

With reference to FIG. 21, the present disclosure may be embodied as a method 100 for non-contact measuring of a body motion of an individual (e.g., on-body or inside-body motion). The individual may be, for example, a human or a non-human animal. The detected motion may be, for example, a heart motion, a pulse, a respiration motion, a bowel motion, an eye motion, or other body motion as will be apparent in light of the present disclosure. Embodiments of the present method 100 may directly modulate the mechanical motion on the body surface or inside the body of the individual onto multiplexed radio signals integrated with a unique digital ID. A first radiofrequency ("RF") sensing signal is provided 103 within a near-field coupling range of a first motion to be measured to generate a measurement signal. The provided 103 first sensing signal may be an ID-modulated signal. In some embodiments, the first sensing signal is an active radio link. In some embodiments, the first sensing signal is a backscattered RFID link. For example, an antenna may emit a beacon or ID-modulated sensing signal in either an active radio link or a backscattering RFID (radio identification) link. The first sensing signal will be modulated by the first motion thereby generating a first measurement signal. The method 100 includes detecting 106 the first measurement signal. In some embodiments, the detection 106 may be done at the far field, for example, detecting the first measurement signal transmitted through the body of the individual. In some embodiments, the detection 106 is of a reflected signal, for example, using the near-field antenna.

The first motion is measured 109 based on the first measurement signal. As mentioned above, in NCS, more energy is directed into the body tissue than previous techniques, so the backscattered signal from internal organs is implicitly amplified. Also, shorter wavelengths within the body tissues render a small mechanical motion into a relatively large phase variation. Shorter wavelengths within the body of the individual naturally increase the signal-to-noise ratio ("SNR"). The differential nature of in-body signals can isolate large surface movements. This can also increase sensitivity, enabling the measurement of a weak motion signal such as, for example, a wrist pulse. Because the internal mechanical motion modulation gives a differential signal similar to an interferometer, the common signal caused by external movement can be readily depressed by filtering (see, e.g., FIG. 2A). With an antenna within the near-field coupling range of the mechanical motion inside the body, the propagating or reflected wave can be readily detected in a coherent manner and will contain the real-time geometry-average information of the mechanical motion. The motion may be measured by filtering 112 the first measurement signal to obtain a motion signal. In the case of ID-modulated wave, we can read multiple mechanical motions simultaneously in a synchronized manner. Multiplexing techniques can be used in passive backscattering or active radio transmission to facilitate simultaneous sensing at multiple points and/or for multiple persons. NCS opens up new opportunities for vital signal monitoring with comfort, convenience, and low cost.

Note that the presently-disclosed NCS techniques directly measures mechanical motion inside or on a body, instead of indirectly by, for example, sensing the electrical nerve signal that induced the mechanical motion or the electrical signal induced by the mechanical motion. Hence, the present NCS technique can provide richer information than a conventional electrocardiogram. For example, by using a second tag on the wrist or neck area where a pulse can be felt, the waveform difference from a heart tag can be used to obtain an accurate estimate of the blood pressure, and this can be done multiple people within a room without ambiguity. Using the present techniques, a clinical area can be managed in a totally new way: all people wearing tag(s) according to the present disclosure can be monitored with their ID, location, heart rate, respiration rate, blood pressure, and so on. Additionally, long-term monitoring of an individual can be accomplished, because no skin contact is required (compared to, for example, ECG pad(s)).

In some embodiments, the method 100 may further include providing 115 a second RF sensing signal within a near-field coupling range of a second motion to be measured. In this way, the second motion is coupled to the second RF sensing signal to generate a second measurement signal. The second measurement signal is detected 118, and the second motion is measured 121 based on the second measurement signal. The second motion may be measured by filtering 124 the second measurement signal to obtain a second motion signal. A derivative value may be determined 127 based on the synchronized measured motion and second motion. For example, where the first motion is a heartbeat (measured near the chest) and the second motion is a pulse (measured near the wrist), the derivative value may be a blood pressure determined 127 based on the heartbeat and the pulse.

Figure 40:
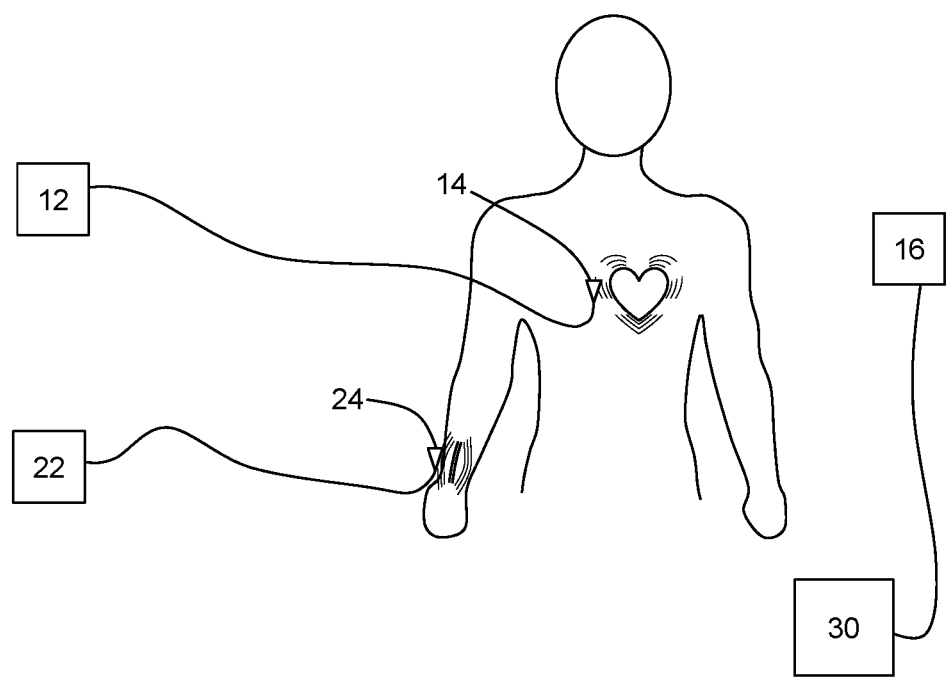
FIG. 40 is a diagram depicting a system according to another embodiment of the present disclosure.

In another aspect, the present disclosure may be embodied as a system 10 for measuring motion of an individual (see, for example, FIG. 40). The system 10 includes a first signal source 12 for generating a first sensing signal. A first antenna 14 is in electrical communication with the first signal source 12. The first antenna 14 is configured to be disposed within a near-field coupling range of a first motion to be measured. For example, the first antenna 14 may be configured to be disposed within a coupling range of a heart motion, a pulse, a respiration motion, a bowel motion, an eye motion, etc. In this way, a first measurement signal is generated by the first sensing signal modulated by the first motion. The first sensing signal may be an ID-modulated wave. For example, the EM wave may be an active radio link or a backscattering RFID link.

The system includes a receiver 16 for detecting the first measurement signal (the first sensing signal coupled with (modulated by) the first motion). The receiver 16 may be configured to detect the first measurement signal as a transmitted signal—i.e., far-field radiation. The receiver may be configured to detect the first measurement signal as a reflected signal—i.e., antenna reflection. The system may include a filter in communication with the receiver, wherein the filter is configured to demodulate and filter the first measurement signal to obtain a motion signal. The filter may be, for example, a processor (such as a digital-signal processor ("DSP")) programmed to sample, demodulate, and/or filter the first measurement signal to derive the motion signal.

In some embodiments, a system 10 may include a second signal source 22 for generating a second sensing signal. In such embodiments, a second antenna 24 is in electrical communication with the second signal source 22. The second antenna 24 is configured to be disposed within a near-field coupling range of a second motion to be measured. In this way, a second measurement signal may be generated as the second sensing signal modulated by the second motion. In a particular example, the first motion is a heartbeat and the second motion is a pulse. In such an example, the first antenna may be configured to be disposed proximal to the chest of an individual, and the second antenna may be configured to be disposed proximal to the wrist of the individual. The receiver 16 is further configured to detect the second measurement signal. The system 10 may include a processor 30 for measuring a derivative value based on the detected first measurement signal and second measurement signal. In the particular example of a heartbeat and pulse, the derivative value may be, for example, a blood pressure of the individual.

In some embodiments, wireless tags, such as passive (i.e., having no local power source such as a battery) RFID tags, may be integrated into garments near areas where vital signs are to be measured. Such RFID tags may provide for an NCS implementation with low deployment and maintenance costs. Such RFID tags may provide ID-modulated signals where a unique ID of each tag helps discriminate its signal against interference from other tags and ambient signals. The tag backscattering signal is then processed with spectral equalization to amplify the high frequency components to recover not only the waveform details originally submerged in the low-frequency components but also the sharp peaks for precise heartbeat intervals with improved peak detection certainty. The derived heartbeat interval shows improved stability in comparison with synchronous ECG.

Principle of Operation

Figure 1A:
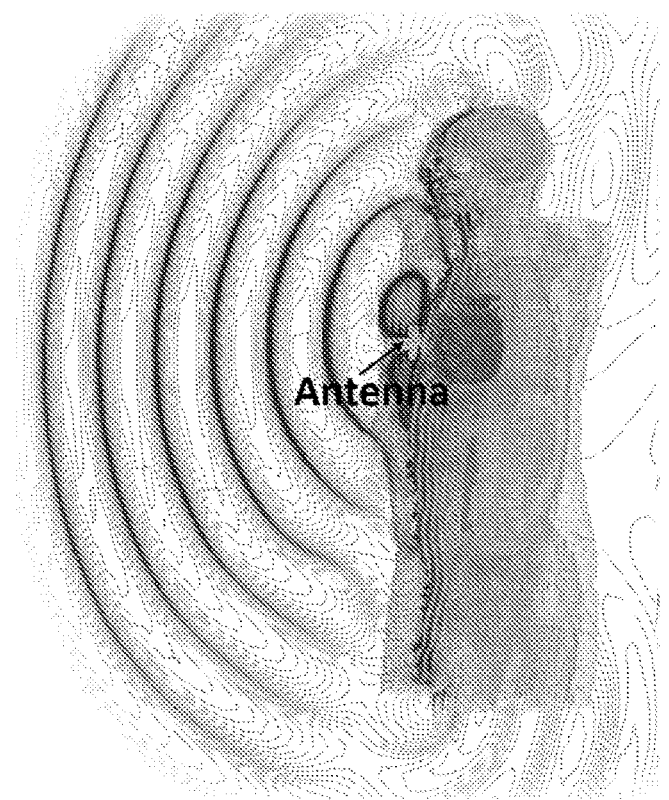
FIG. 1A depicts a CST Microwave Studio simulation model for vital signs over radio transmission by Near-field Coherent Sensing (NCS), wherein the patterns show the real part of the co-polarization electric field in a torso simulation model for heartbeat sensing.
Figure 1B:
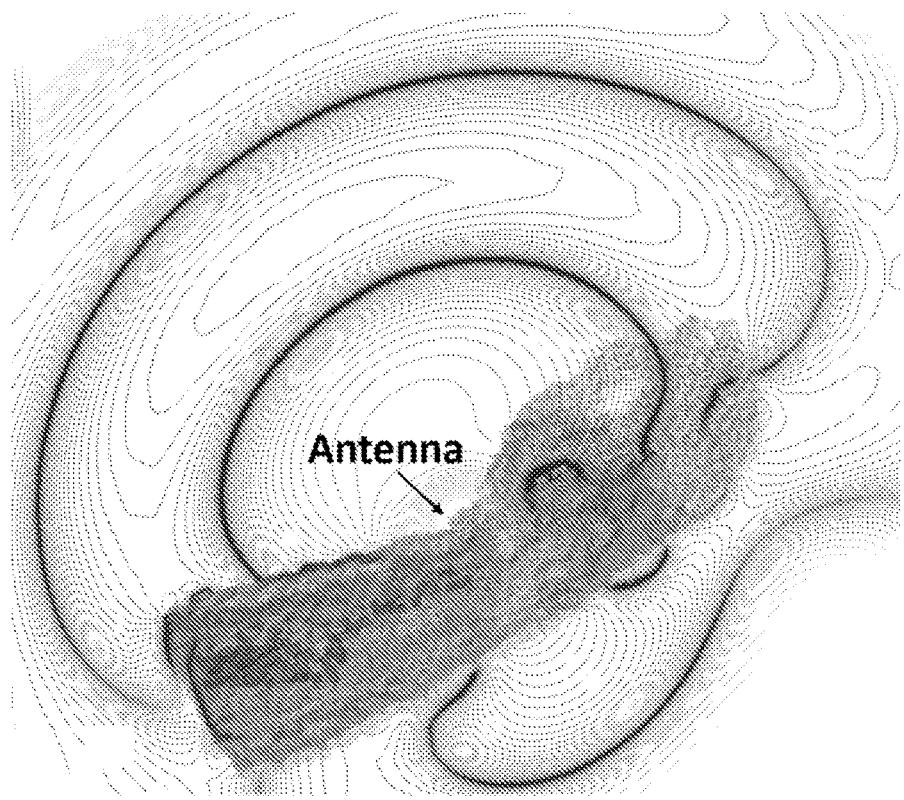
FIG. 1B depicts a CST Microwave Studio simulation model for vital signs over radio transmission by NCS, wherein the patterns show the real part of the co-polarization electric field in a wrist simulation model for pulse sensing.

Embodiments of NCS utilize near-field coupling of an EM field to the mechanical motion inside or on the surface of a body. The principle of operation of NCS was illustrated using CST Microwave Studio for electromagnetic simulation. As shown in FIGS. 1A and 1B, EM simulations of a male torso (1A) and a lower left arm (1B) were constructed. The EM simulation models were constructed based on the Zubal Phantom, which has the voxel resolution at 3.6×3.6× 3.6 $mm^3$ and was established by the magnetic resonance imaging ("MRI") and computed tomography ("CT"). Each voxel was denoted by the 3D coordinates together with the index of the human tissue. After CST imports the torso model, Visual Basic for Applications ("VBA") macro language was used to map the EM properties with the CST bio-library. The finite integration technique ("FIT") was then employed to include the RFID tag antenna near the chest area. As can be seen from the simulation, a large amount of RF energy is coupled inside the torso due to the near-field coupling. Because of the high dielectric constant of the human tissue, the wave length is much shorter correspondingly, which further increases the NCS sensitivity.

The present NCS method uses both the amplitude and phase of the electromagnetic field. Because the phase is very sensitive to the distance between the RF source and receiver, the external chest movement when a person breathes can be evaluated accordingly by the phase. The respiration rate can be easily retrieved and the respiration effort can be further interpreted with the phase variation. In comparison with the phase information, the amplitude of the electromagnetic field is not so sensitive to the small distance variation, which means the breath or other external body movement will change the phase but not the amplitude as much, providing good isolation for other signals inside the body to be properly sensed. In NCS, the interferometry-like structure transduces the internal organs/tissues movement into amplitude modulation of the RF signal.

For our simulations (FIG. 2A), when the human phantom faces the receiver (FIG. 4A), the on-chest antenna emits the RF carrier with the antenna characteristics defined by the local near-field region. According to the antenna directivity, part of the RF energy will be directly emitted towards the receiver, while the other part will be coupled inside the body due to the near-field effect. Intuitively, we can consider that the backscattered RF signal from the heart is modulated by the mechanical movement of the heart tissue and then interferes with the direct emission, resulting in amplitude changes. From the interferometer analogy, the movement inside the body is a 'differential-mode' modulation, while the body surface movement is a 'common-mode' modulation.

Figure 3A:
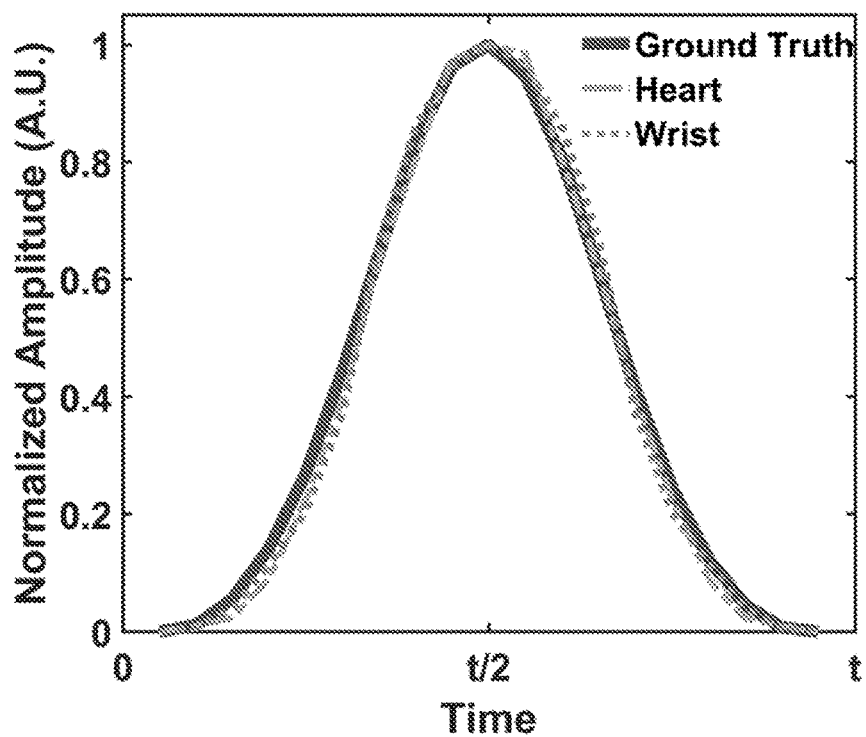
FIG. 3A shows a graph wherein the simulated vibration amplitudes of FIGS. 1A and 1B are compared with sampling at the far-field points.
Figure 3B:
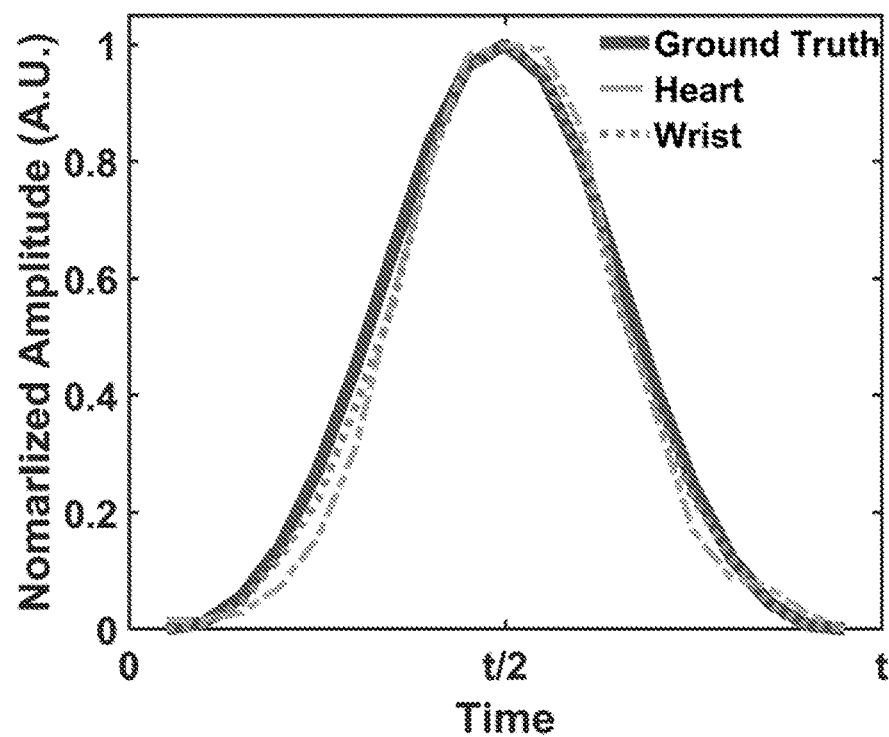
FIG. 3B shows a graph wherein the simulated vibration amplitudes of FIGS. 1A and 1B are compared with sampling at the antenna reflection represented by the scattering parameter $S_{11}$.

The motion can be recorded not only from the far field, but also from the antenna reflection shown as the scattering parameter $S_{11}$ in FIG. 3B. Using antenna reflection, an NCS signal can be directly recorded using a mobile device and is thus more immune to body movement and indoor multipath issues in a crowded room. Because NCS operates with the tissue motion within the near-field region of the antenna, the geometric variation will affect antenna reflection $S_{11}$, where the antenna can be regarded as a part of the sensor. The vital signs will be modulated on the antenna's $S_{11}$ parameter and retrieved by the reflected signal accordingly.

Figure 5A:
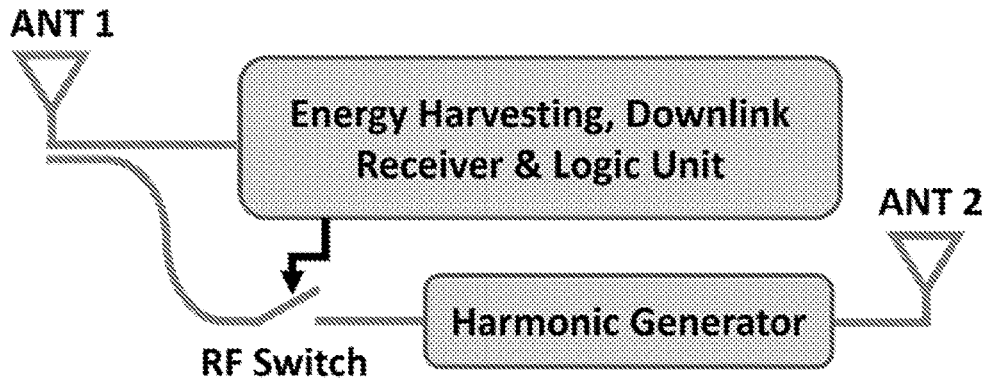
FIG. 5A is a diagram of a passive harmonic RFID tag for near-field coherent sensing according to an embodiment of the present disclosure.
Figure 8A:
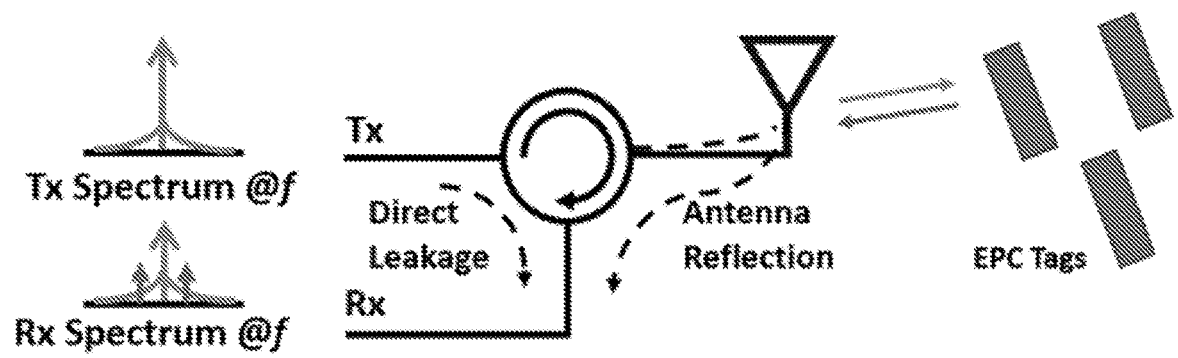
FIG. 8A is a diagram of a conventional RFID system showing the RF front end of the RFID reader interacting with the tags by backscattering.

With the transmitting antenna close to the skin, an NCS device can modulate the motion signal (vital sign) over a radio signal. However, conventional microwave transmitters consume significant power in the local oscillator and power amplifier, and such transmitters may require a battery for the mobile device. In addition, synchronization between the on-body transmitter and the far-field receiver will also make the system design more complex. In some embodiments, NCS can be implemented with passive harmonic RF identification (RFID) tags, where the vital signals are modulated on the harmonic backscattering together with the tag ID. Besides the ultralow cost, the simple and robust packaging of the passive tag enables direct fabric integration with laundry readiness. An example of the RFID sensor tag chip integrated with an embroidered antenna on fabric is shown in FIG. 9A. The benefits of harmonic backscattering over the conventional RFID are summarized in FIGS. 8A and 8B. Because of the high transmitting power of the conventional RFID reader and the phase noise skirt, the self-leakage, antenna reflection and the backscattering from unintended ambient objects all contribute to the noise and heavily degrade the SNR of the backscattered tag signal. However, the harmonic backscattering can isolate the downlink (reader-to-tag) and uplink (tag-to-reader) with a large frequency separation, which increases both the SNR and sensitivity. The tag remains a passive backscatterer, which can easily comply with current RF protocols. A schematic of the harmonic tag is shown in FIG. 5A (for a photograph of the printed circuit board (PCB) prototype see FIG. 9B). The harmonic tag receives the downlink RF signal at f from the reader, which goes through the tag Antenna 1 (ANT 1) and splits into two parts. One provides D.C. power for the tag circuits by energy harvesting, and the other is fed into passive harmonic generation at 2f to be re-emitted from Antenna 2 (ANT 2), which serves as the NCS transmitter. The RF switch in front of the harmonic generator can modulate digital information by on-off keying (OOK), similar to conventional RFID operations. The digital information can include the tag ID as well as additional information from the on-tag sensors.

Figure 5B:
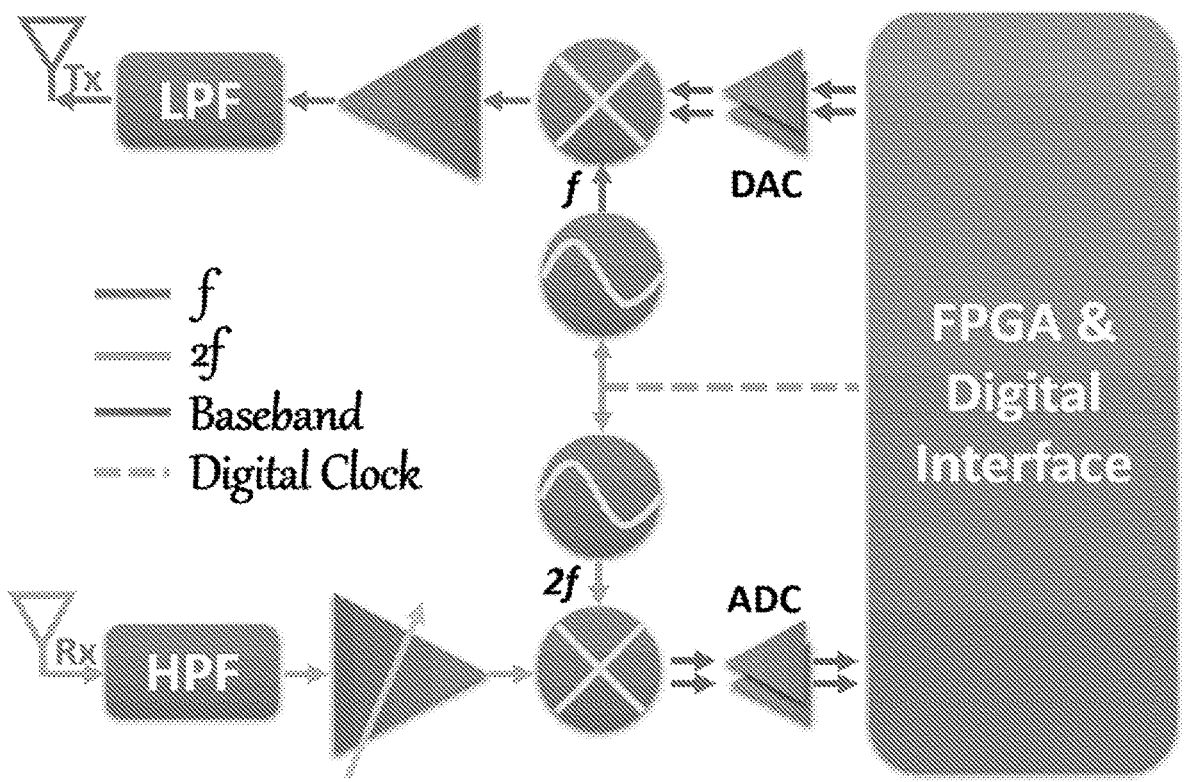
FIG. 5B is a diagram of a harmonic RFID reader according to an embodiment of the present disclosure.

A schematic of an exemplary harmonic RFID reader as a coherent transceiver is shown in FIG. 5B. The same digital clock (dashed line) is fed into two frequency synthesizers at f and 2f for coherent demodulation at 2f. The digital module performs the CDMA protocol. The downlink commands from the reader to the tags are modulated by the digital-to-analog converter ("DAC"), and then unconverted by the mixer to the carrier at f. The harmonic tag backscatters to the reader at 2f, which is down-converted to the base band by the coherent local oscillator at 2f, and sampled by the quadrature analog-to-digital converter ("ADC"). The hardware of a test embodiment of a harmonic reader was conducted with a software defined radio (SDR).

Analyses of the NCS Signal

Figure 6A:
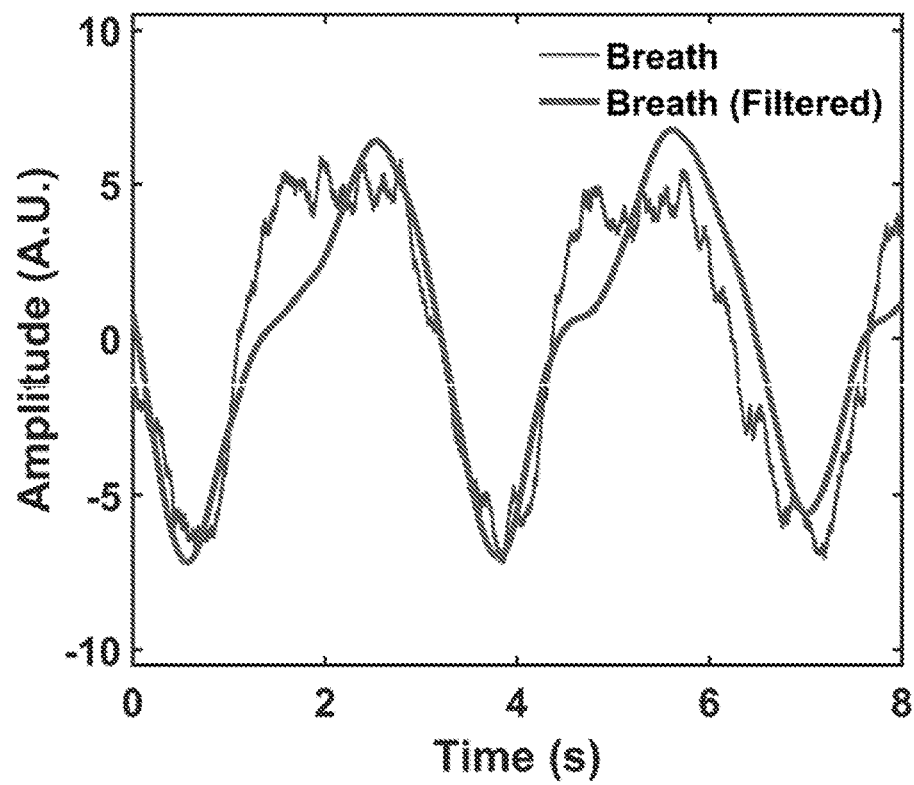
FIG. 6A shows a raw breath signal demodulated from an exemplary harmonic RFID system and the waveform after low-pass filtering.
Figure 6B:
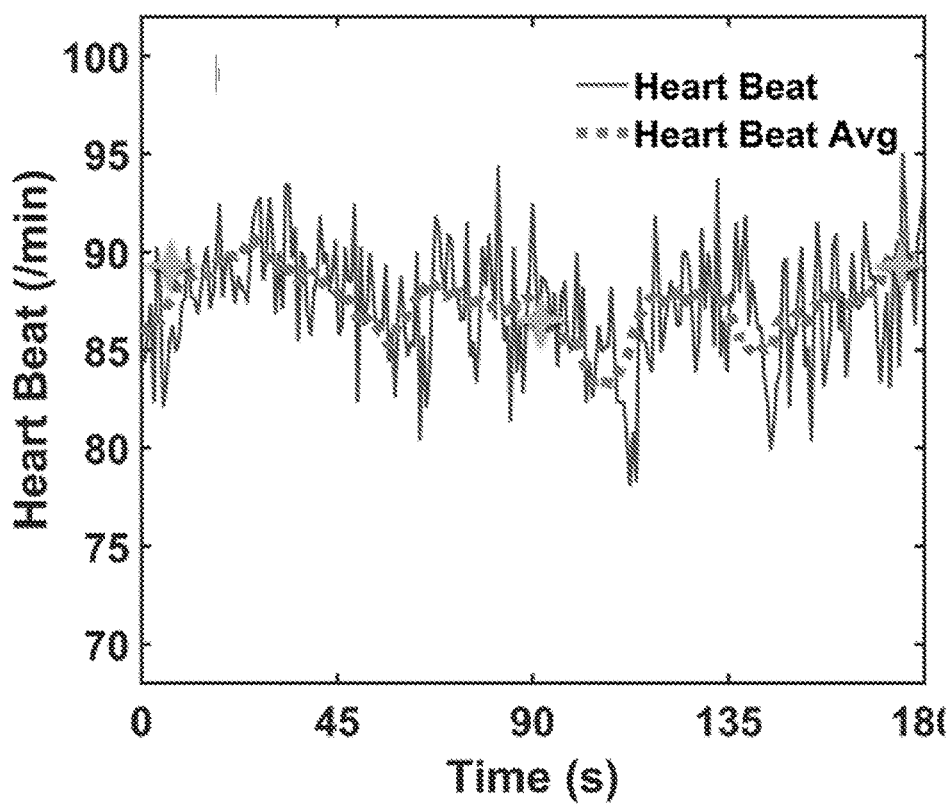
FIG. 6B shows a raw heart beat signal demodulated from an exemplary harmonic RFID system and an average heart beat over a ten-second moving window. The markers show the measurements from OMRON Blood Pressure Monitor mounted on the left forearm.

The phase is more sensitive to the tag physical location with respect to the reader. Hence, when Antenna 2 of a tag is placed on the chest of an individual, breath information can be derived from the phase in the quadrature scheme, as shown in FIG. 6A with raw and low-pass-filtered waveforms. Based on the backscattered phase information, the positions of multiple tags can be calculated with millimeter resolution, which can further derive the respiratory effort. Although the phase variation caused by the chest movement is much stronger than the internal movement of heartbeat and wrist pulse, it is a "common component" for NCS of tissue motion inside the body (as further described above). During experiments performed using embodiments of the present system, NCS heartbeat signals were immune to movement resulting from the individual's breathing. The use of multiple frequencies, improved signal processing, and reflection structure (FIGS. 12A and 12B) can further mitigate heavy multi-path interference. First, the heart rate in FIG. 6B was retrieved from the instantaneous period (the solid line) and from the counts within 10 seconds (the dashed line). The star markers were measured from a commercial blood pressure monitor (OMRON BP760N). Notice that the breath and heartbeat information was independently derived from the quadrature demodulation, and no special filtering or pattern recognition as in the conventional microwave backscattering was required.

Figure 6C:
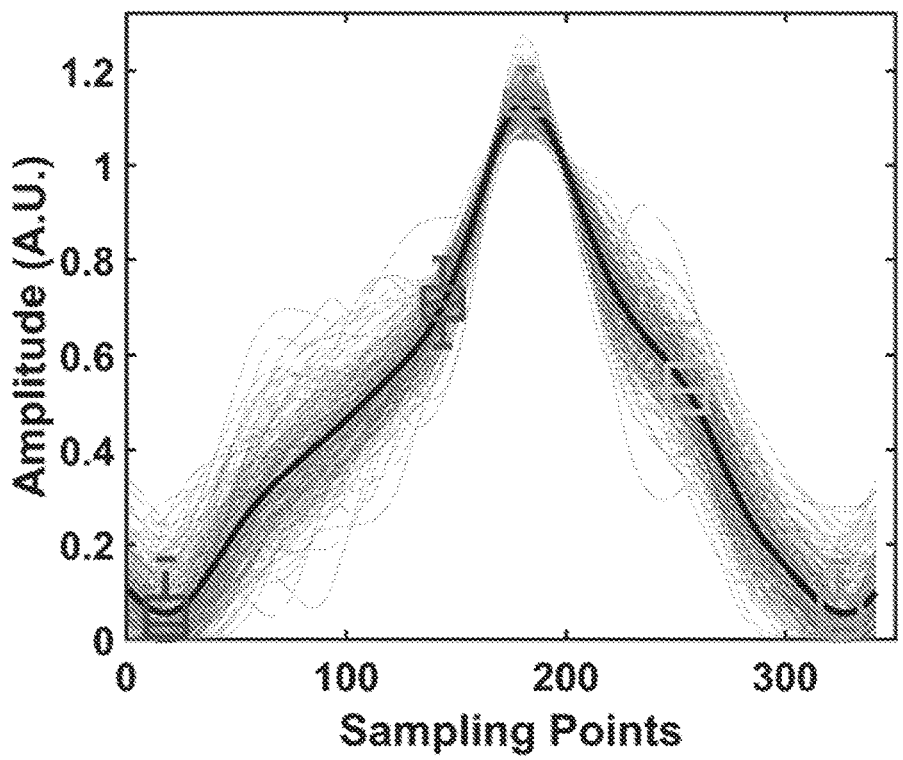
FIG. 6C shows waveforms of a heartbeat during data collection for three minutes.
Figure 6D:
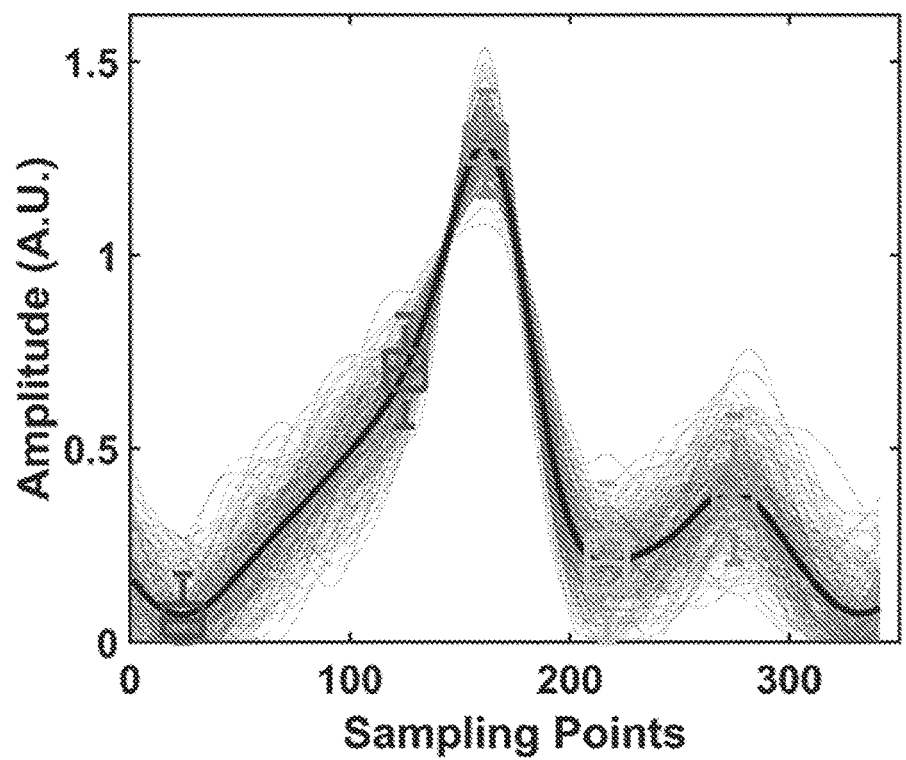
FIG. 6D shows waveforms of a wrist pulse during data collection for three minutes.
Figure 6E:
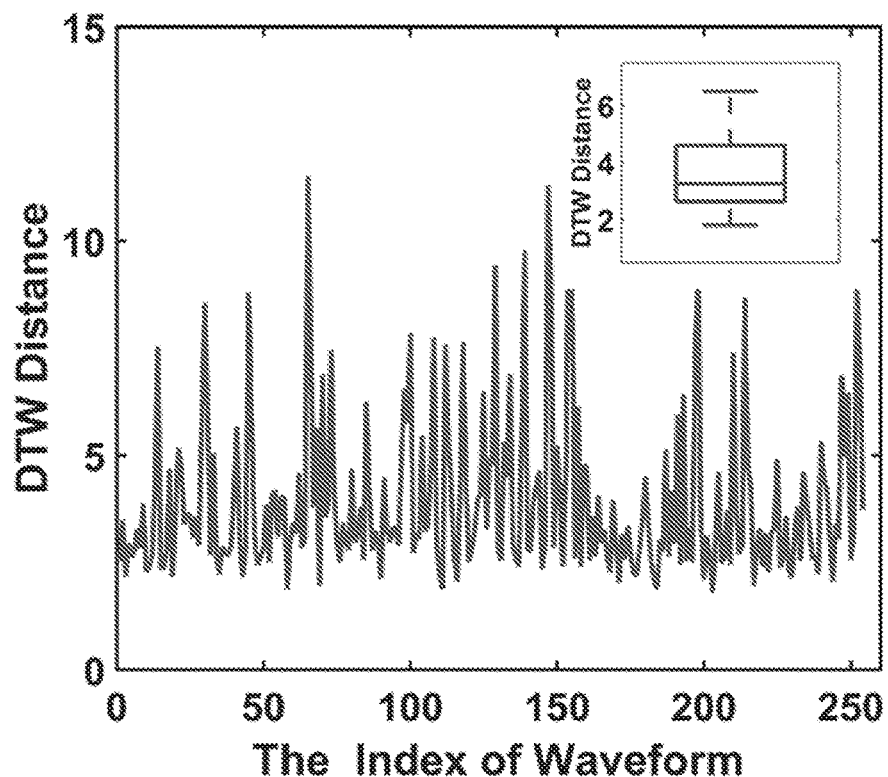
FIG. 6E shows dynamic time warping ("DTW") waveform analysis showing the distance in each waveform of the heartbeat (the inset shows the box-whisker distribution).
Figure 6F:
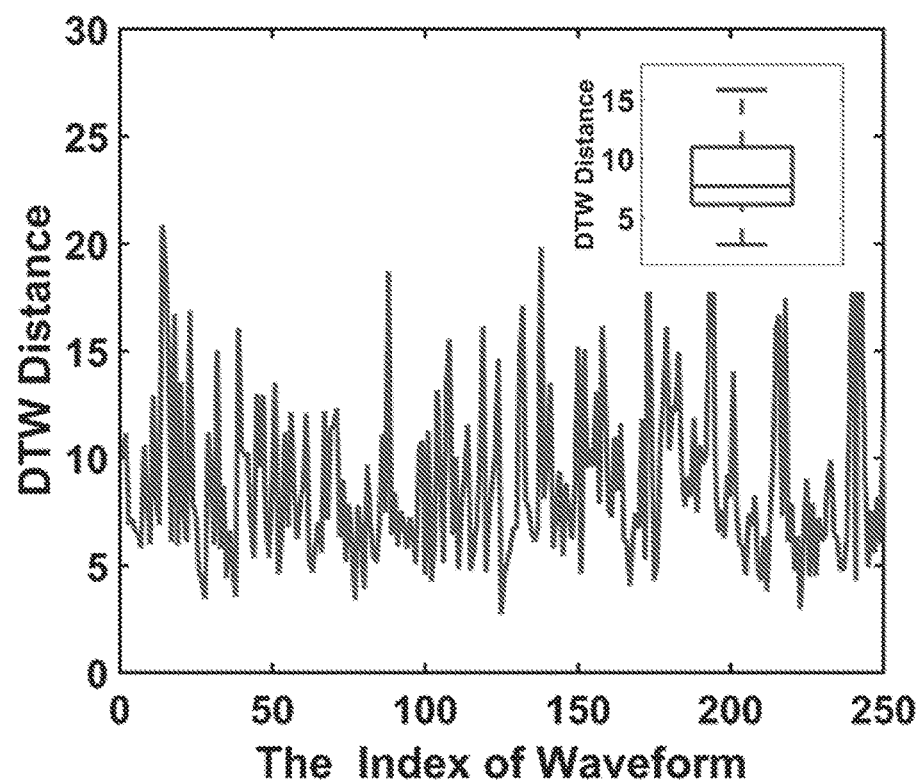
FIG. 6F shows DTW waveform analysis showing the distance in each waveform of the wrist pulse (the inset shows the box-whisker distribution).
Figure 6G:
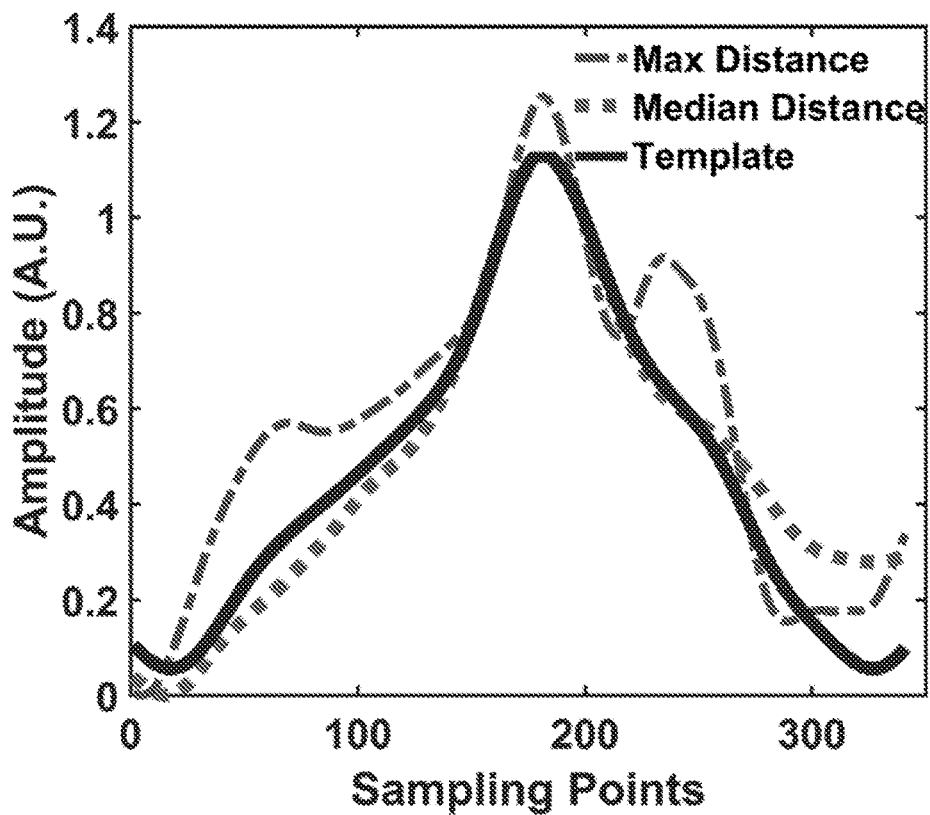
FIG. 6G shows the median- and maximum-distance waveforms compared with the respective DTW template for the heartbeat.
Figure 6H:
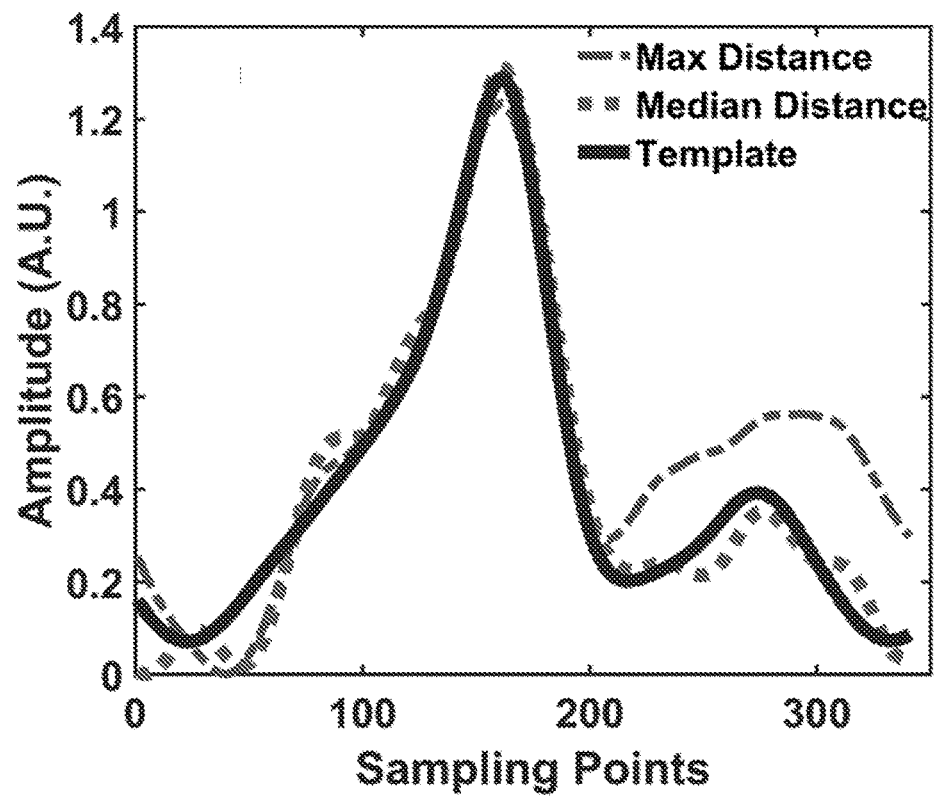
FIG. 6H shows the median- and maximum-distance waveforms compared with the respective DTW template for the wrist pulse.

Because the internal vital signals were retrieved from NCS, the interferometer-like structure significantly increases the sensitivity to enable collection of the motion waveform, similar to a ballistocardiogram ("BCG"). Data from the chest and the wrist tags was recorded simultaneously for 3 minutes. The experiments were conducted with the PCB tag and the reader antenna was ~1.5-2 m away from the person under test. The harmonic signal converted by the tag was about ~20 dBm at 1.9 GHz (2f). To analyze the waveform variation, each period was overlaid to obtain the average and box-whisker deviation of the heartbeat and wrist-pulse waveforms as shown in FIGS. 6C and 6D. The waveforms were normalized to the 90th percentiles of the recorded data. Dynamic time warping ("DTW") was applied to sort the waveforms to derive the detailed features. FIGS. 6E and 6F show the DTW distance for the heart and pulse waveforms, and the insets show the variations. FIGS. 6G and 6H show the comparison of the extracted template waveforms to the maximum-distance and the median-distance waveforms, the latter of which still resemble closely to the template and keep most of the major features, such as the recoil peak in the wrist pulse. The detailed motion waveform analysis can be used as, for example, a cardiogram candidate for arrhythmia and aortic valve diseases.

Figure 7A:
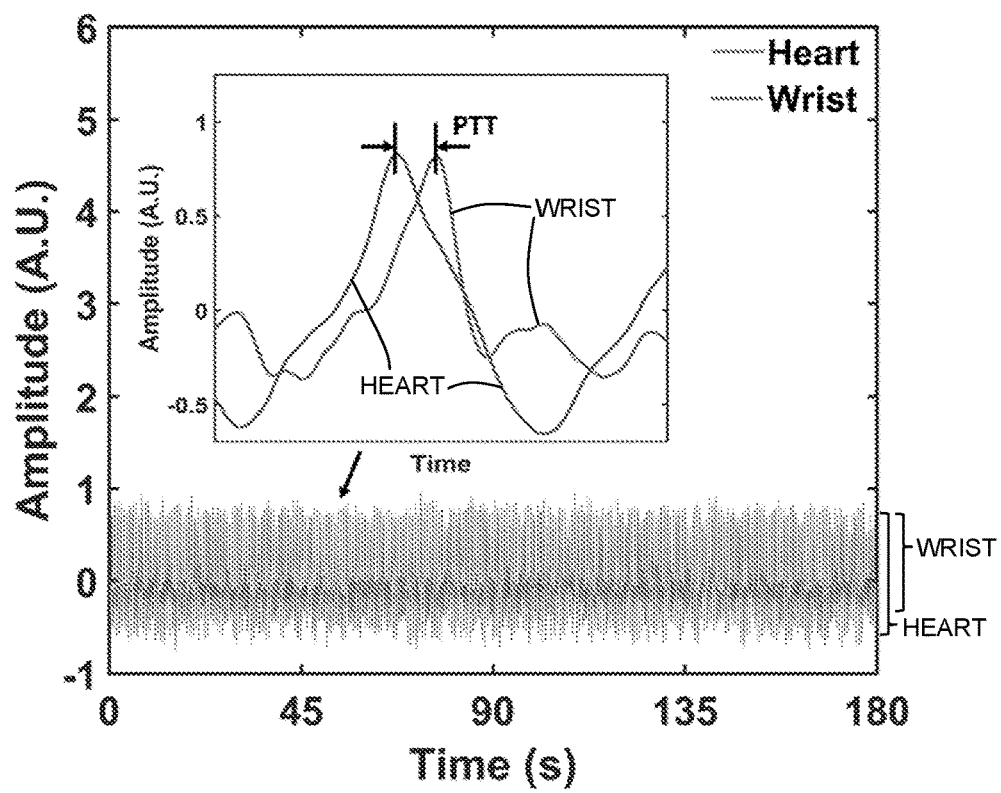
FIG. 7A shows the pulse transit time ("PTT") estimated from the synchronized heartbeat and the wrist pulse waveforms. The inset shows one period of the signals and the extracted PTT.
Figure 7B:
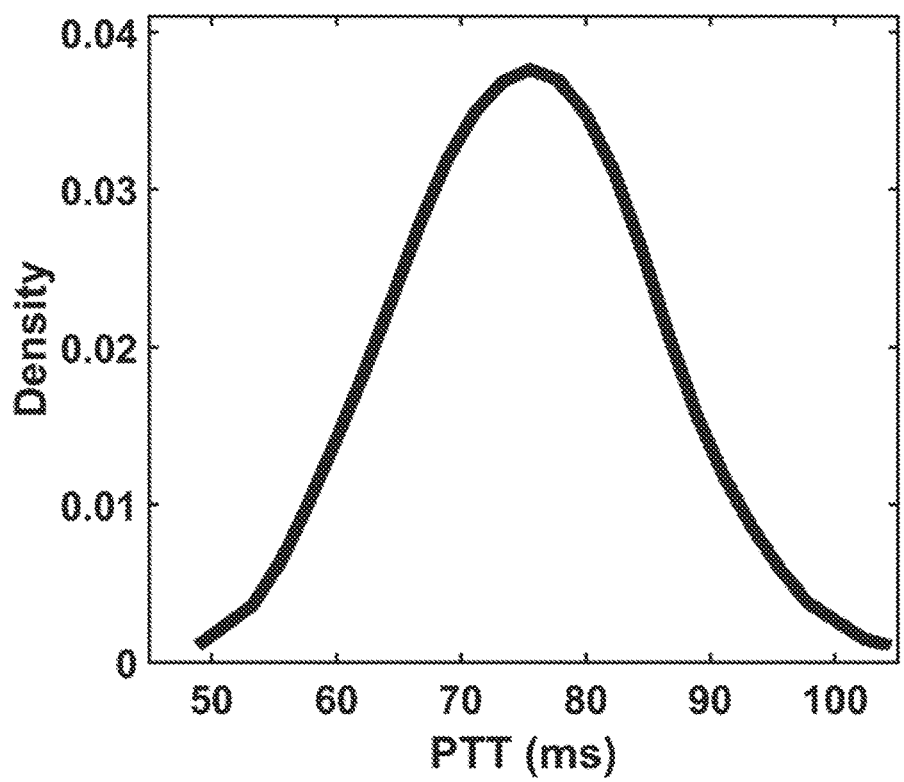
FIG. 7B shows the probability density distribution of the PTT over 3 minutes.
Figure 7C:
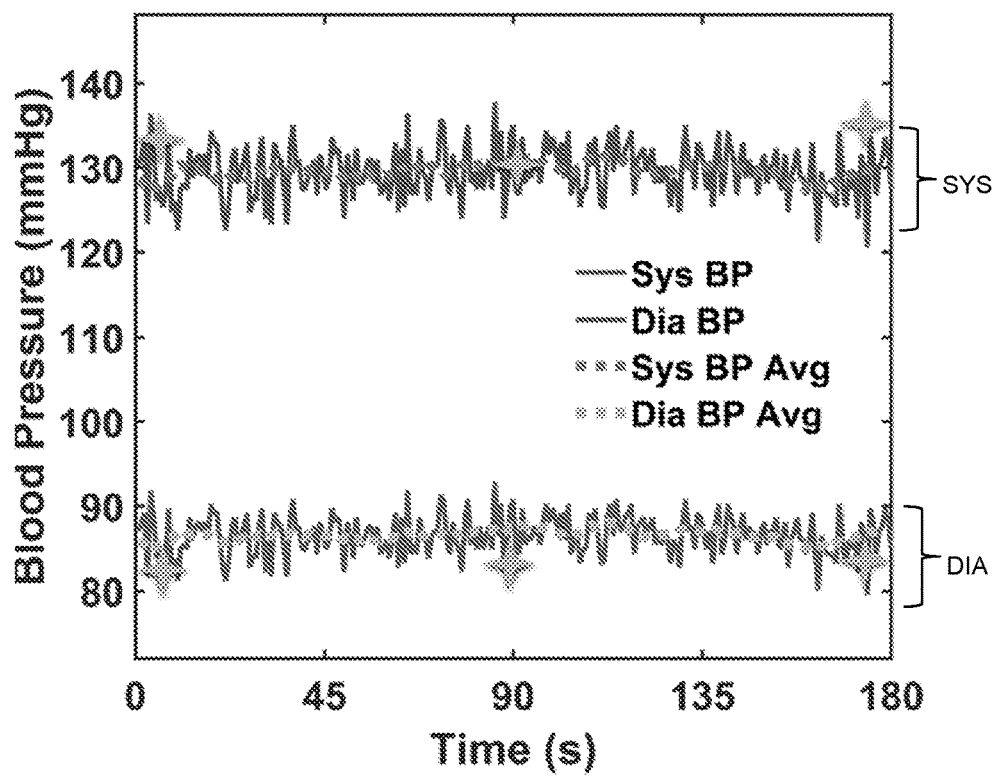
FIG. 7C shows the blood pressure extracted from the PTT when the person under test is seated. The star markers show the blood pressures measured from a commercial blood pressure monitor.
Figure 7D:
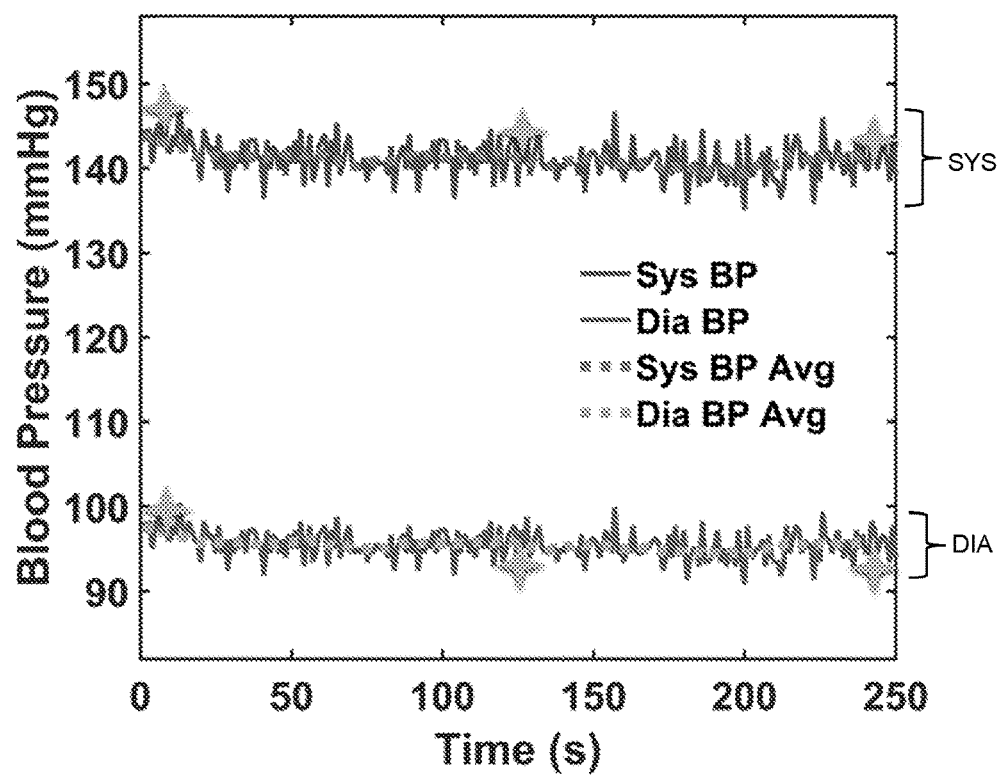
FIG. 7D shows the blood pressure extracted from the PTT when the person under test goes through a moderate activity and standing. The star markers show the blood pressures measured from a commercial blood pressure monitor.
Figure 11:
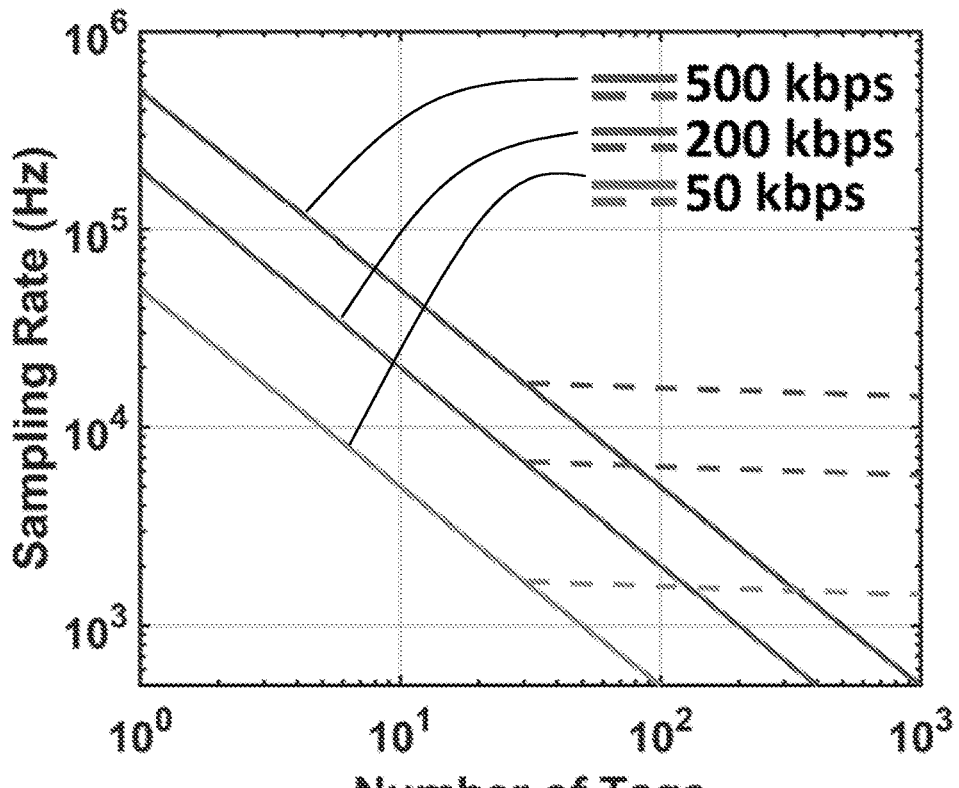
FIG. 11 shows sampling rates of harmonic backscattering with CDMA under various SNR with the number of tags in the reading range. The solid lines are from CDMA when the chip code length is proportional to the number of tags. The dashed lines represent implementation with more efficient semi-orthogonal codes.

The CDMA protocol enables simultaneous monitoring of not only multiple persons, but also multiple points on the same person. The allowable number of CDMA tags is limited by the baseband data rate and is shown in FIG. 11. Comparison of the waveform timing from different body positions offers estimates of the blood pressure ("BP") through the pulse transit time ("PTT"), which can be extracted from the feature points of the proximal and distal arterial waveforms. The present non-contact sensing of blood pressures presents significant advantages over direct pressure-based methods which cause discomfort and disrupt the circadian rhythm especially for long-term monitoring of elderly patients. Each of the chest tag signal (the proximal waveform) and the left wrist tag signal (the distal waveform) were recorded for three minutes, as shown in FIG. 7A. PTT can be readily extracted from the major peaks of the two waveforms. The inset shows the detailed waveforms of a certain period. FIG. 7B shows the probability density of the PTT during the 3-minute recording. The distribution of the PTT may be affected by the sampling jitter and the waveform distortion. One PTT sampling can be obtained for each heartbeat, and the moving average or other signal processing methods can be readily applied to minimize the PTT variation. FIGS. 7C and 7D show the blood pressures calculated from PTT as well as the comparison points (star markers) from the commercial blood pressure monitor (OMRON BP760N). The solid lines are the systolic and diastolic pressures of every heartbeat. The dashed lines are the moving average from 14 sampling points around 10 seconds. The data in FIG. 7C were collected when the person under test sat on a chair for about 30 minutes, while the data in FIG. 7D were collected after a moderate activity.

Detailed Methods

We used CST Microwave Studio for electromagnetic simulation. Zubal Phantom was used to construct the dielectric models. The tissue geometric information was calibrated with data from computed tomography (CT) and magnetic resonance imaging (MRI). The resolution of the voxel was 3.6 mm×3.6 mm×3.6 mm. The microwave properties of various tissues were mapped with CST Bio-library. We first pre-processed the Zubal Phantom data into the file structure of tissue geometric coordinates together with the tissue indices, layer by layer. CST then imported the files and automatically built every voxel with the three-dimensional coordinates and tissue properties to establish the dielectric model controlled by the scripts of CST built-in Visual Basic for Applications (VBA) Macro language. The process is analogous to three-dimensional printing, but only virtually in the CST software. Dynamic simulations of heartbeats and wrist pulses were realized by geometrical variations, where the geometries of the heart and the wrist vessel were changed according to the preset dimension serving as the ground truth.

The passive harmonic backscattering tag was prototyped by a custom PCB, which was modified from the Wireless Identification and Sensing Platform (WISP). The harmonic generator on the tag was designed with a nonlinear transmission line (NLTL), which includes a ladder structure of inductors and varactors. The NLTL can provide high conversion efficiency with low input power, which is essential for passive backscattering tag design. The harmonic RFID reader and the antenna reflection system were built on the platform of National Instrument Ettus Software Defined Radio (SDR) B210. To realize coherent harmonic demodulation, the local oscillator (LO) of the receiver needed to be directly derived from the second harmonic frequency of the transmitter LO. The real-time control and demodulation software was composed in LabVIEW. The operating frequency was f=950 MHz (second harmonic at 2f=1.9 GHz) with the homodyne modulation scheme. The downlink analogue baseband was 10 kHz and the uplink analog baseband after harmonic conversion was 20 kHz. Both digital-to-analogue and analogue-to-digital conversions operate at 106 samples per second (Sps). The raw digital signals were then filtered, digitally downconverted to the D.C. band, and decoded with the CDMA algorithm to distinguish the information from each tag. The signal from each tag was then downsampled by the sampling rate of 500 Sps. The breath signal was processed by a low-pass filter with a cutoff frequency of 0.8 Hz. The heartbeat and pulse signals were processed by the bandpass filter between 0.9 Hz and 15 Hz. The present operating range for the passive tag is ~1.5 m, limited by the WISP platform. The range can be extended towards 10 m according to the operation of conventional RFID systems in the same frequency band.

Figure 2A:
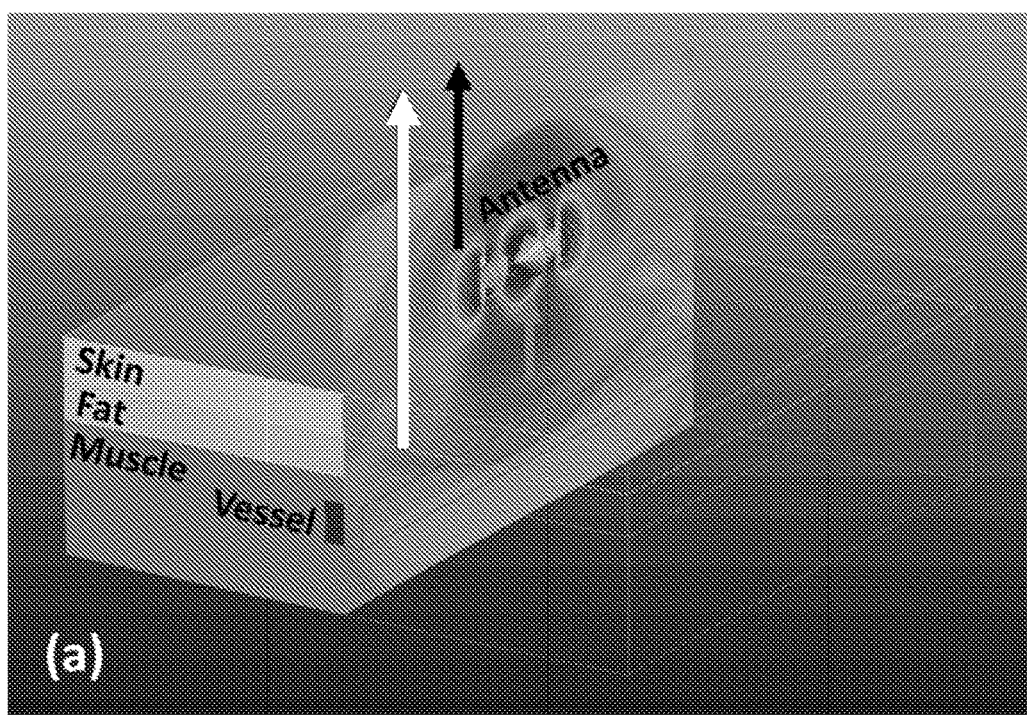
FIG. 2A depicts an NCS simulation of a conceptual skin and tissue structure with a nearby blood vessel, wherein a dipole antenna emitting a 1.85 GHz, 0 dBm signal is placed above the skin and does not require immediate skin contact. The tissues above the blood vessel include the skin, fat, and muscle. The geometrical changes of the vessel from pulses will modulate the near fields and change the far-field backscattering patterns.
Figure 2B:
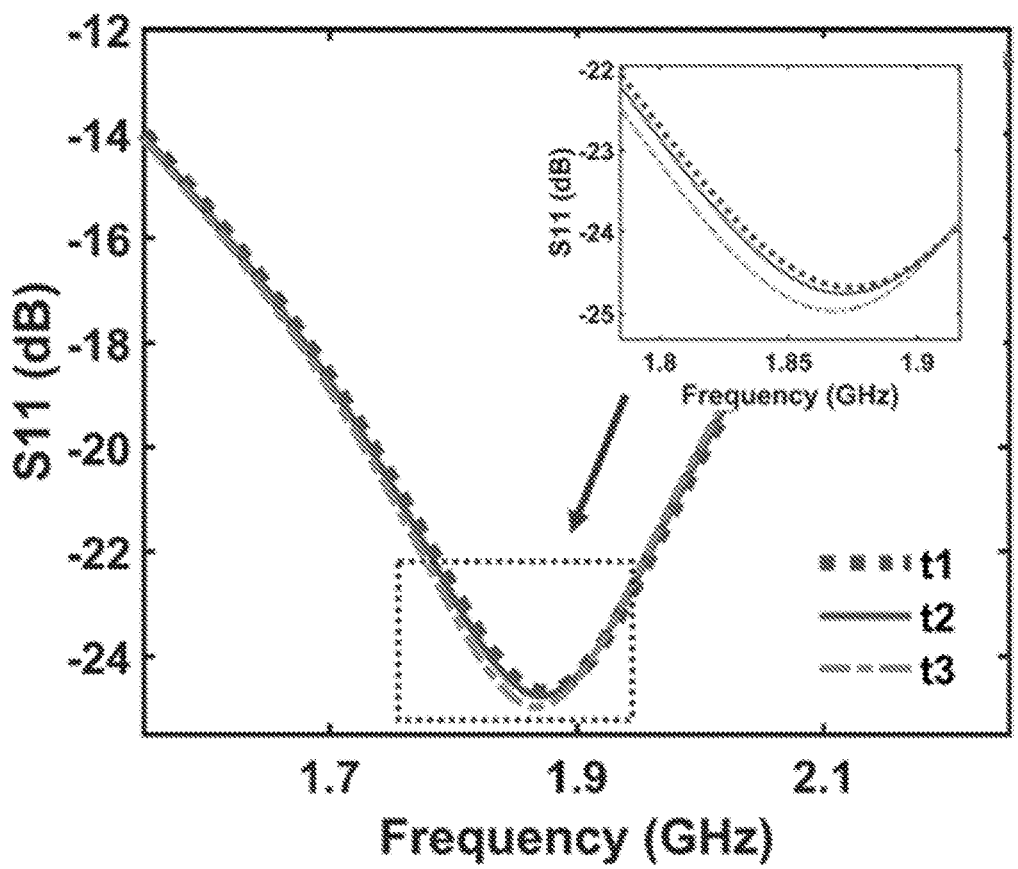
FIG. 2B shows the antenna reflection parameter $S_{11}$ for the quasi-static vessel of FIG. 2A, wherein cross sections marked as t1, t2 and t3.

In another simulation, the antennas were deployed close to the heart and the left wrist where the pulse can be felt. The signal source should be within the near-field zone of the antennas, but no direct skin contact by the antennas is required. FIG. 2A shows the simplified lower arm structure and the electric field in the near-field region in CST Microwave Studio. The antenna was configured to couple more energy into the tissue for larger signal-to-noise ratio ("SNR"). The antenna reflection parameter $S_{11}$ is shown in FIG. 2B. The center frequency was about 1.85 GHz. Because of the high permittivity of tissue, the antenna bandwidth was broader. The simulation result in FIG. 2A shows that the electric field coupled into the layers of skin, fat, and muscle as well as the nearby blood vessel.

Figure 4A:
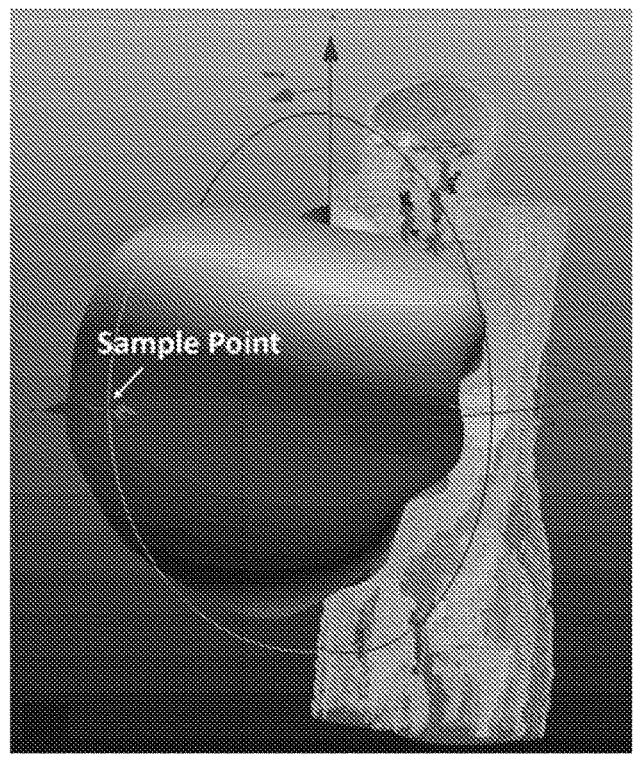
FIG. 4A shows simulated RF radiation patterns for heartbeat, wherein the far-field sample point is 1 m in front of the chest.
Figure 4B:
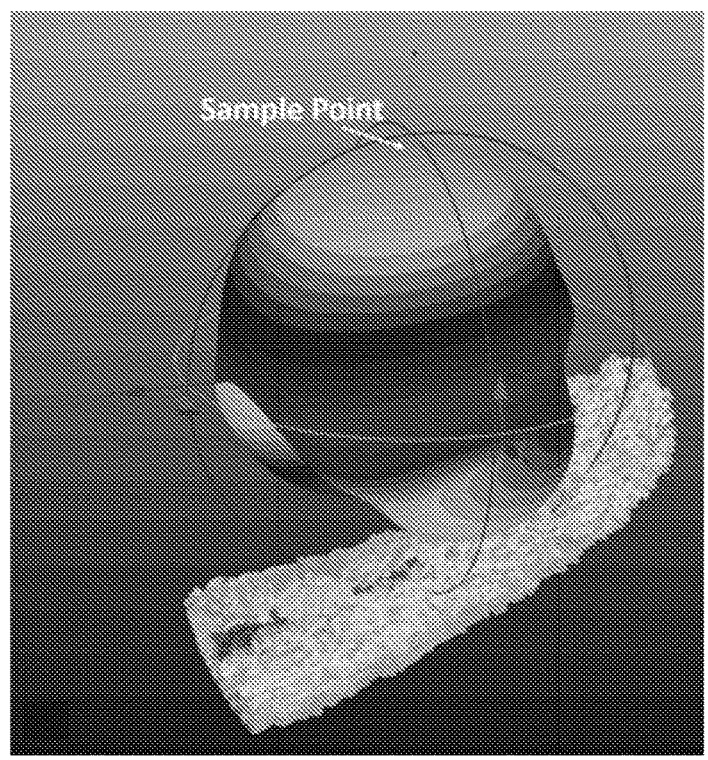
FIG. 4B shows simulated RF radiation patterns for a wrist pulse, wherein the far-field sample point is 1 m above the wrist.

To simulate mechanical motion coupled onto the EM field, a small vibration was introduced into the geometric scale of the heart and the wrist vessel, and the vessel cross section in the tissue model varied quasi-statically in the time stamps of t1, t2, and t3 to represent the pulse vibration. The normalized vibration amplitudes are shown with the thick solid lines in FIGS. 3A and 3B. FIGS. 4A and 4B shows far-field patterns simulated in CST Microwave Studio. The shaded ramps indicate phase, while the shape represents the amplitude contour of the co-polarization electric field. The far-field signals (with sampling points 1 m in front of the chest (FIG. 4A) and above the wrist (FIG. 4B)) were recorded and are shown in FIG. 3A. It can be seen that the demodulated heart signal (depicted in FIG. 3A with a dashed line) and the wrist pulse signal (depicted with a dotted line) match well with the known vibration.

The far field can be considered as the interference results of two near-field components: the direct propagation wave from the antenna (black arrow of FIG. 2A) and the scattered signal from the inner tissue (white arrow). When a heartbeat causes the blood vessel to vibrate, the phase of the scattered signal will be modulated due to interference with the direct propagation. Because the demodulated vessel-motion signals are derived from the differential interference, antenna motion caused by breathing or other body movements can be regarded as the common mode that can be rejected. Alternatively, the scattered signal can be coupled back to the same antenna to be coherently demodulated, which is indicated as the gray arrow in FIG. 2A and the resulting $S_{11}$ in FIG. 2B.

FIG. 2A illustrates how a portion of the EM field energy from the antenna radiates directly to the far field as indicated by the black arrow, while the other part of the EM energy couples into the multi-layer tissue, all the way down to the sensing target which is the arterial vessel here. Because of the dielectric constant differences, the mechanical motion of the arterial vessel from pulses will modulate the backscattering signal, which is indicated by the white arrow. This signal also propagates to the far field together with the directly radiated signal. From the point of view of the EM field, these two signals originate from the same source but go through different paths i.e., they are coherent and the amplitude of the combined signal will change due to the phase difference. One can thus see how the mechanical motion of the vessel will cause amplitude modulation. This operational principle is similar to the interferometer, and the near-field modulation can be treated as the "differential component" in the interferometer analogy. On the other hand, the movements of the surface or the entire body, such as respiration and body motion, will change the phases of both signal paths simultaneously, which can be considered as the "common mode" in the interferometer structure. Hence, NCS not only utilizes the sensitivity of the interferometer structure to enhance performance, but also isolates the two different modulations: one from inside the body with near-field coupling and the other from the surface motion with direct emission.

Passive Backscattering

In an exemplary embodiment, NCS was implemented by passive harmonic RF identification (RFID) tags where vital sign signals were modulated on the harmonic backscattering together with the tag ID. Besides the ultra-low cost, the simple and robust packaging of such a passive tag embodiment enables direct fabric integration with laundry readiness. An exemplary harmonic RFID reader and antenna reflection system were built using the Ettus Research™ software-defined radio ("SDR") B210 platform.

Figure 8B:
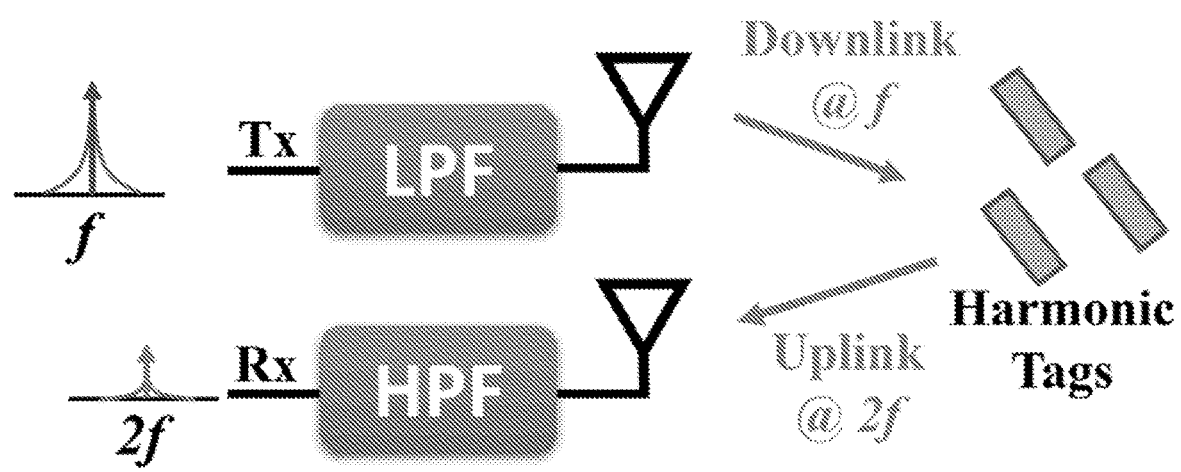
FIG. 8B is a diagram showing an embodiment of the presently-disclosed principle of harmonic RFID backscattering, wherein Tx stands for transmitter, Rx for receiver, LPF for low-pass filter, and HPF for high-pass filter.
Figure 9A:
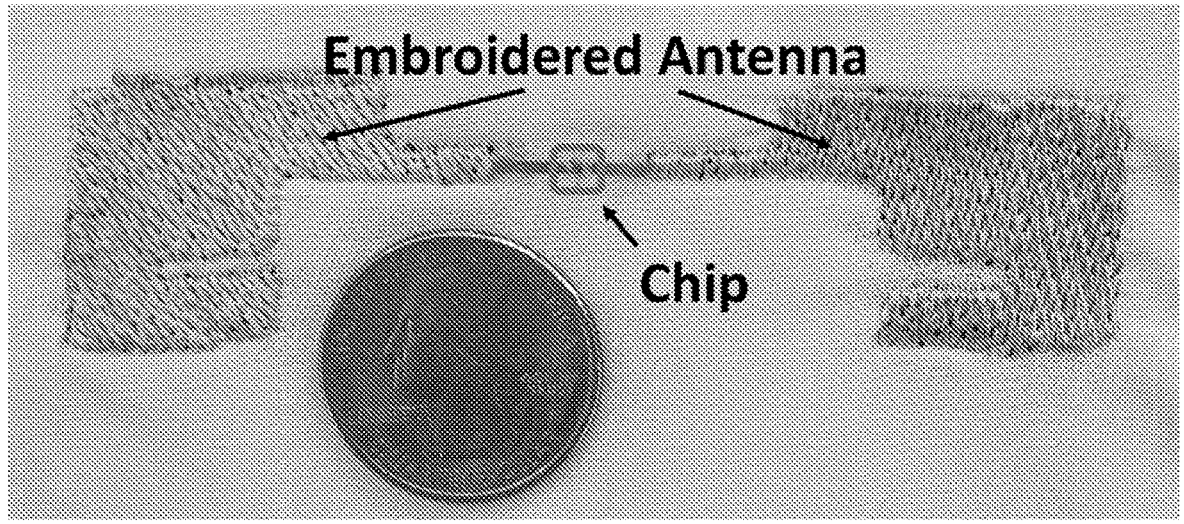
FIG. 9A is a photograph of an RFID sensor tag chip of an embodiment of the present disclosure integrated with the embroidered antenna on fabric.
Figure 9B:
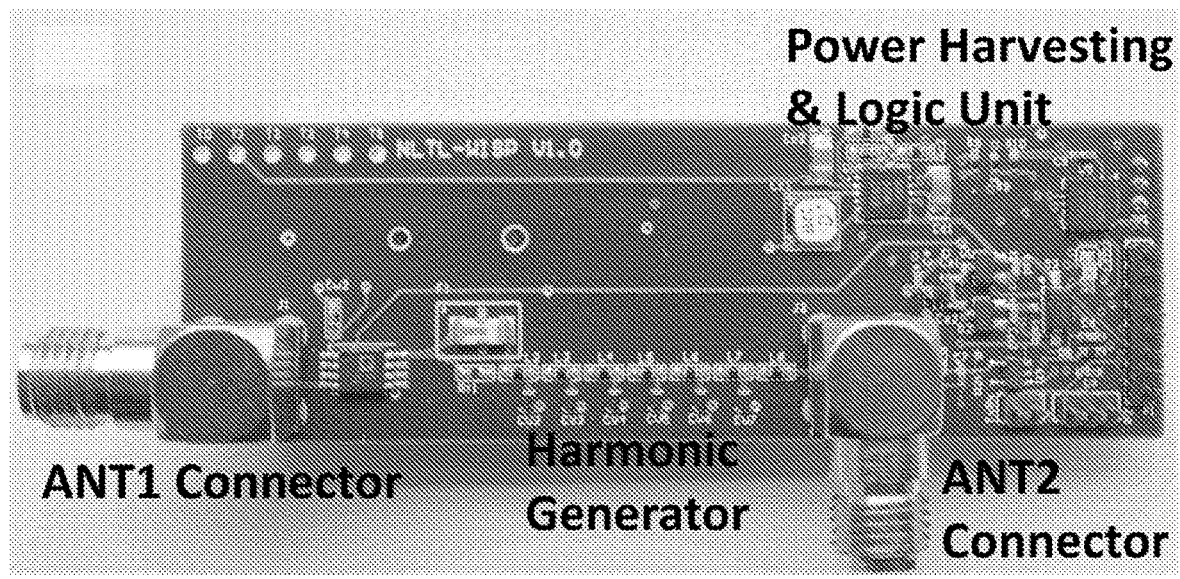
FIG. 9B is a photograph of a PCB prototype of a harmonic RFID tag according to an embodiment of the present disclosure.

A schematic of an exemplary harmonic tag is shown in FIG. 5A, and FIG. 9B is a photograph of a PCB prototype of such a tag. All of the exemplary NCS operations were performed on the PCB prototype of the harmonic tag based on the Wireless Identification and Sensing Platform ("WISP") in FIG. 8B for ease of protocol access. The prototype RFID sensor tag chip was integrated with an embroidered antenna on fabric (shown in FIG. 9A). The fabric RFID tag was used to demonstrate the feasibility of garment integration for the presently-disclosed approach. Normal RFID data transaction of tag ID and temperature sensing according to the electronic production code ("EPC") protocol were verified.

The real-time demodulation software was composed in LabVIEW. The operating frequency was f=950 MHz (2nd harmonic at 2f=1.9 GHz) with the homodyne modulation scheme. The downlink analog baseband was 10 kHz, and the uplink analog baseband after harmonic conversion was 20 kHz. Both digital-to-analog and analog-to-digital conversions were operating at $10^6$ samples per second (Sps). The present operating range for the passive tag was about 1.5 m, limited by the WISP platform. The range can be extended towards 10 m according to the operation of conventional RFID systems in the same frequency band.

The principle of harmonic RFID backscattering is shown in FIG. 8B. In an embodiment, a reader transmits a downlink signal at the fundamental frequency f, which will power up any harmonic tags within a range of the reader. The harmonic tag receives the downlink RF signal at f from the reader which goes through the tag Antenna 1 and splits to two parts: one for energy harvesting to provide DC power for tag circuits, and the other is fed into passive harmonic generation at 2f to be re-emitted from Antenna 2 as the uplink carrier to eliminate reader self-interference and reflection from nearby objects. In this way, Antenna 2 serves as the NCS transmitter. A low-pass filter ("LPF") at the transmitter (Tx) and a high-pass filter ("HPF") at the receiver (Rx) further isolate the two carriers at f and 2f. With coherent harmonic backscattering, Rx has a much lower noise floor. Hence the Rx sensitivity can be increased, which enables the system to distinguish the weak vital signals modulated on the uplink. An RF switch in front of the harmonic generator (FIG. 5A) can modulate digital information by on-off keying ("OOK"), similar to conventional RFID operations. The digital information can include the tag ID as well as additional information from the on-tag sensors.

Multi-tag access may be accomplished through the use of a protocol such as, for example, the code-division multiple-access ("CDMA") protocol. The use of such a protocol can provide better inter-tag synchronization, higher channel efficiency, and higher power efficiency in harmonic backscattering. The allowable number of CDMA tags is limited by the baseband data rate and is shown in FIG. 11. The solid lines are the CDMA code with the chip code length linearly proportional to the number of tags. However, when the number becomes larger, the semi-orthogonal code length can be nearly logarithmic, shown as the dashed lines. To recover the waveform details, the sampling rate should be above 500 Hz, which can be readily fulfilled in the exemplary embodiment of the harmonic backscattering system with CDMA.

The phase of the backscattered signal is modulated by the additional path and hence the relevant mechanical movement, which is the artery and venous pulses here. At the far field, the two parts interfere with each other like an interferometer, i.e., the wrist pulse will modulate the amplitude of the EM wave at the receiver. Meanwhile, external movement such as, for example, hand waving, modulates the phases of both parts, and will result in the common modulation for both signals. In short, hand motion will be the common mode and the wrist pulse will be the differential mode. FIG. 1A shows the sensing antenna deployed near the chest area to monitor the heartbeat. Due to the near-field effect, the EM field is coupled into the torso, and the backscattered signal is modulated by the heartbeat. The direct transmission and backscattered signals are received by the receiver at the far field. The two parts are from the same source with different paths, and they will interfere with each other where the heartbeat can be demodulated from the amplitude. The chest movement caused by the breath changes the phase of both signals, which is the common mode of NCS. Similar to the hand motion case in the wrist tag, the breath and heartbeat signals are well isolated due to the common and differential modes independent of the latter filtering.

Figure 22A:
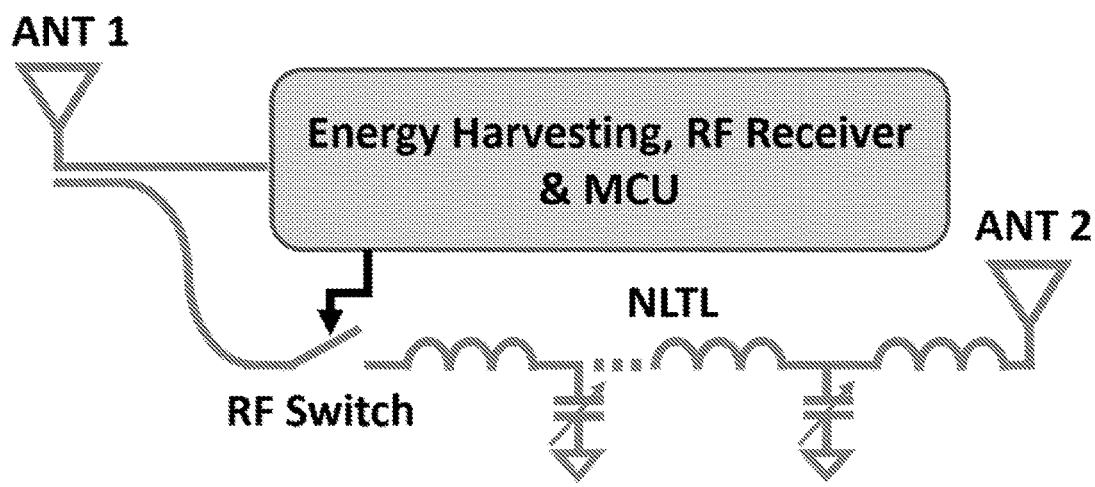
FIG. 22A is a schematic of a harmonic RFID backscattering tag.
Figure 22B:
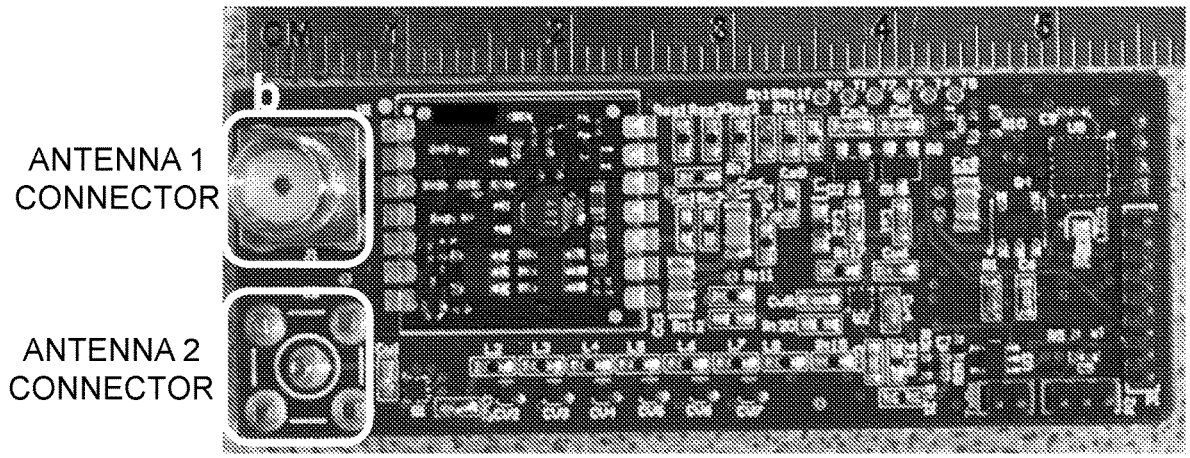
FIG. 22B is a photograph of a PCB prototype of the tag depicted in FIG. 22A.
Figure 30:
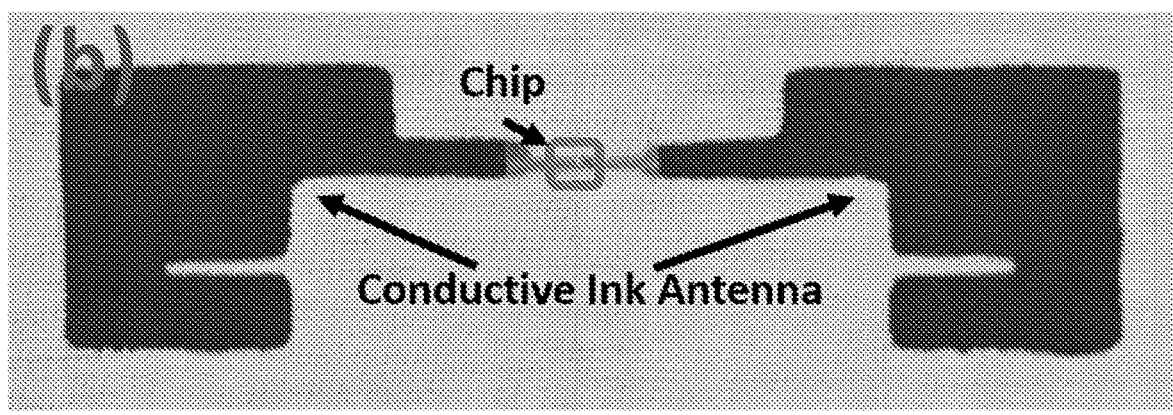
FIG. 30 is a photograph of an exemplary tag running on the Electronic Product Code (EPC) protocol with the fabric antenna by conductive ink.

To implement NCS as a wearable device in indoor environment, an exemplary harmonic RFID system with the code division multiple access (CDMA) protocol was used. The RF schematic is shown in FIG. 8B. The reader transmits the downlink (reader-to-tag) signal at frequency f. The harmonic tag receives the downlink signal and backscatters the 2nd harmonic at 2f as the uplink (tag-to-reader) signal. The transmitter (Tx) and receiver (Rx) spectra are separated to increase the signal-to-noise ratio (SNR) and the receiver sensitivity. The CDMA protocol provides better tag synchronization, higher sampling rate, lower jitter and lower power consumption. The schematic of the harmonic tag is shown in FIG. 22A. Antenna 1 (ANT 1) receives the downlink RF signal, where the tag harvests the RF energy, powers up the logic circuits and demodulates the downlink information. Part of the downlink RF signal is coupled to the nonlinear transmission line (NLTL) to generate the 2nd harmonic signal, which is modulated by the RF switch and transmits back to the reader through antenna 2 (ANT 2). The backscattered 2nd harmonic signal performs the NCS function and is then received by the Rx antenna of the reader. The PCB prototype for the following experiments is shown in FIG. 22B, with the dimension about 57×20 mm. The tag can be further integrated as a passive chip and packaged with garment directly where the antenna can be implemented by the conductive ink in FIG. 30 and by embroidering in FIG. 9A.

Figure 10:
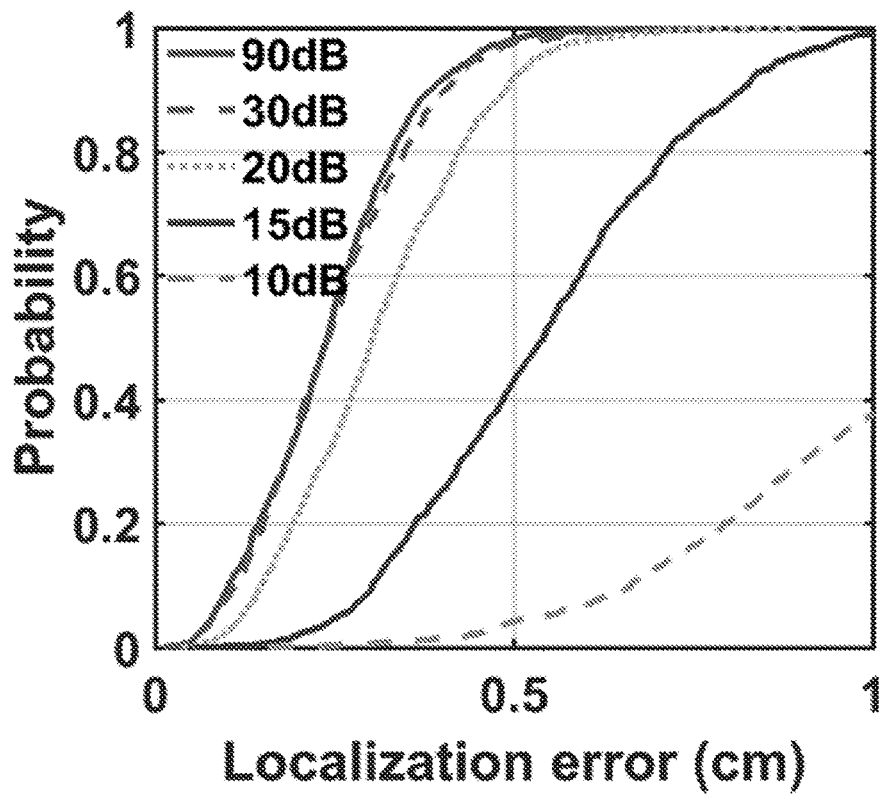
FIG. 10 shows localization error of a harmonic RFID tag with CDMA (200 tags) under various system SNR.

FIG. 10 shows the tag localization error when the phase-based harmonic backscattering localization method was applied with the CDMA protocol. The simulation results show the cumulative probability function of the localization error under various SNR. Because self-interference and direct reflection have been eliminated in the harmonic backscattering system, the noise floor can be very low to readily achieve SNR of 20 dB.

Figure 12A:
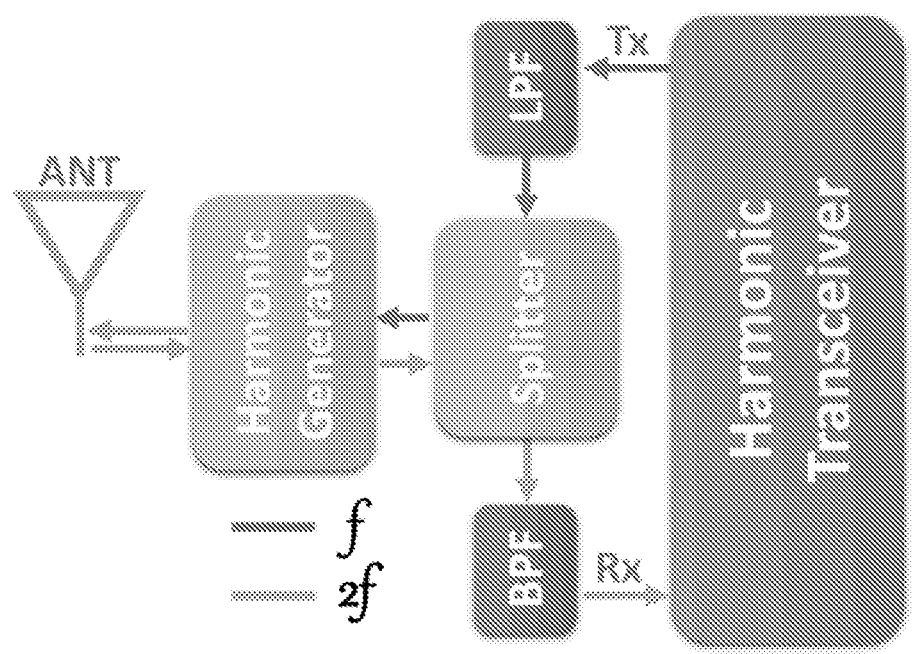
FIG. 12A is a diagram showing an antenna reflection system according to an embodiment of the present disclosure. The splitter is bi-directional and can be replaced by a broadband circulator. The harmonic transceiver and harmonic generator are similar to those used in the passive tag system of FIGS. 5A and 5B.
Figure 12B:
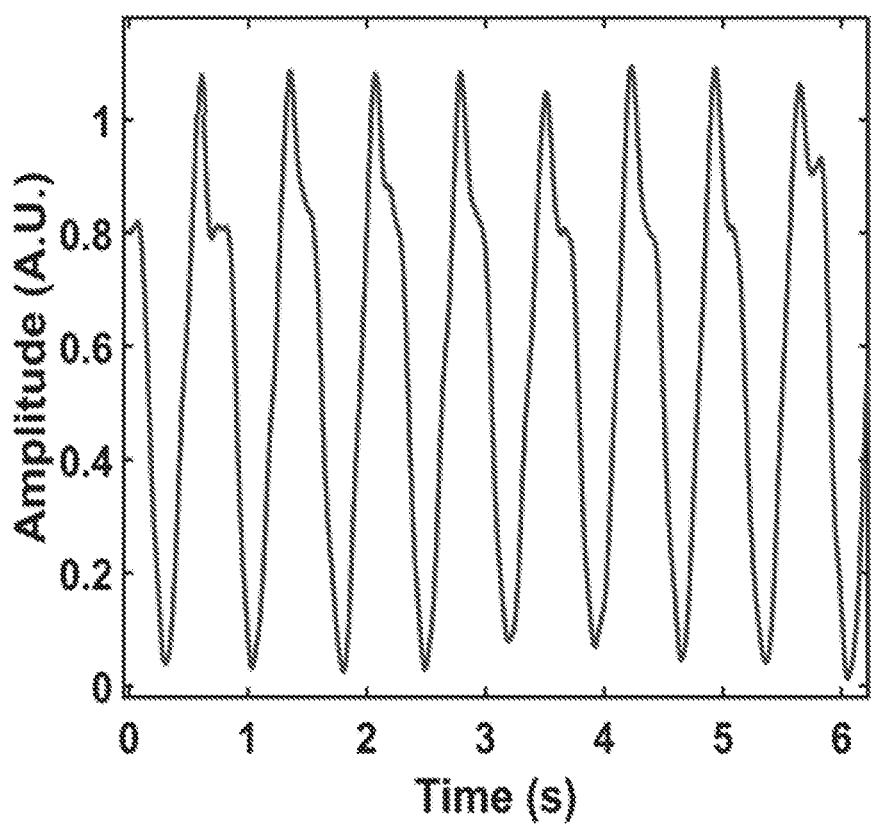
FIG. 12B is a diagram showing the measured heartbeat waveforms using the antenna reflection system of FIG. 12A.

The experimental antenna reflection system is shown in FIG. 12A and the measured heartbeat waveforms in FIG. 12B. The schematic in FIG. 12A can be realized by an active tag mounted on the garment near to the heart, where the tag antenna performs the NCS function. For direct comparison, a harmonic generator and a harmonic transceiver were chosen to be similar to the passive tag system of FIGS. 5A and 5B to build the antenna reflection unit. Other designs may be used, including, for example, using high-isolation circulators in a single frequency. Both the signal splitter and the harmonic generator used in the experimental system were bi-directional. The signal from Tx at f is coupled to the harmonic generator and then to the antenna at both f and 2f. The antenna reflection was fed through the harmonic generator and the splitter again, but only the signal around 2f was selected by the band-pass filter ("BPF") to feed back to Rx for coherent demodulation. Vital signals over 2f were sampled and sent to the remote devices in full digital format, where indoor inter-symbol interference caused by multi-path and occupant motion could be readily eliminated by standard techniques with low data rates. FIG. 12B shows the demodulated heartbeat signal (a 0.9-15 Hz filter was applied), normalized to 90 percentile of the data. With the antenna reflection scheme, the vital signals detected by NCS were more immune to the severe multipath disturbance caused by the ambient movement, such as the case of a crowded room.

Figure 13:
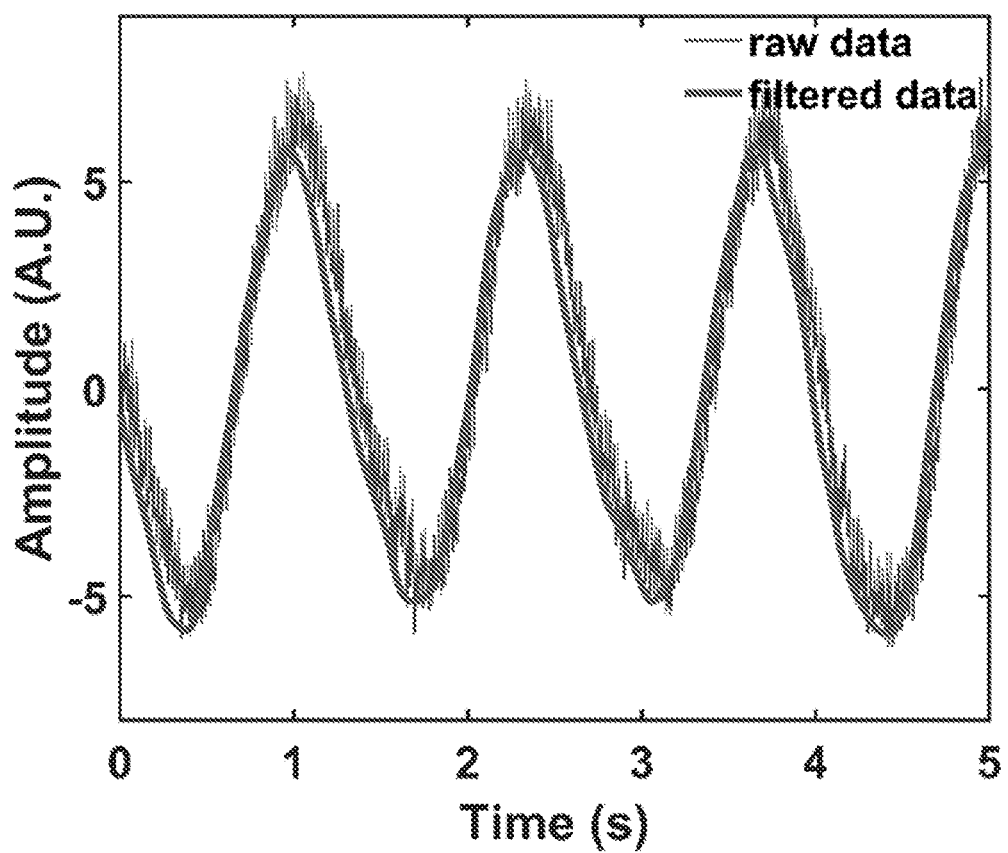
FIG. 13 shows calibration results when a near-field coherent sensing antenna according to an embodiment of the present disclosure is placed near an asymmetry-axle direct-current speed reduction motor. The demodulated sinusoidal waveform is the 1D phase projection of the 2D periodical asymmetric rotation.
Figure 14:
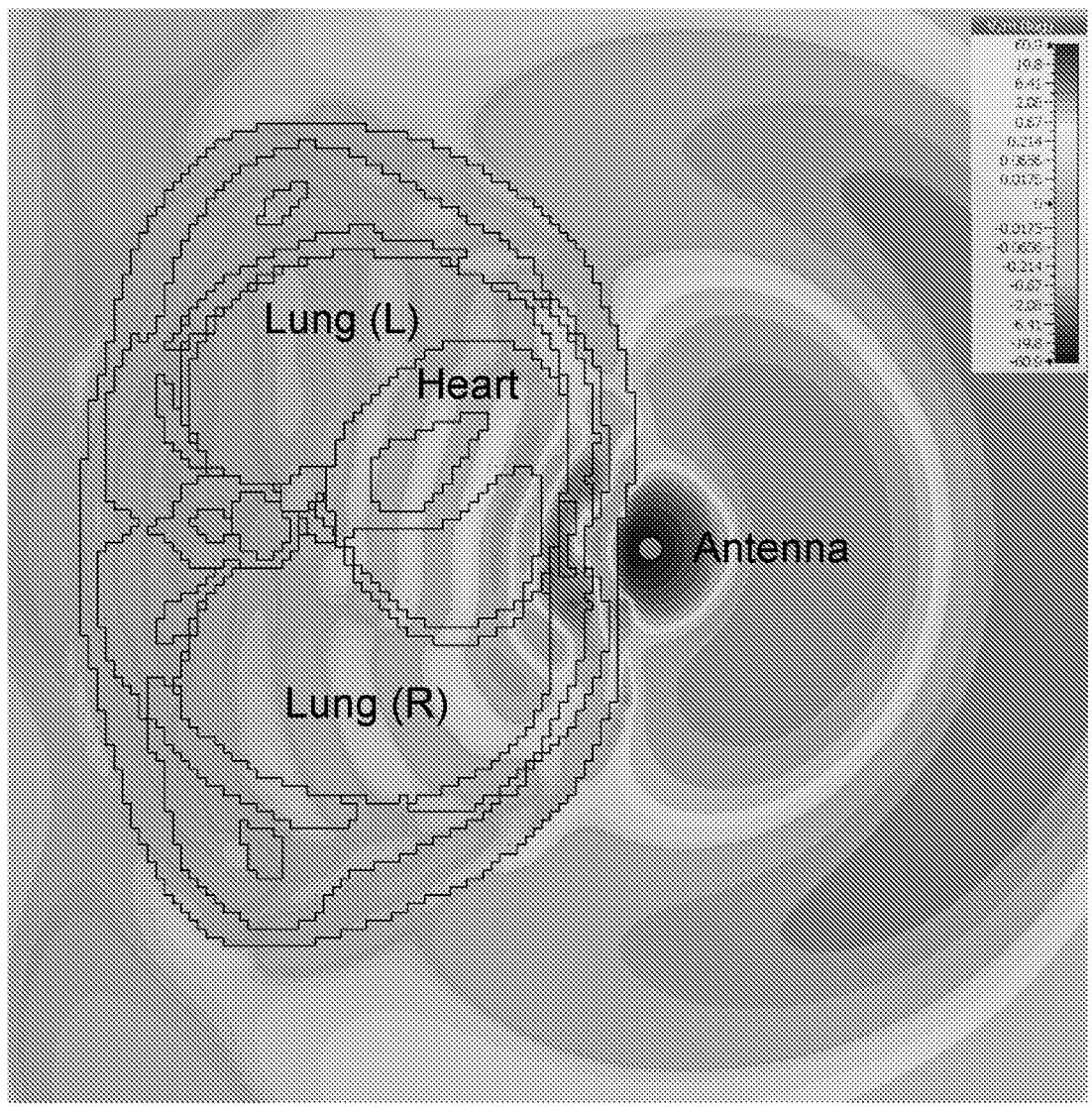
FIG. 14 is a cross section of electromagnetic wave simulation of the co-polarization E-filed at 1.8 GHz for the antenna near-field coupling to the heart motion.

As an independent verification procedure of the NCS operation without direct mechanical contact, an asymmetry-axle motor (ASLONG JGB37-520) with known rotation speed was used (FIG. 13). The antenna of the passive tag was placed close to the asymmetric rotation axle, and the mechanical rotation was transduced to a sinusoidal waveform through phase modulation and demodulation.

Figure 15:
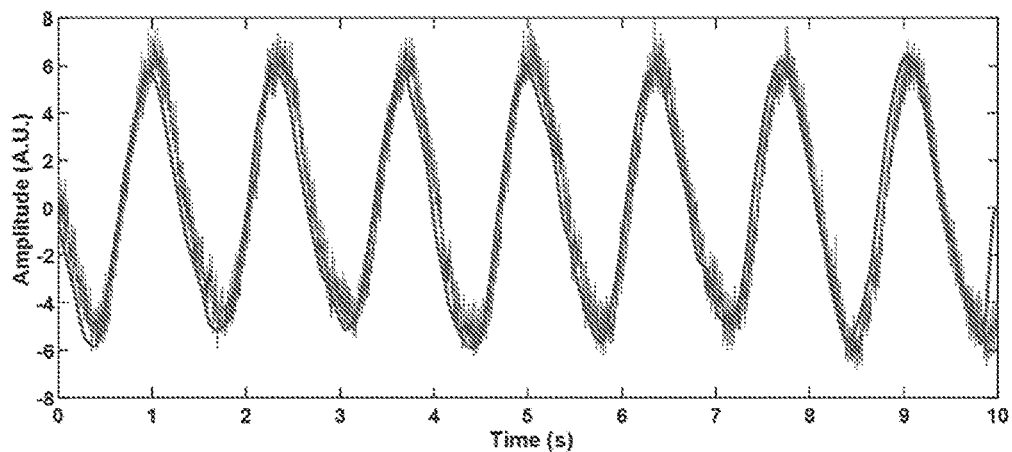
FIG. 15 is a graph showing motor rotation raw data and the curve after band pass filter data by Tag 1.
Figure 16:
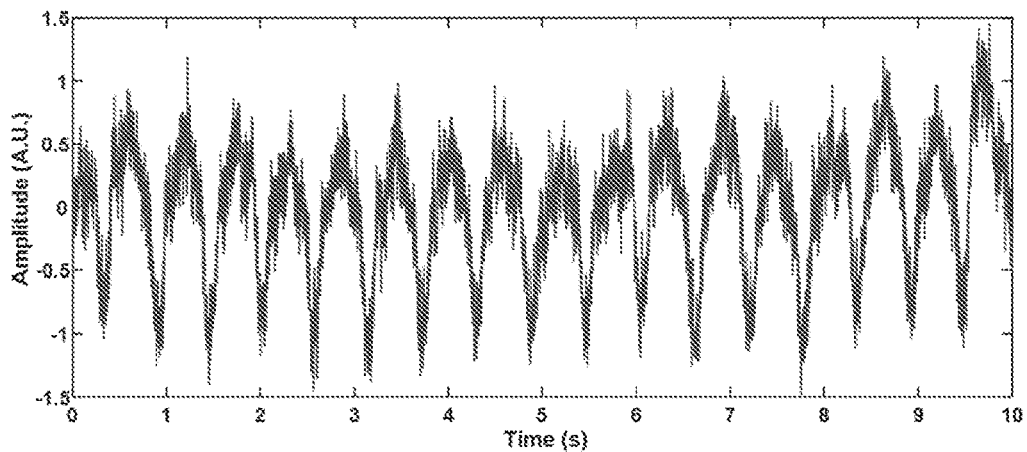
FIG. 16 is a graph showing raw data collected for a heartbeat waveform with sampling frequency at 500 Hz by Tag 2.
Figure 17:
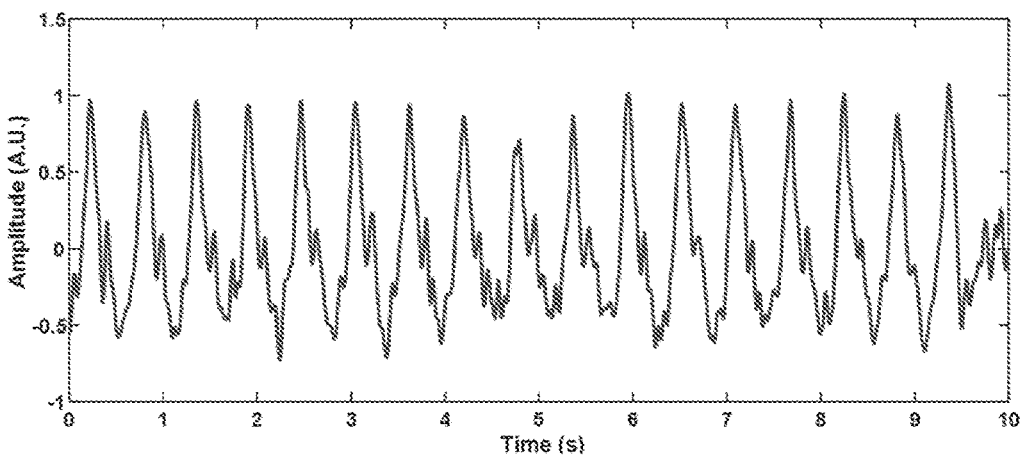
FIG. 17 is a graph showing the heartbeat waveform after band pass filtering of 1.4 Hz-15 Hz extracted from FIG. 16.
Figure 18:
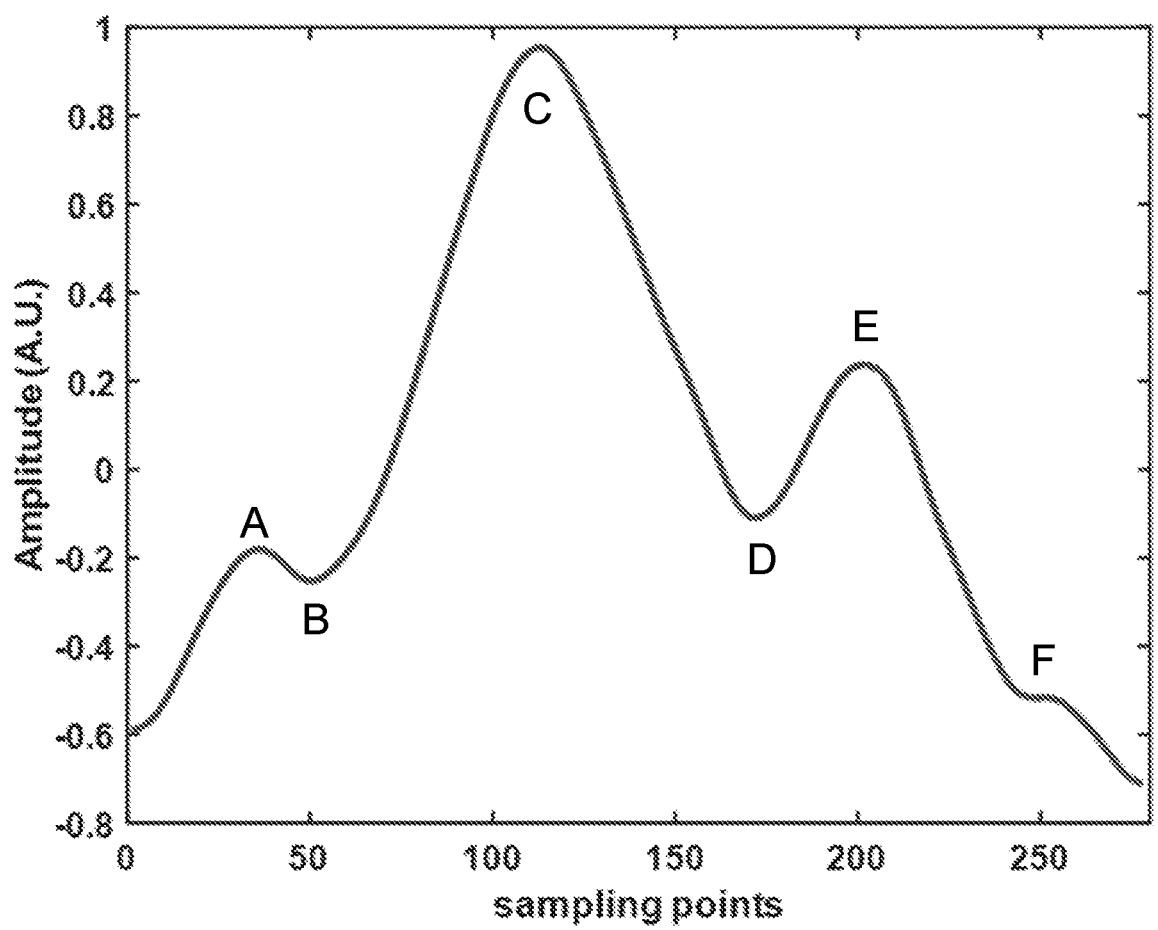
FIG. 18. One cycle of the heart beat waveform extracted from FIG. 16 (around the tick mark of 3s), with the characteristic points illustrated.

In another experiment, a first tag according to an embodiment of the present disclosure (Tag 1) was placed outside of a known motor with a known rotation, and a second tag (Tag 2) was placed within the heart area outside the shirt of an individual under test. The collected waveform from the motor (Tag 1) is shown in FIG. 15, which serves as verification or calibration. The collected waveform from the chest (Tag 2) is shown in FIG. 16. After applying a simple bandpass filter between 1.4-15 Hz, the heart motion waveform in FIG. 17 was obtained. A specific waveform at around three second is magnified in FIG. 18, where the main motion feature was captured by including the characteristic points A-F. For example, point C indicates the main systolic motion, and point E indicates the shockwave recoil after the closing of the aortic valve.

Figure 19:
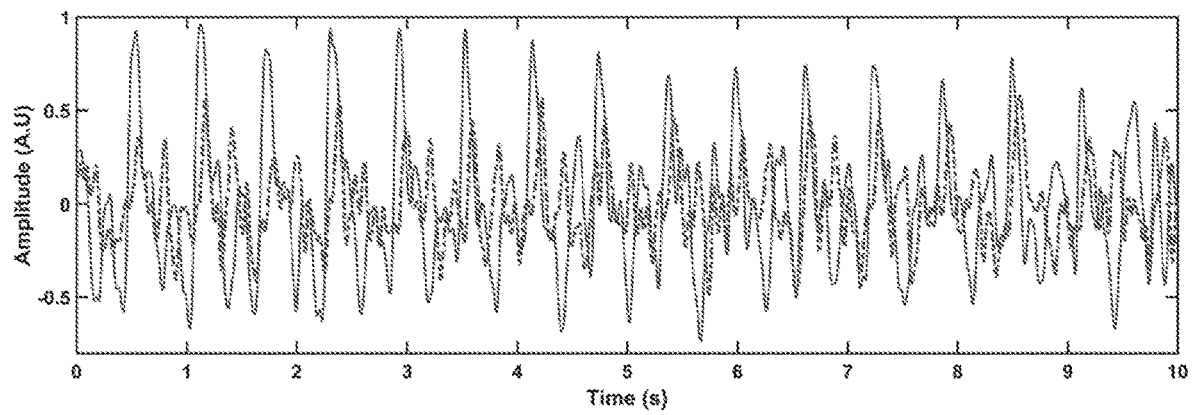
FIG. 19 shows a signal recorded from a chest tag (solid line) and from the wrist tag (dashed line). The timing difference gives an estimate of the blood pressure.
Figure 20:
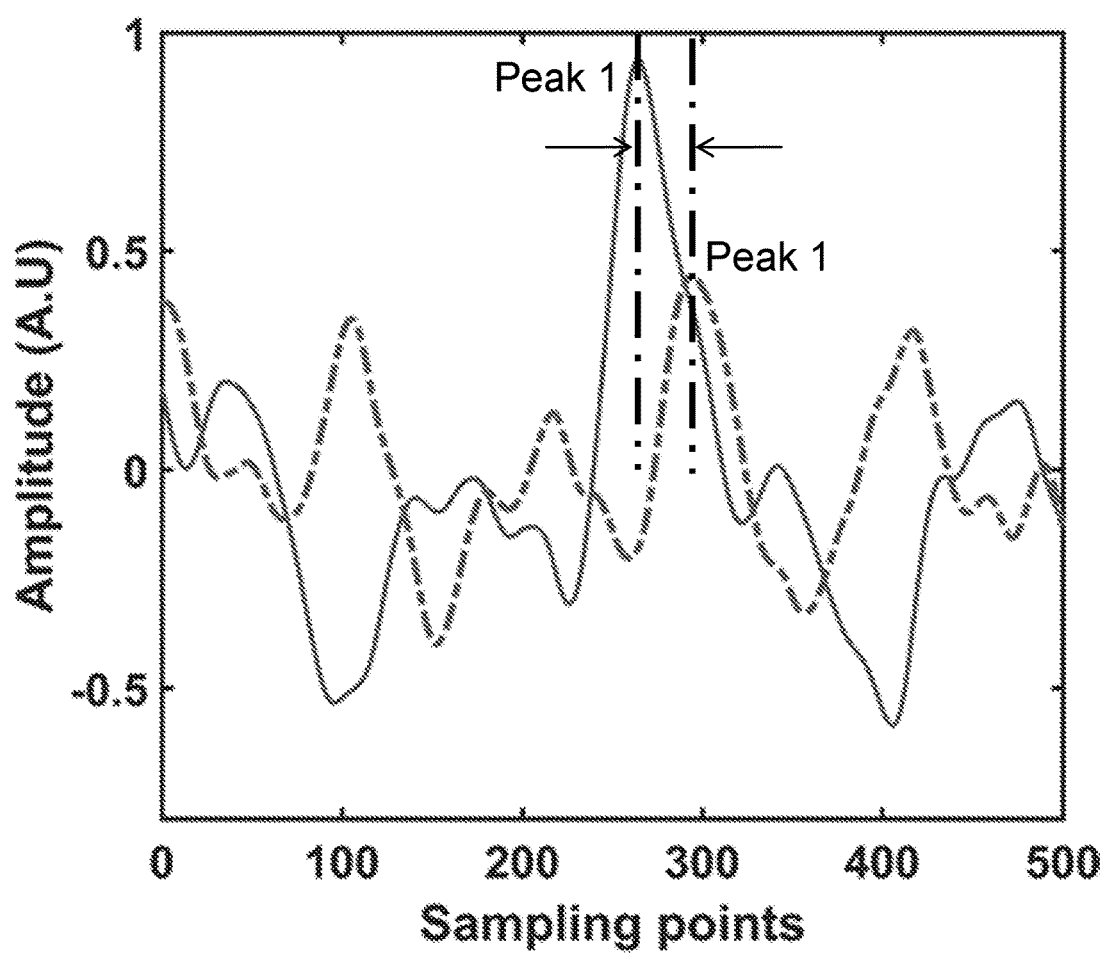
FIG. 20. One cycle of the heart beat waveform and wrist pulse waveform extracted from FIG. 17 (The cycle at 3 s), with the two C peak points illustrated. The delay between Peak 1 and Peak 2 is about 0.074 s, which translates to the diastolic blood pressure around 88 mmHg.

In another experiment, Tag 1 was placed near the chest area and Tag 2 near the wrist of the same person, and the resulting filtered waveforms are shown in FIG. 19. The segment around three seconds is magnified in FIG. 20, where the time delay of the main peaks (point C) of the two waveforms can be used to give an estimate of the blood pressure using known techniques. There are 35 sampling point between Peak 1 and Peak 2, and the interval is about 0.074 seconds with a sampling rate of 470 Hz, resulting in a diastolic blood pressure of approximately 88 mmHg. Averaging the determined blood pressure estimates (obtained, for example, at every heartbeat) can improve the reliability of the estimate.

Accurate Extraction of Heartbeat Intervals

Continuous monitoring of vital signs including heart rates, blood pressures, respiration rates and breath efforts is critical for eHealth. Previous approaches are limited in accuracy, convenience, and sensing capabilities. Some methods such as electrocardiogram (ECG) are difficult for long-term applications due to the requirement of direct skin contact, which is uncomfortable to wearers, restricts body motion and disrupts circadian rhythms. Meanwhile accurate measurement of the inter-heartbeat timing features is important for wellness monitoring and human emotion studies.

For the existing systems, the electrocardiogram (ECG) is the most popular method for heartbeat monitoring, which uses the body electrodes to gather the body potential through small skin currents induced by heartbeats. To achieve good signal quality, the electrodes need to be in direct skin contact by uncomfortable conductive gel and hair removal. For further noise reduction, large electrodes with nonpolarizable Ag/AgCl surfaces are required. Moreover, when frequent hair removal is not practical in animal testing, subcutaneous electrodes are inserted, which poses not only additional measurement difficulty but also infection concerns. Infection can change the homeostasis condition, which may severely bias the vital-sign measurements. The photo-plethysmography (PPG) is broadly used for the pulse rate in both hospitals and wearable devices. PPG utilizes the periodical changes in optical absorption of oxyhemoglobin levels to modulate the intensity of the semiconductor laser, and its signal needs to be heavily processed to retrieve the clear vessel pulse waveforms when detailed information is often lost. Furthermore, as limited by the laser penetration depth, accurate measurement of heart rates and heart rate variability (HRV) is still challenging, and even the small relative body movement to the laser beam causes severe deviation. Acoustic methods, such as the stethoscope-based phonocardiogram (PCG) and ultrasound-based echocardiogram, share similar problems. The transducer size disrupts comforts and limits continuous monitoring by wearable methods. The distortion of the acoustic wave in the tissue, although can be compensated by body-fat dependent post processing, also degenerates the signal quality. Other vital signs such as respiration rates/efforts and blood pressures are usually measured by the pressure or strain gauges, but the discomfort from the belt or cuff discourages long time usage.

A conventional RF method impinges an RF beam to the chest area, and the far-field electromagnetic (EM) wave is backscattered by the body surface. The respiration and heartbeat signals are modulated on the EM wave to be detected by the receiver. Sensing at the far field causes some disadvantages: (1) The dielectric constant difference between the air and human tissue causes strong reflection on the skin surface, which means the respiration signal is much stronger than the signal from inside of the body. The strong respiration signal can overwhelm the heartbeat signal whose signal-to-noise ratio (SNR) and waveform details can be severely degraded due to limited amount of energy and small geometrical average. (2) The conventional method often lacks in multi-channel or multi-point sensing, which limits its practical applicability. (3) From the RF transceiver point of view, the transmitting and receiving bands overlap each other, where self-interference can deteriorate system performance. Due to the above problems, it is difficult for the conventional RF vital-sign sensing system to accurately measure the heartbeat waveform or intervals.

In contrast, the presently-disclosed NCS method modulates the mechanical motions on the surface of the body and beneath the skin tissues within the RF near-field range onto multiplexed harmonic RFID (RF identification) backscattering signals with unique digital identification (ID). In NCS, the respiration signal is well isolated from that of the heartbeat with higher RF energy coupled with the beating heart. The Tx and Rx signals are widely separated by harmonic backscattering, which improves SNR and offers multiplexing by tag ID. With this improved signal quality of the heartbeat, as well as further spectral equalizing for high-frequency components to reduce the sampling jitter, accurate heartbeat intervals can be reliably measured.

Exemplary Implementation

To implement NCS experimentally for heartbeats, the sensing antenna is placed close to the chest area. The conventional RF transponder with the fully functional transceiver will need active power from battery or power lines, which limits the long-term monitoring capability due to concerns of size and convenience. A passive and maintenance-free wearable device is preferred. The UHF RFID system is a good candidate. The RFID scheme is shown in FIG. 8A. The reader transmits the downlink signal at the frequency off where the transmitter (Tx) signal also goes through the circulator to the reader antenna. The downlink signal is received by the tags complied with the Electronic Product Code (EPC) protocol. The tags do not need any active power source, because they use the energy in the downlink RF signal to power up. The charge pump on the tag harvests the small RF energy received by the tag antenna, then the logic circuits modulate the backscattering uplink signal. The uplink signal is then received by the reader receiver (Rx) antenna, and goes through the circulator. However, a few issues will limit the system performance for the NCS purpose. (1) There is strong self-interference directly from downlink to uplink. As shown in FIG. 8A, because of the insufficient isolation of the circulator, the direct Tx antenna reflection, and the ambient reflection from nearby objects, strong Tx-to-Rx leakage persists. Due to the low modulation rate of the passive tag, the Rx signal suffers large noises from the Tx phase noise skirt, which limits the SNR and reader sensitivity. (2) The conventional RFID system often employs the circulator as the Tx/Rx duplexer, which has limited bandwidth and is hence vulnerable to the indoor multipath interference. (3) The conventional EPC protocol utilizes time division multiple access (TDMA) to handle tag collision, where the tag chooses a random delay time in the Aloha scheme. This random delay introduces extra aperture jitters to the sensing signal, which further degenerates SNR and causes signal distortion.

To solve all these problems, a harmonic RFID system may be used. As shown in FIG. 8B, the Tx signal is at f, transmitting through the low pass filter (LPF) to the Tx antenna. The harmonic tag is powered up by the downlink RF signal, and backscatters the harmonic signal at 2f in the uplink through the Rx antenna and the high pass filter (HPF). The Tx and Rx spectra are well separated, and the Rx signal is hardly affected by the Tx phase noise skirt. The reader RF front end uses LPF and HPF as the duplexer, and the bandwidth can be broader for indoor multipath immunity. Meanwhile the harmonic tag can also run on the CDMA protocol, which is synchronized by the reader to provide multi-tag access with minimal aperture jitter.

The schematic of the harmonic tag is shown in FIG. 22A. Antenna 1 receives the downlink signal from the reader. A part of the signal is delivered to the energy harvesting module to power up the tag control circuits, and the tag receiver demodulates the downlink command to conduct the appropriate air protocol and the corresponding logic operations. The other part of the RF energy is coupled to the nonlinear transmission line (NLTL) to generate the 2nd harmonic signals in the uplink, which is modulated by the RF switch radiated through Antenna 2. FIG. 22B shows a PCB prototype of an exemplary embodiment, on which the digital logic part was modified from the WISP platform.

The Ettus B200 software defined radio (SDR) was programmed as the harmonic RFID reader. The Tx local oscillator (LO) was set at 1 GHz and Rx LO at 2 GHz with the same clock source to maintain the coherent harmonic transceiver scheme.

Figure 23:
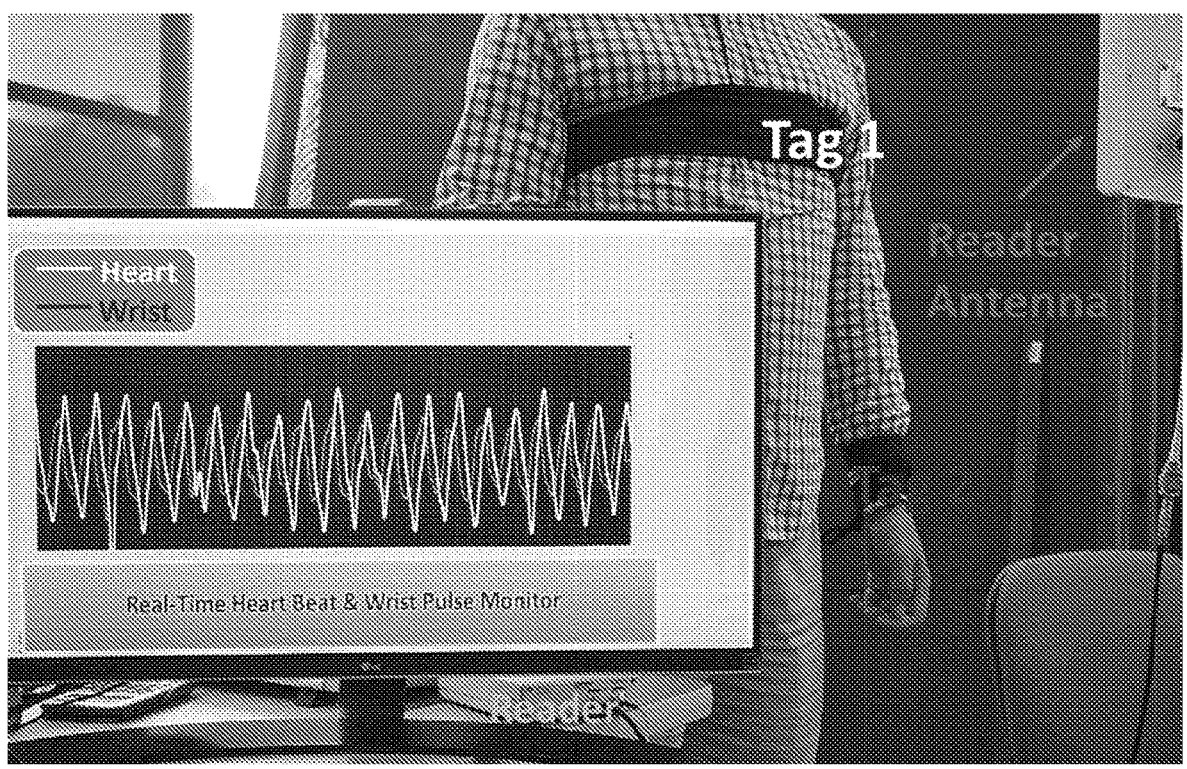
FIG. 23 is a photograph showing an experimental NCS setup. A first tag is in the chest area and second tag is on the left wrist. The sensing waveforms are shown on the screen. The chest and wrist bands are here just for deployment convenience. No skin touch or band tension is needed.
Figure 24A:
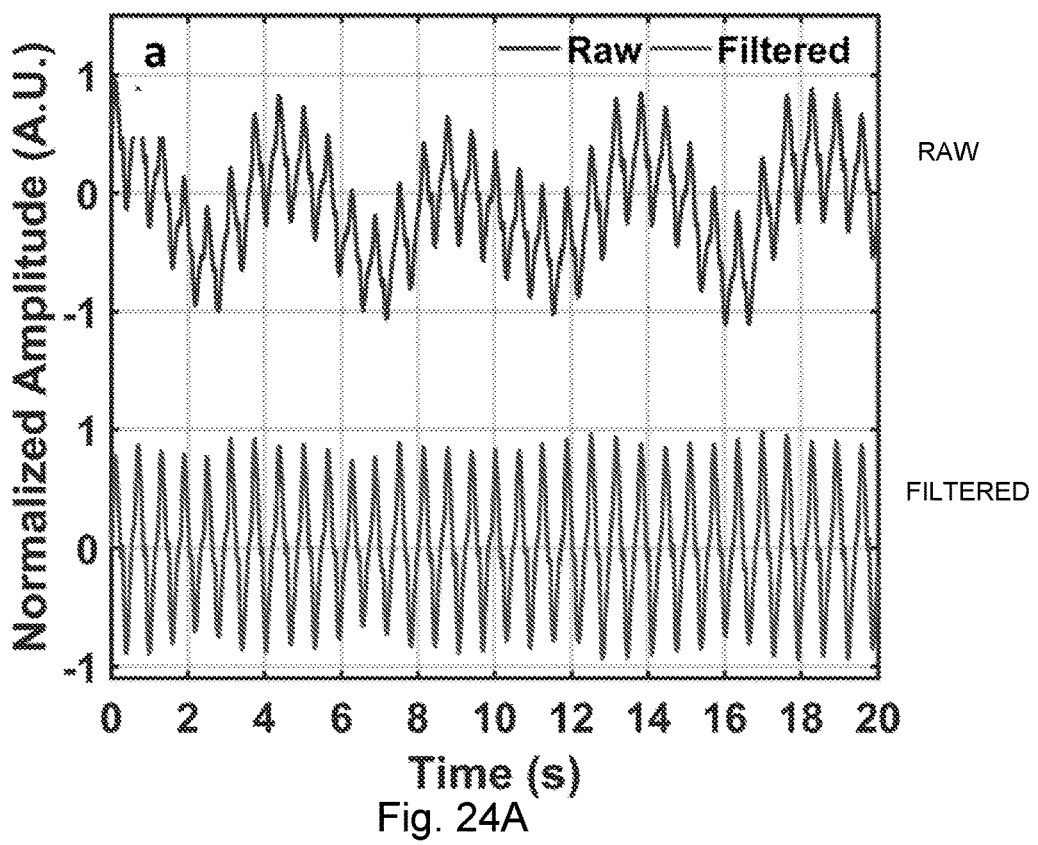
FIGS. 24A-24B. The heartbeat and breath waveforms extracted from the chest-tag NCS signal. (A) The amplitude of the NCS signal is mainly modulated by the heartbeat. The top curve is from the normalized amplitude, which passes through digital BPF (0.8-15 Hz) to give the bottom curve. (B) The phase of the NCS signal is mainly modulated by the breath motion. The top curve is the normalized raw phase, which passes through digital BPF (0.1-1.2 Hz) to give the bottom curve. Isolation between the amplitude and phase modulation in the quadrature receiver renders unambiguous separation between breath and heartbeat waveforms.
Figure 24B:
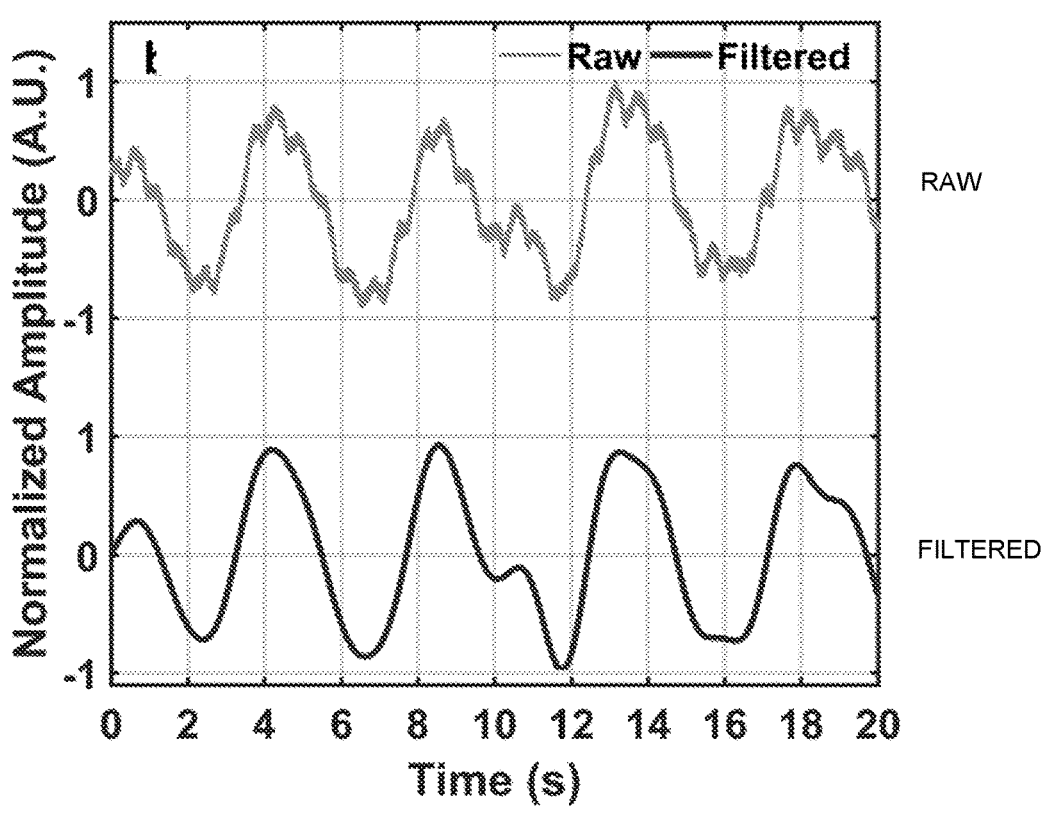

An exemplary vital-sign monitoring setup is shown in FIG. 23. A first tag is in the chest area sensing the heartbeat and respiration, and a second tag is on the left wrist sensing the pulse. The chest and wrist bands are just for convenient tag deployment on the garment with no requirement of skin touch or elastic band tension. The tags receive the downlink signal from the SDR reader and backscatter the uplink signal to the reader antenna. The demodulated NCS signal is processed by the LabVIEW and shown on the screen, where the white curve traces the heartbeat and the red curve traces the wrist pulse. The waveforms are processed by the bandpass filter (BPF) with 0.8 to 15 Hz. The delay from the heart signal to the pulse signal is the pulse transit time (PPT), which can be used to estimate the blood pressure. FIGS. 24A and 24B show the demodulated NCS signals of heartbeat and respiration collected from the chest RFID tag. The upper curve in FIG. 24A is the normalized amplitude part of the NCS signal. One can see that the major modulation is the heartbeat, although the breath is slightly coupled. Isolation between the amplitude and phase modulation in the quadrature receiver gives unambiguous separation between the breath and heartbeat waveforms, as illustrated in the interferometer analogy. After the digital BPF (0.8 to 15 Hz), the heartbeat signal is clearly retrieved as the lower curve. FIG. 24B is the normalized phase part of the NCS signal. The raw phase waveform is shown as the upper curve, where the major modulation is the breath although the heartbeat is slightly coupled as well. The raw phase data are processed by the digital BPF in a different range (0.1 to 1.2 Hz) to retrieve the filtered breath signal in the crimson curve. Instead of relying solely on band filtering in previous works to separate the breath and heartbeat signals, NCS can discriminate external and internal mechanical motions by the quadrature scheme.

Accurate Extraction of Heartbeat Intervals in an Exemplary Embodiment

Figure 25A:
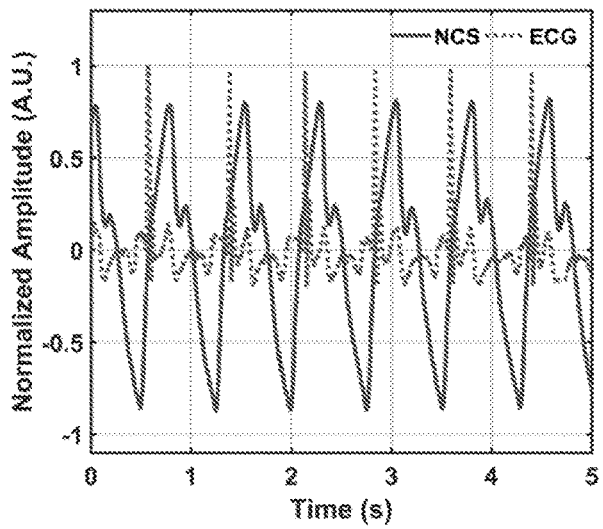
FIGS. 25A-25C. (A) The synchronized time-domain NCS (solid line) and ECG (dotted line) heartbeat signals. The sampling rate of the NCS is 5,000 Sps, and ECG originally has 512 Sps but up-sampled to 5,000 Sps. (B) The spectrum of the NCS signal, where the intensity is normalized to the peak value around 1 Hz and zoomed in to clearly show the lower intensity part. (C) The spectrum of the ECG signal, where the intensity is also normalized to the peak value around 1 Hz and zoomed in to show the lower intensity part. High frequency components between 2 Hz and 8 Hz is more prominent than those in NCS.
Figure 25B:
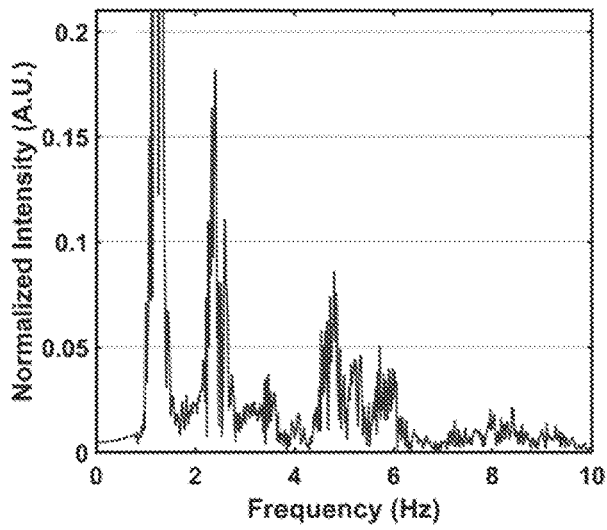
Figure 25C:
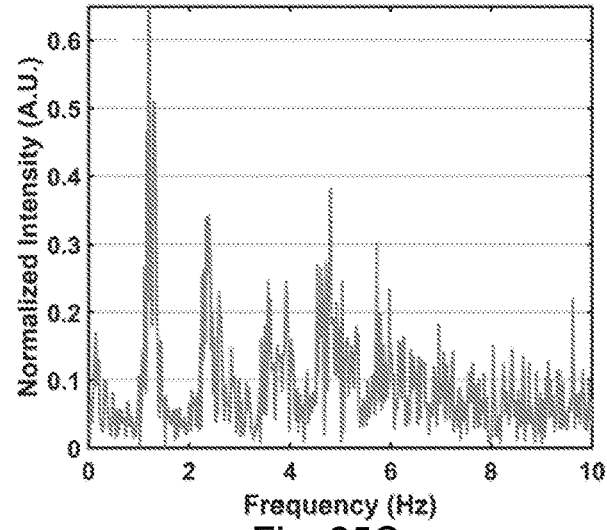

To measure the heartbeat interval, the waveform and the associated peak-to-peak time may be precisely detected. The timing accuracy hence depends on the time resolution and the sharpness of the feature points. The sharp edges or peaks in the time domain are better reflected by the high frequency components in the spectrum. However, the low-frequency components from the breath and the main ventricular motion naturally have much larger amplitude and can thus overwhelm the sharp peaks for accurate interval detection. As shown in FIG. 25A, the solid curve is the NCS heartbeat signal and the dotted curve is the ECG signal, which is synchronized in the SDR reader as the master link. The sampling rate of the NCS is 5000 samples per second (Sps), and that of ECG is 512 Sps, originally limited by the electrode noises. The ECG signal is up-converted to 5000 Sps for synchronization and graphical display. To measure heartbeat intervals by ECG, we can use the peak of the QRS complex in each period. Because the peak is already sharp, its timing can be easily located. However, the NCS signal measures the mechanical motion directly and is hence smoother without clear peaks, which decreases the peak detection accuracy. To retrieve the accurate timing, the sharp-peak feature points are needed. Therefore, the original NCS signal has to be further processed to improve the peak detection certainty. FIGS. 25B and 25C show the spectra of the synchronized NCS and ECG signals. Both spectra are normalized to the respective peak intensity value around 1 Hz. In comparison with the NCS signal, ECG has much stronger high-frequency (2-8 Hz) components and has therefore sharper peaks. However, because of the direct motion modulation, harmonic backscattering design and higher sampling rate in NCS, the noise floor is much lower than that of ECG. Nevertheless, the frequency components of both spectra are reasonably aligned and share the similar distribution, due to the synchronous measurements of the same heartbeat source.

Figure 26A:
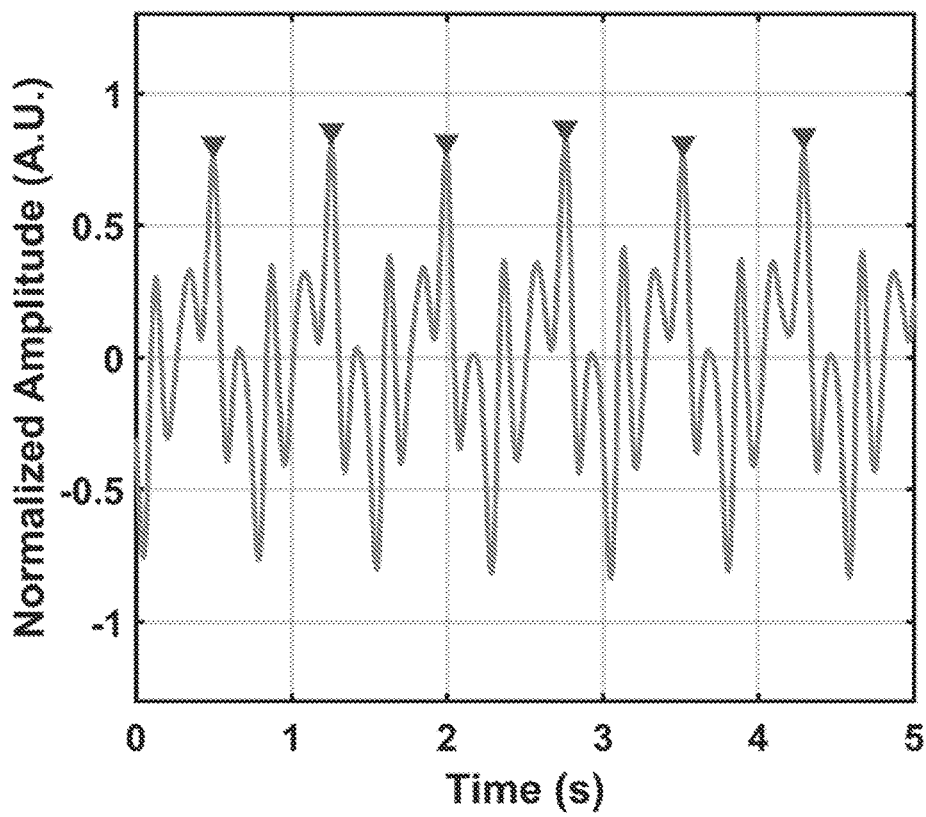
FIGS. 26A-26B. (A) The time-domain NCS signal after the high frequency equalization. The triangular markers show the sharp peak feature points for heartbeat interval extraction. (B) The heartbeat intervals of NCS and ECG signals. The dashed line, the dotted line and the solid line are from the original NCS (NCS1), ECG, and equalized NCS (NCS2), respectively.

The NCS signal has rich high-frequency components around 4.5 to 6 Hz, but the intensity amplitude is at least 10 dB lower than the main heartbeat signal which is around 1 Hz. In comparison, ECG also has those components but with higher spectral intensity and noise. Therefore, a straight-forward spectral equalization may be applied: A 4 Hz-7 Hz bandpass finite impulse response (FIR) filter is applied to the original signal, and then the output of the filter is amplified by 13 dB, which is added back to the original signal. In order to make these two signals time domain aligned, the filter may be designed as the zero-phase filter to eliminate the phase delay. The FIR structure is advantageously used to keep the linear phase-frequency response. The processed signal is shown in FIG. 26A, which has more feature points and sharp peaks in comparison with the original signal for each heartbeat cycle. The highest-peak feature point of each heartbeat cycle is selected as the timing indicator, shown as the triangular markers in FIG. 26A.

Figure 26B:
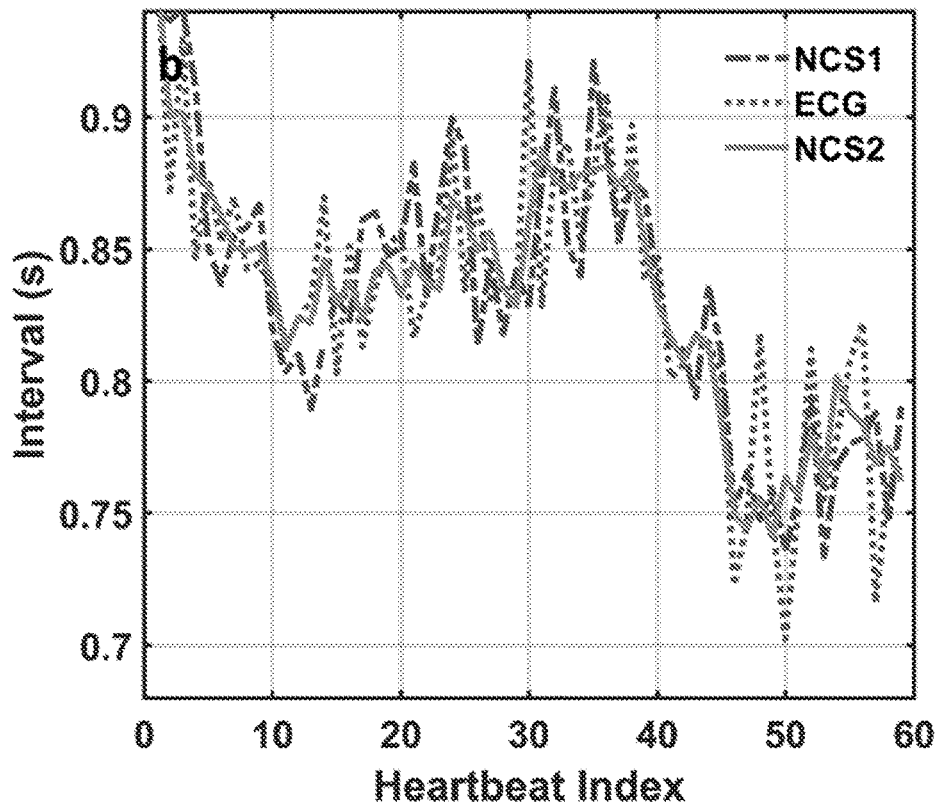

The heartbeat interval is defined as the time between the feature points in one cycle and the next cycle. The heartbeat intervals are shown in FIG. 26B. The heartbeat intervals are calculated for the original NCS (dashed line), ECG (dotted line), and the equalized NCS (solid line) signals. For the original NCS and the ECG signals, the feature points are chosen as the highest positive peaks. Because the heartbeat interval is calculated based on the beat-to-beat time, the horizontal axis is the heartbeat index instead of time. The vertical axis is the heartbeat interval, and its reciprocal can be regarded as the heartrate. All three curves show the same overall decreasing trend, or equivalently the increasing heart rate, as the measurements right were taken after body exercise. Although the ground truth is not provided here, the following observation can still be made. In comparison with the equalized NCS heartbeat interval, the original NCS has larger variation due to inaccurate peak detection; the ECG signal has larger variation due to the low sampling rate of 512 Sps. The more stable heartbeat interval variation in equalized NCS within a few heartbeats makes physiological sense.

Torso Antenna Impedance Effects

Antenna effects on NCS performance were analyzed with associated antenna design strategy. When better antenna impedance matching is reached, the energy coupling efficiency and SNR may be improved to detect the cardiogram waveform details.

Antenna Impedance Matching in NCS

Figure 27A:
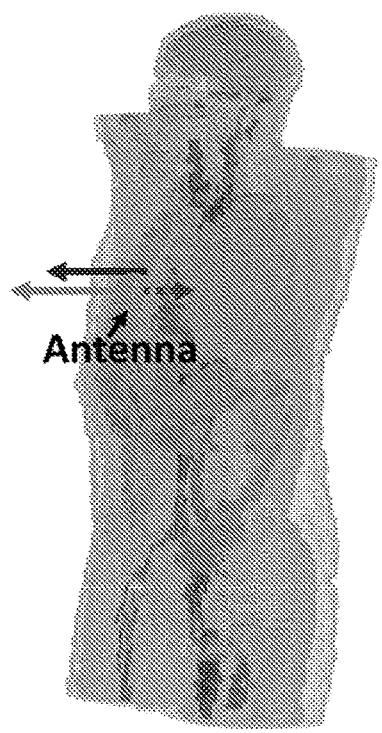
FIGS. 27A-27B. NCS antenna effects: (A) The EM simulation model by a chest RFID tag in CST Microwave Studio. (B) Simulated $S_{11}$ parameter for the tag antenna.

To demonstrate the operational principle of NCS, a human torso electromagnetic (EM) simulation model is built in CST Microwave Studio, as shown in FIG. 27A. The organ geometry and tissue property of the torso are extracted from the Zubal Phantom. The sensing antenna was attached close to the chest area but does not need to touch the skin. The emitted EM wave transmits partially to the far field, shown as the gray arrow. Another part of the RF energy is coupled into the body due to the near-field effect, shown as the dashed arrow. The phase of the backscattered signal is modulated by the heartbeat because of the movement of the dialectic boundaries. The modulated backscattered RF signal shown as the black arrow interferes with the direct transmission (gray arrow) and is received by the RF receiver. Because these two signals are from the same source with different paths, the operation is similar to an interferometer structure. The internal heartbeat gives the differential modulation of the two signals, and can be demodulated from the far-field RF magnitude. Meanwhile the chest external movements caused by respiration or body motion will change the phase delay of both signals (gray and black arrows) which can be regarded as the common-mode modulation, and can be demodulated from the far-field RF phase. The magnitude and phase information at the receiver can be readily and accurately separated by the quadrature mixer.

Figure 27B:
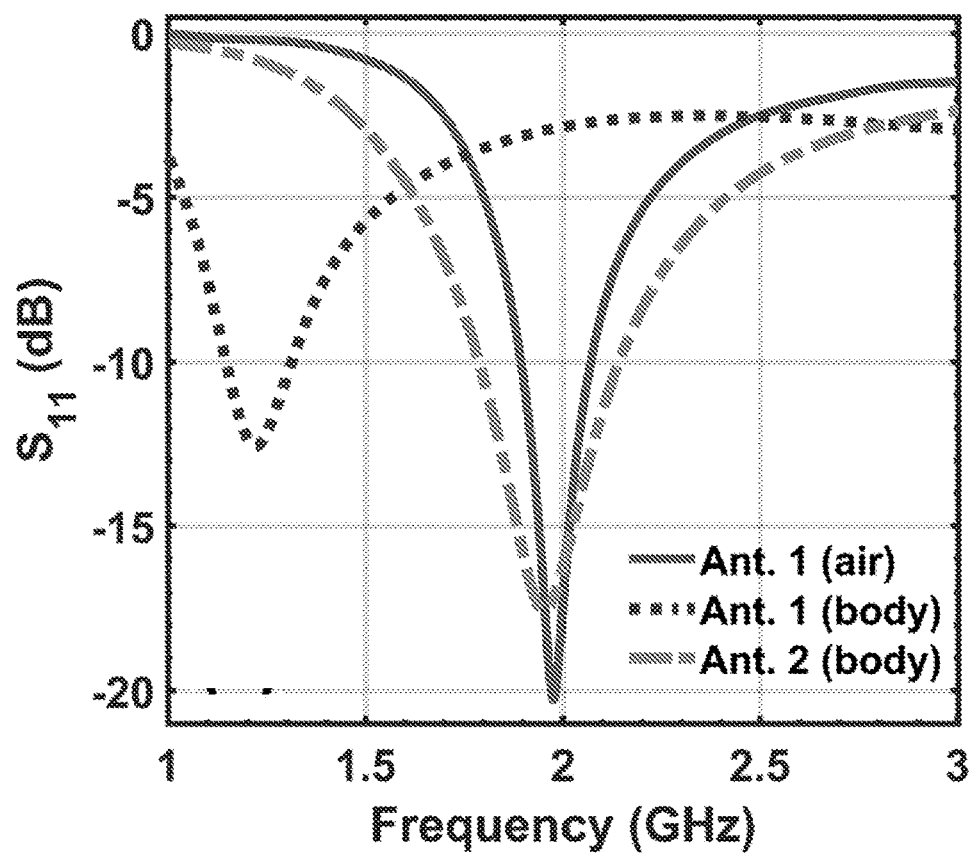

A part of NCS is the sensing antenna close to the external and internal body motion. Because of the high dielectric constant of the human tissue in the near-field region of the antenna, its S parameter will change significantly. From the design point of view, the antenna can be considered as the matching component between the RF circuit impedance (often around 50Ω) to the impedance of the joint region consisting of the free space and the torso, the latter of which will change the impedance, frequency response and radiation pattern in comparison with the antenna in only the free space. For the CST simulation in FIG. 27B, $S_{11}$ of a 2-GHz dipole antenna is shown as the solid line when the antenna operates in the free space. However, when that antenna is attached near the chest area, $S_{11}$ will be shifted to the dotted line, which means the frequency near 2 GHz can no longer have good emission efficiency due to high reflection. There are two possible simple solution strategies: Shift the operation frequency to the band with low $S_{11}$ or redesign the antenna geometry to fit the original 2 GHz band. The dashed line is the redesigned antenna, which is matched with the torso presence. The reflection at 2 GHz is improved greatly from ~3 dB to ~18 dB.

Figure 28A:
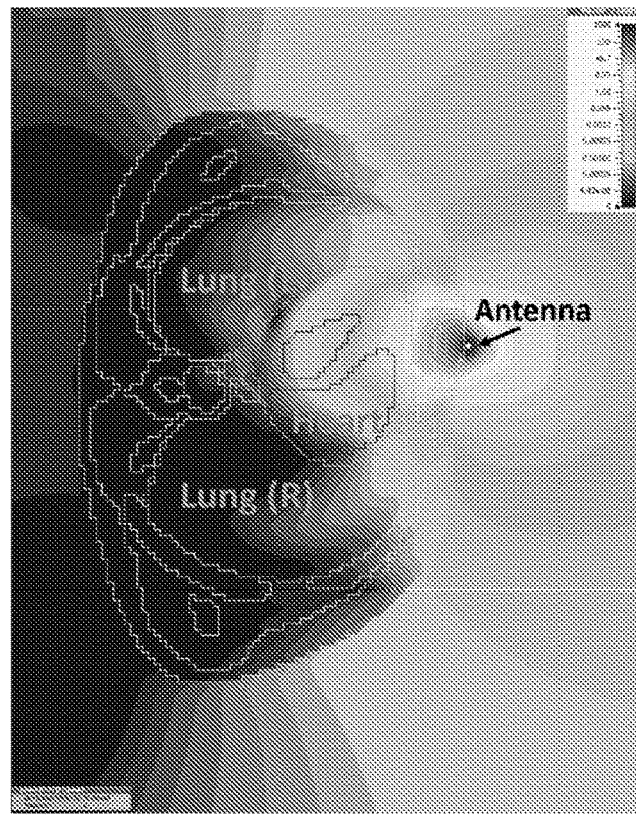
FIGS. 28A-28B. The simulated EM power flow at 2 GHz of the NCS signal coupled into the human torso with (A) poor impedance matching, and (B) with proper impedance matching.
Figure 28B:
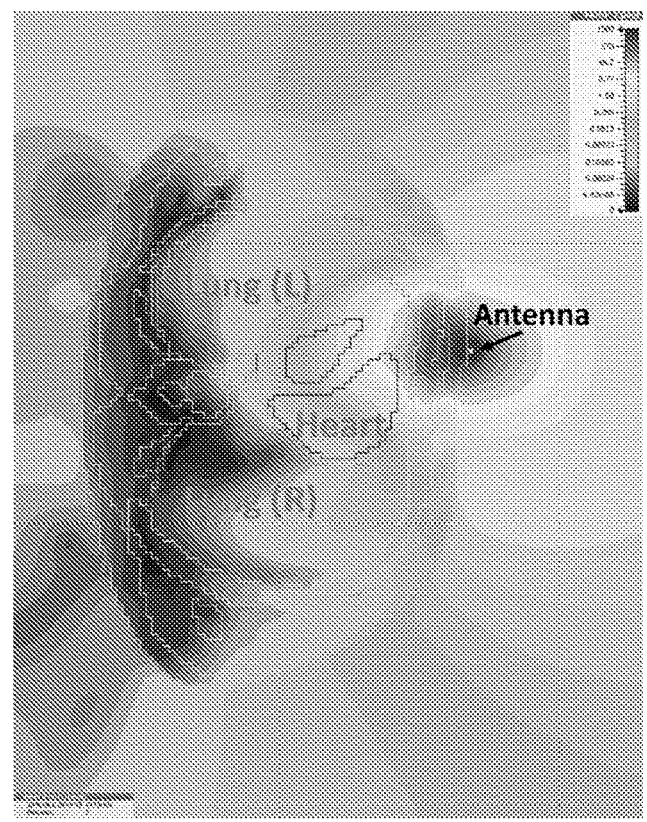

To further investigate the performance of the antenna matching effects, FIG. 28 shows the power flow at 2 GHz when an antenna is placed on the chest in FIG. 28B. In FIG.

28A, the original Antenna 1 of the dotted line, and FIG. 28B the revised Antenna 2 of the dashed line. The cross sections of the human torso are illustrated with the left (L) lung, right (R) lung, and the heart. Under the same driving signal strength and color contour scales, one can observe that the energy coupling to the torso from the non-matched antenna in FIG. 28A is much smaller than that of the matched situation in FIG. 28B. The stronger energy coupling also increases the total strength of the backscattered signal. Hence, with the same noise floor, SNR and the sensing sensitivity will be both improved.

Experiment and Analysis

To implement NCS on a convenient and high-performance sensing platform in an exemplary embodiment, a harmonic backscattering RFID system was utilized. The NCS antenna was part of the harmonic tag whose schematic is shown in FIG. 22A. The tag was designed as the passive device harvesting the downlink RF energy from the reader to power up the tag circuits. Part of the RF energy received by Antenna A (Ant. A) was harvested by the charge pump to operate the receiver and the microcontroller unit (MCU). The other part of the RF energy was coupled into the nonlinear transmission line (NLTL) for the second harmonic generation to be backscattered to the reader through antenna B (Ant. B). The RF switch modulated the harmonic signal with on-off keying (OOK) as the uplink baseband. The code-division multiple-access (CDMA) protocol was performed on the tag MCU to achieve better synchronization and performance in the multi-tag scenario. FIG. 22B shows the printed circuit board (PCB) prototype for the exemplary harmonic tag, where the NCS sensing antenna was mounted to the Ant. B connector. The uplink RF signal from Ant. B was also modulated by the breath and heartbeat, then received and demodulated by the reader. The harmonic reader was implemented by the software defined radio (SDR, Ettus B200). The local oscillator (LO) of the reader transmitter (Tx) was set at the fundamental frequency f, and the receiver (Rx) LO was set at the 2nd harmonic frequency of 2f. The two synthesizers of Tx and Rx LOs were driven by the same frequency reference, so the reader was configured as the harmonic coherent transceiver. A major benefit of using the harmonic backscattering instead of the conventional RFID system was the broad frequency separation of the downlink and the uplink, so the weak backscattering signal from the tag did not suffer from the high phase-noise skirt from the Tx leakage. Therefore, the sensitivity and SNR can be much higher than the conventional RFID scheme.

The NCS measurement setup is shown in FIG. 23. One tag was in the chest area for the heartbeat and respiration, and the other on the left wrist for the pulse. The chest and wrist bands were there for convenient tag deployment on the garment with no requirement of skin touch or elastic band tension. The tags received the downlink signal from the SDR reader and backscattered the uplink signal to the reader. The demodulated NCS signals were processed by the bandpass filter (BPF) of 0.8 to 15 Hz in LabVIEW and shown on the screen, where the white curve traced the heartbeat and the gray curve traced the wrist pulse. The delay from the heart signal to the pulse signal is the pulse transit time (PPT), which can be used to estimate the blood pressure. The reader antenna currently can be 1.5 to 3 meters away from the person, which was limited by the RF power harvesting and the passive harmonic conversion loss. The range can be readily improved by the custom designs of the reader and tag.

Figure 29A:
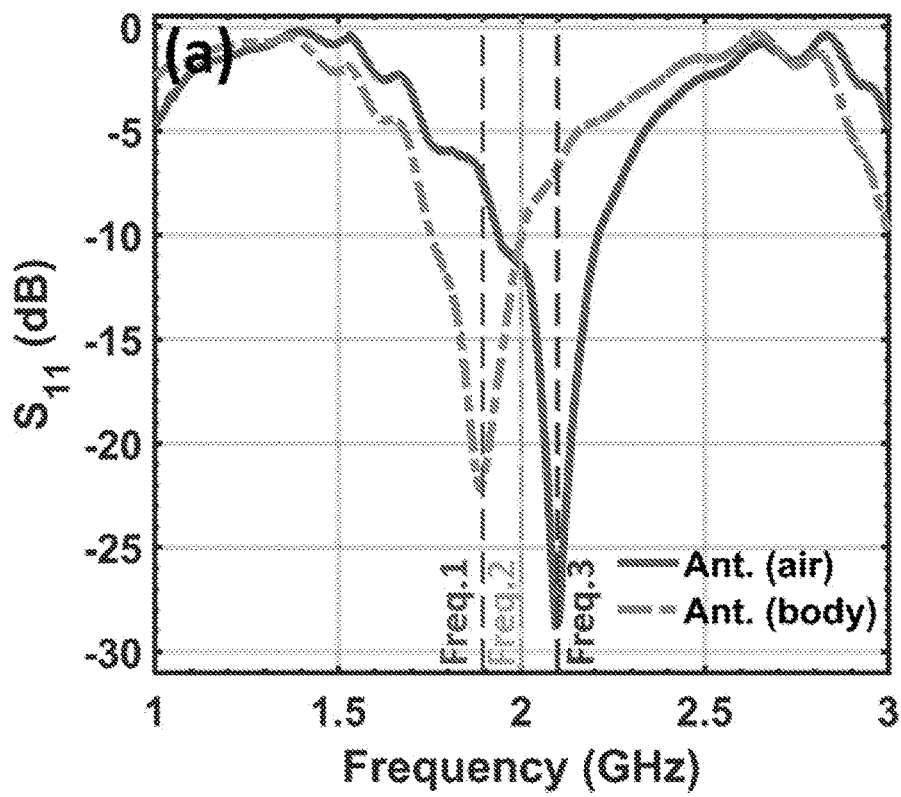
FIGS. 29A-29B. The experimental results in various frequencies. (A) $S_{11}$ of the NCS antenna when it is operated in air (the solid curve), and placed on the chest (the dashed curve). (B) The heartbeat signal waveforms demodulated from the chest tag in FIG. 4 with different sensing frequencies. The NCS signals from the solid curve (impedance matched condition), dashed curve and the dotted curve correspond to Freq. 1, 2, and 3 in FIG. 5A, respectively.
Figure 29B:
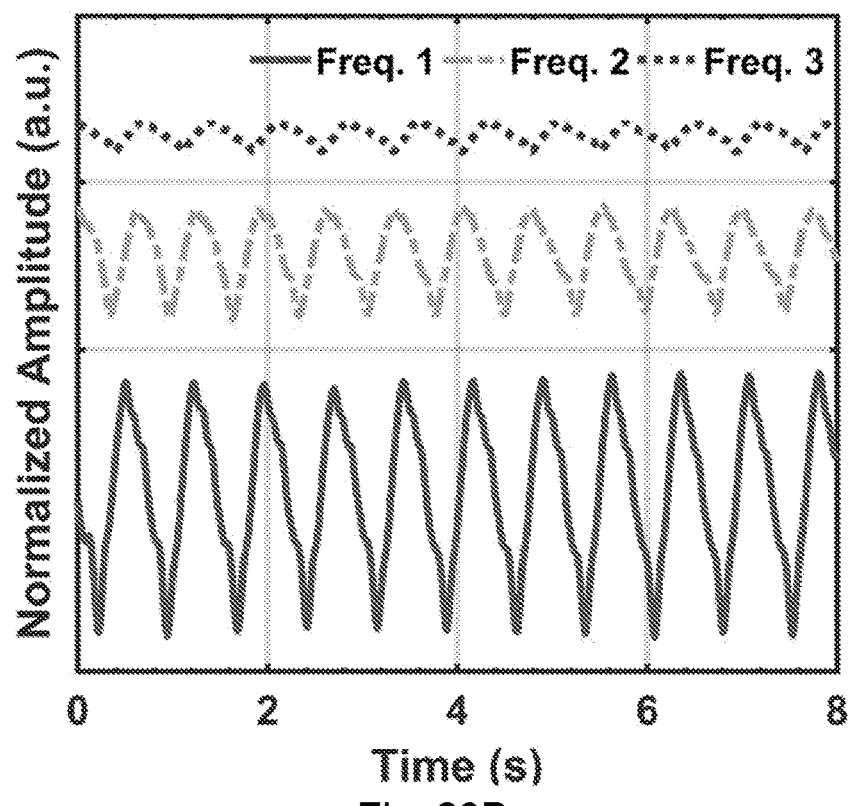

A monopole antenna was used as the sensing antenna for the exemplary embodiment of NCS, whose $S_{11}$ is shown in FIG. 29A as the solid line with the center frequency of 2.1 GHz when the antenna was operated in free space. When the NCS antenna was placed near the chest area, the $S_{11}$ response shifted to the dashed line with the center frequency at 1.9 GHz in FIG. 32A. The reflection around 2.1 GHz is now much higher. To achieve large energy coupling and high SNR in NCS, the downlink signal may be changed to 950 MHz so that the sensing antenna is well matched at 1.9 GHz. As shown in FIG. 29B, the solid line is the heartbeat signal acquired by the uplink at 1.9 GHz (shown as the marker of Freq. 1 in FIG. 29A). The dashed line with the uplink at 2 GHz (Freq. 2 in FIG. 29A) and the dotted line at 2.1 GHz (Freq. 3 in FIG. 29A) have much weaker NCS signals due to less energy coupling into the torso. Notice that the RF radiation efficiency at Freq. 2 and Freq. 3 is still reasonably high, estimated at 90% and 80% at $S_{11}$ of −10 dB and −7 dB, respectively, and therefore most of the degradation in the NCS signal can be attributed to the reduction in tissue coupling. All measurements are conducted under the same system setting and extraction procedure except the different frequencies. Under the same system noise floor, the higher NCS signal strength can increase SNR to recover clearer waveform details. The repeatable details can be observed along the decreasing slope in the well-matched condition of the solid line, which can be hardly seen in the non-matched conditions with the uplink frequencies at 2.0 and 2.1 GHz.

Mitigating Body Movement Interference

In this section, an exemplary NCS vital-sign monitoring system is provided with a mitigation method based on high-frequency heartbeat components to counter interferences from body movement. By calibration with synchronous ECG, a low error probability is experimentally demonstrated in real-time heartrate measurements.

As mentioned above, electrocardiogram (ECG), photoplethysmography (PPG), and acoustic methods such as stethoscope phono-cardiogram and ultrasound echocardiogram are present technologies for measuring the heartrate and its variability, where ECG is most well established as the clinical standard. However, these methods all have serious concerns in the wearable sensing system. To achieve good signal quality in ECG, the electrodes need to be in direct skin contact by uncomfortable conductive gel and hair removal. Although wearable ECG garment had been attempted, it is still difficult for daily apparel. The present PPG device is broadly used on the smart watch, band, patch and clamp on the wrist or fingers, but it needs a tight contact to avoid distortion from ambient light and relative motion. The PPG signal relies on heavy processing to obtain reasonably clear pulse waveforms, and the detailed information in both low and high frequency ranges is often lost. The sensing depth of the oxygen content is limited so that PPG is most often applied to body areas with shallow blood flow in the reflection mode, or high blood concentration in the transmission mode, while direct heart motion measurement is hardly achievable. Stethoscope phonocardiogram is vulnerable to internal noises (breath and voice) and external interference (sound and vibration) and is practical only in a control lab ambient. Ultrasound echocardiogram is difficult to implement as a wearable device, because of its bulky transducer which needs to directly contact the skin surface with impedance-matching gels. In addition, when the simultaneous measurements of the respiration rate/effort and blood pressure are also desirable, the strain gauges are commonly required, but the discomfort from the belt and cuff tension discourages long-term usage, and can also disrupt sleep or circadian rhythms. Several RF-based methods had also been proposed, where an RF beam as the far field was radiated to the chest area to be backscattered by the human body. The respiration and heartbeat signals are both modulated on the RF carrier and then received by the receiver antenna. If the backscattered signal was further modulated by an RFID, it was thought that imminent skin contact be important to reliably retrieve the minute skin movement by breath and heartbeat. If the backscattered signal was not modulated by a digital ID (identification) in the tag-less case, interferences from any other nonspecific backscattering can be detrimental. With or without personal tags, body motion will cause severe inaccuracy in RF-based heartrate estimation.

In this section, an exemplary NCS vital-sign monitoring system is provided with a mitigation method based on high-frequency heartbeat components to counter interferences from body movement. By calibration with synchronous ECG, a low error probability is experimentally demonstrated in real-time heartrate measurements.

Experiment and Analysis

Figure 31:
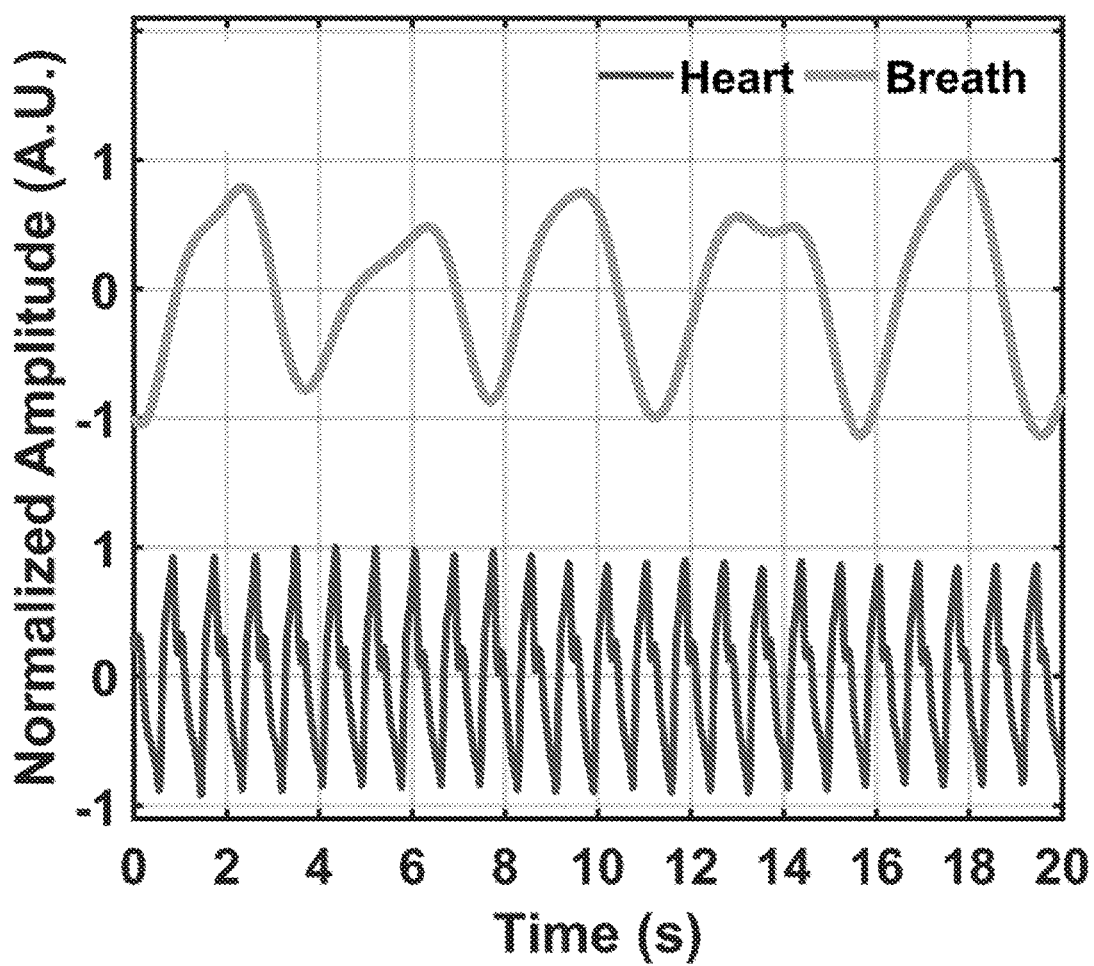
FIG. 31 shows experimental results of heartbeat and breath waveforms extracted from a chest tag using NCS.

An embodiment of the NCS technique was tested using the experimental setup shown in FIG. 23. A software defined radio (SDR, Ettus B200) was programed to act as a harmonic reader. Passive harmonic tags were deployed at the chest and left wrist areas. Chest and wrist bands were used for convenient tag deployment on the garment with no requirement of skin touch or elastic band tension. The NCS (measurement) signal was received by the reader Rx antenna and demodulated by the SDR harmonic reader. The resulting demodulated heartbeat and wrist pulse are shown on the screen as the light and dark curves, respectively. The delay of the wrist pulse with respect to the heartbeat is the pulse transit time ("PTT"), which can be used to estimate the blood pressure. FIG. 31 shows demodulated signals from the chest tag. The heartbeat signal was from the amplitude of the measurement signal after bandpass filtering (BPF: 0.8-15 Hz). The breath signal was derived from the phase of the measurement signal after BPF of 0.1-1.2 Hz.

Figure 32A:
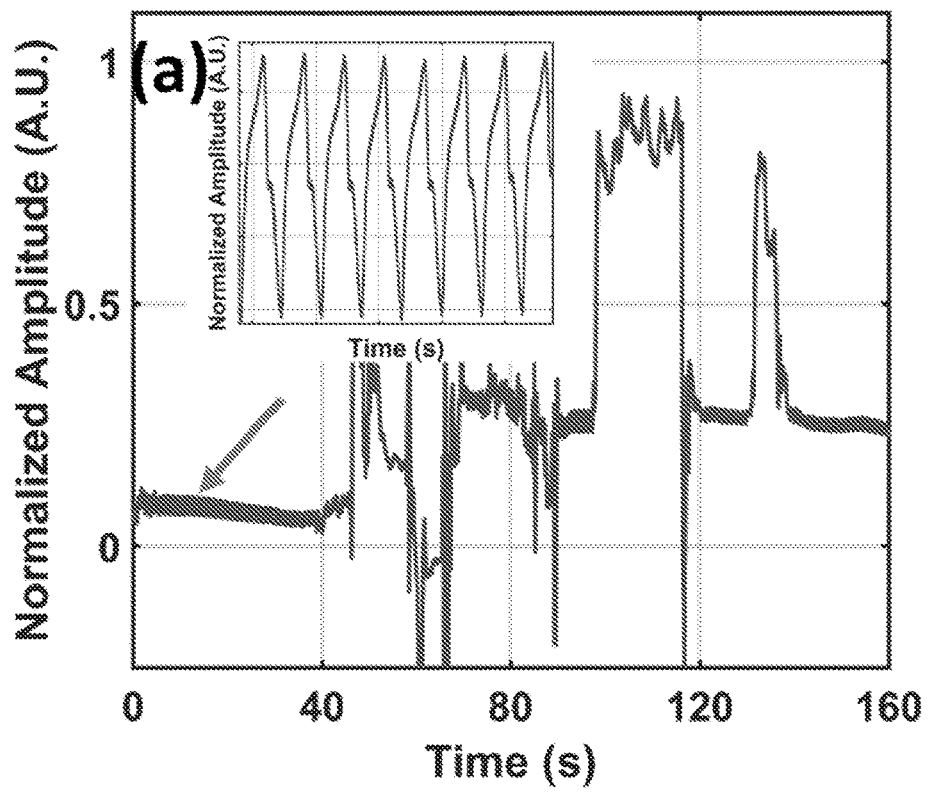
FIGS. 32A-32B. The NCS signal when large body movement starts from 40 s. (A) The amplitude of the NCS signal in time domain. The inset is the demodulated heartbeat waveform in the first 40 s when the person under test sat still. (B) The NCS spectrum during 10-30 s without movement (dark gray), and the NCS spectrum during 85-105 s with large body movement (light gray).
Figure 32B:
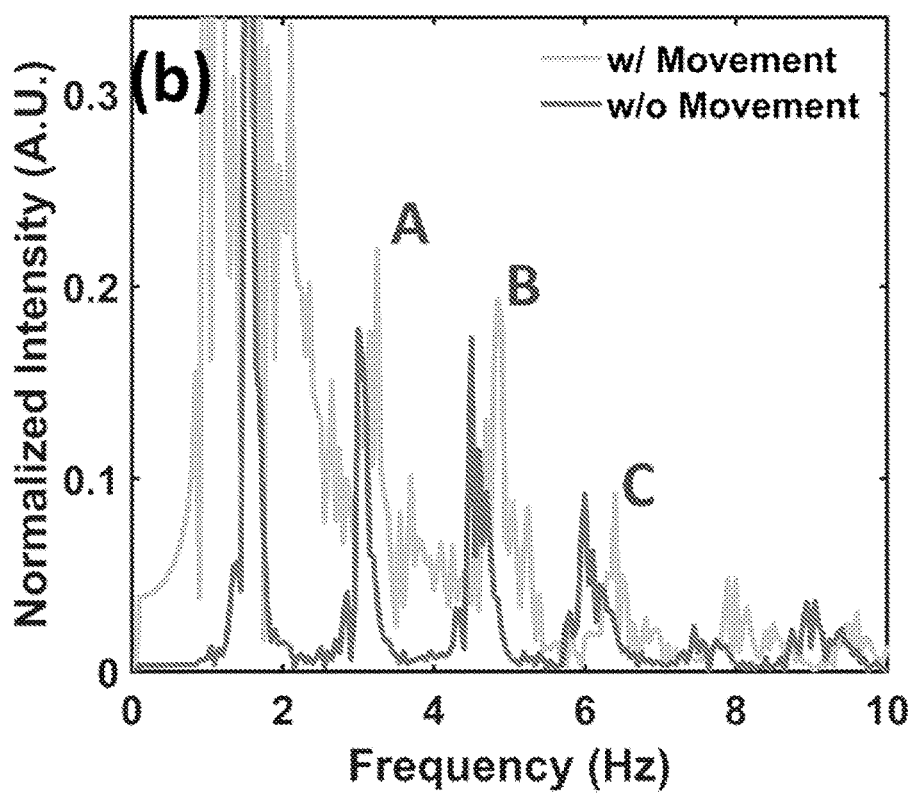

Although NCS can isolate external mechanical movements from internal movements (such as breath from heartbeat and hand motion from wrist pulse), the measurement signal can still be interfered by large body movement when the characteristic spectral components of body motion are close to those of the vital signs. This additional coupling is similar to signal contamination by mixing of amplitude modulation (AM) and frequency modulation (FM), especially when one of the AM and FM sidebands is much larger. The raw NCS measurement signal is shown in FIG. 32A when large motion is included. In the first 40 seconds, the person under test sat still to establish the baseline of clear heartbeat signals for reference, as shown in the inset. During the period between 40 s and 70 s, the person waved their hands vigorously. During the period between 70 s and 100 s, the person moved his body and stood up at the $97^{th}$ second, then continued moving his body left and right. At the $120^{th}$ second, the person resumed the sitting position for 15 s. At around the $135^{th}$ second, the person stood up again until he sat back still at around the $145^{th}$ second. The spectra of 20-second windows with and without movement are shown in FIG. 32B. The spectra are normalized to the intensity of the main peak (without movement) around 1.5 Hz and zoomed in to the lower intensity part. The components below 0.8 Hz and above 15 Hz are filtered out. The light gray curve is the spectrum during the time period from 10 s to 30 s without body movement, and the dark gray curve is during 85-105 s when the heartbeat signal was interfered by large body movement. The spectrum without body movement shows not only the main peak around 1.5 Hz but also the higher frequency harmonics clearly. Body movement often has strong characteristic frequency at lower frequencies. The main spectral peak of the heartbeat is heavily distorted by body movement with signal-to-interference ratio ("SIR") barely above 0 dB. However, the components at higher frequency are less contaminated by body movement. The SIR of peaks A, B, and C are 3.4, 5.9 and 7.6 dB, respectively.

Figure 33A:
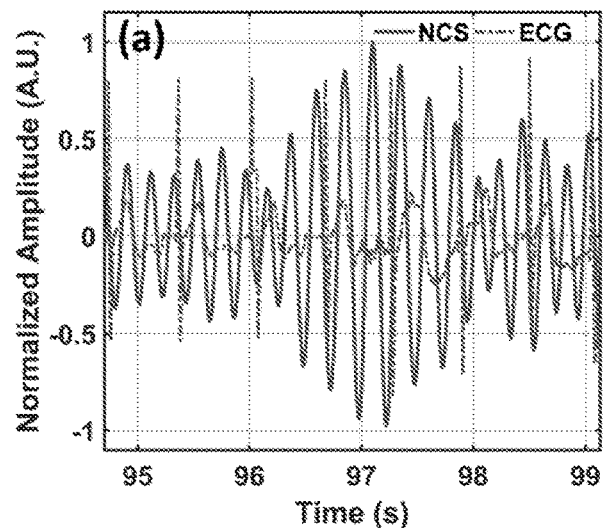
FIGS. 33A-33C. The extracted heartrates. (A) The 3rd harmonic NCS signal (solid line) for heartbeat counting, and the ECG signal for heartbeat reference (dashed line) around 97 s. (B) The heartbeats are counted by NCS (solid line) and ECG (dashed line). The bottom line indicates the error (labeled ERROR). The inset is the results during 25-55 s when large body movement happened after 40 s. (C) The real-time heartrate curve monitored by NCS (solid line) and ECG (dashed line).

Because the high-frequency components of the heartbeat signal have better SIRs, they can be exploited for heartbeat counting with less influence from body movement. The NCS signal passes through a BPF of 4-5.5 Hz to capture the B peak of third harmonics, and is shown in FIG. 33A (the solid line) with the synchronous electrocardiograph (ECG) (the dashed line) during 95-99 s, when the person stood up at the 97th second. The choice of the $3^{rd}$ harmonic is due to its reasonable SIR and large magnitude. The high-frequency components also multiply the heart rate to reduce the counting error. As shown in the first two heartbeats in FIG. 38, there are six maximum and minimum peaks in NCS, so twelve total peaks are used for heart rate estimation. However, during 96-98 s, the person stood up, and the raw NCS signal changed greatly, while the ECG signal with direct gel-pasted skin pad was also distorted, although its QRS feature remains reasonably clear due to its high-frequency characteristics. There are three heartbeats according to the ECG signal, and seventeen peaks from $3^{rd}$ harmonics of NCS. NCS misses one peak, but the error of heartbeat counting is only 5.6% within these three heartbeats and 2.4% for the range in FIG. 33A.

Figure 33B:
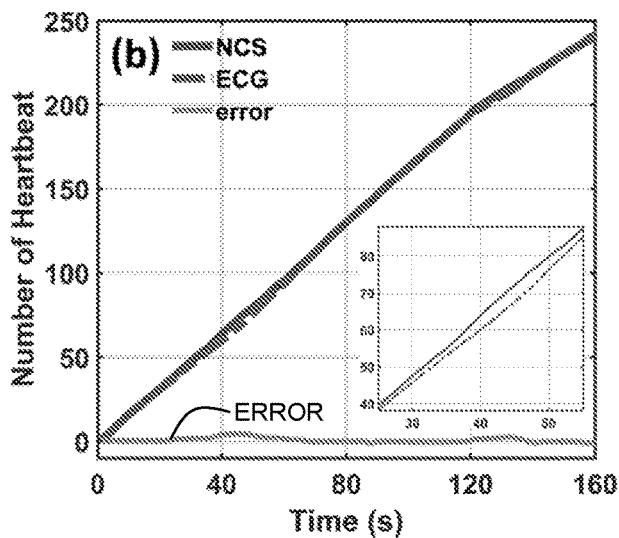
Figure 33C:
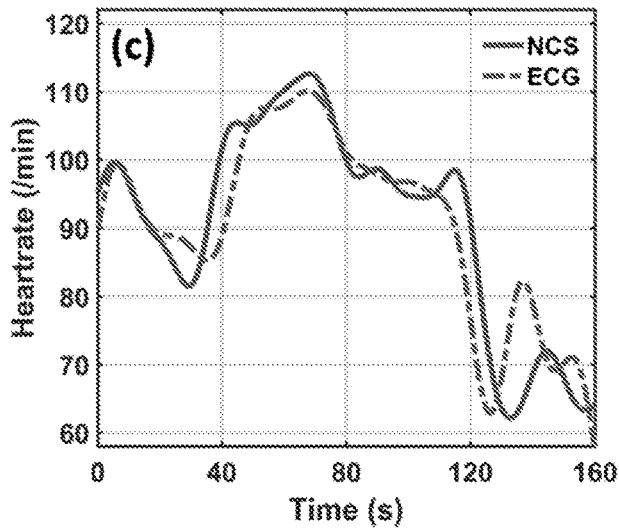

To analyze the real-time heartrate, the heartbeat counting may be evenly resampled at the time domain. The heartbeat counting was based on the number of the maximum and minimum peaks, but the time information of each peak was not evenly distributed as a discrete signal. Hence, the heartbeat data were fitted with cubic spline and evenly distributed with the time resolution of 0.05 s. The heartbeat counting versus time is shown in FIG. 33B. The solid and dashed curves are the NCS and ECG counting results, respectively, and the bottom curve (labeled ERROR) is the error. The maximum error happens after the $40^{th}$ second, when the person was waving the hand. The heartbeat counting curve for this period is shown in the inset of FIG. 33B. After the entire 160 s counting, the result of ECG is 243 (averaged heartrate of 91.1 beats/min), and NCS is 241 (averaged heartrate of 90.4 beats/min). The error is ~0.8%. The heartrate curves monitored by the $3^{rd}$ harmonic of NCS (solid line) and ECG (dashed line) are shown in FIG. 33C. The curves are processed by a low-pass filter of 0.5 Hz. The averaged heartrate and the error based on the peak counting of the $2^{nd}$, $3^{rd}$ and $4^{th}$ harmonics (A, B, C in FIG. 32B) are shown in Table I below. The correlation coefficients are calculated with the heartrate curves obtained by ECG and each harmonic of NCS. The 2nd harmonic of NCS gives the largest error due to the low SIR.

TABLE I

The Heatbeat Analysis Using Different Peaks

| | Heartrate(beat/min) | Error | Correlation |
|---|---|---|---|
| ECG | 91.13 | N/A | N/A |
| NCS $2^{nd}$ | 94.5 | 3.7% | 0.516 |
| NCS $3^{rd}$ | 90.38 | −0.8% | 0.882 |
| NCS $4^{th}$ | 90.75 | −0.4% | 0.822 |

In comparison with other heartbeat de-noising or counting methods, the presently-used extraction method can provide real-time heartrates without calculating the full spectrum that demands a long duration of data to retrieve reasonable frequency resolution. The computational load is small as well, which can be readily performed on the wearable device with a basic microcontroller.

Sleep Scoring

Long-term sleep scoring is very important in the clinical setting to monitor patients' recovery and in the home for both children and adults. In a cost-effective manner, quality of sleep can often be assessed by the upper-body movement together with heartbeat and respiratory monitoring. Instead of the conventional polysomnogram (PSG) which is uncomfortable due to skin contact of sensors and electrodes, this section presents an exemplary sleep monitoring system and method using radio frequency (RF) near-field coherent sensing (NCS) by a single passive RF identification (RFID) tag in the chest area without requiring skin touch, where heart rates, breath rhythm, and motion detection can be synchronously extracted. Motion classification was based on support vector machine (SVM) with semi-supervised learning. Sudden body jerk, tossing, and turning could be recognized correctly in 91.06% of the test cases. The heart rate detection accuracy was also improved after motion artifact correction.

Figure 34:
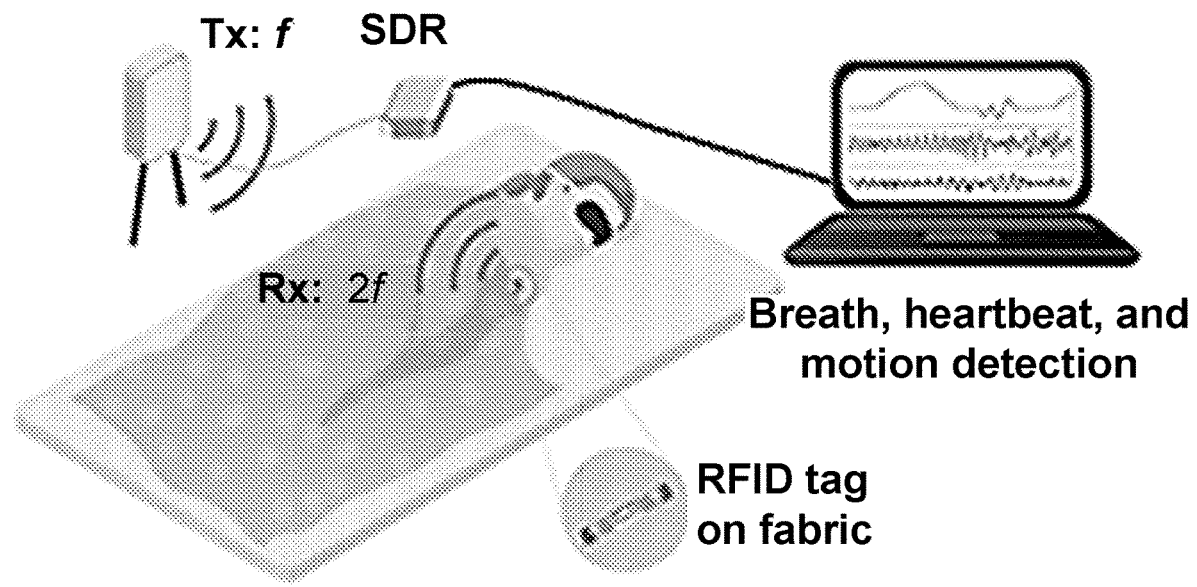
FIG. 34. NCS setup for breath, heartbeat and motion detection. A passive harmonic RFID tag is deployed in the chest area and backscatters harmonic frequency to the reader antenna. Real time demodulation and data analysis are performed on the harmonic reader implemented by SDR.

The present embodiment seeks to have capabilities of simultaneous monitoring of vital signs and body motion for sleep scoring in a low cost and non-intrusive manner, this section presents a sleep scoring system which may be based on the passive UHF RFID system with near-field coherent sensing (NCS), which enhances the RF energy coupling into the body and thus boosts the backscattering signal from heartbeat, breath, and motion on and inside the body. Mechanical movements that result in dynamic dielectric boundary changes can be modulated on the radio signals with unique digital identification (ID), which can be readily extended to monitor multiple tags and persons by a single RFID reader. In some embodiments, the person under study may only wear a single chest tag that can be integrated in the fabric and does not require skin touch or motion constraints, as shown in FIG. 34.

Signal abnormality detection algorithms based on deformation of vital sign waveforms have been developed for motion and other artifact detection in PPG and ECG signals, where temporal and spectral characteristics for classification by SVM, multi-layer perceptron (MLP), decision-tree or other classifiers were employed. The motion detection algorithm is based on detecting changes in NCS waveforms during upper-body movement of tossing, turning, and sudden body jerks. A SVM classifier is trained with signal features at rest only and can detect anomalous features during movement.

Experimental Setup for Sleep Monitoring

NCS can be performed when its antenna is deployed within the near-field zone of the motion source. To evaluate sleep quality, the harmonic RFID tag was placed in the chest area, which was prototyped on a Wireless Identification and Sensing Platform (WISP). The harmonic reader is implemented with National Instrument Ettus Software Defined Radio (SDR) B200. The analog-to-digital and digital-to-analog conversions were carried out at $10^6$ samples per second to retrieve accurate baseband waveforms. The reader transmitter frequency f was at 1 GHz with 10 kHz analog baseband; the corresponding reader receiver frequency was at 2 GHz with 20 kHz baseband.

A controlled data collection was performed simulating the following scenarios during sleep:
1) Stationary state: Subject intentionally remaining still.
2) Torso motion: Slight torso motion for 5 seconds.
3) Body jerk: A fast, high-energy motion of torso and arms for 0.5-2 seconds.
4) Turning: Subject turns to left or right in 1-2 seconds.

Data were collected for 1 hour with the NCS signal sampling rate of 500 samples per second. Simulated movements were performed at intervals of 1 minute. The indoor multi-path effect was negligible as the delay spread was much lower than the NCS sampling time.

Signal Analysis

Figure 35A:
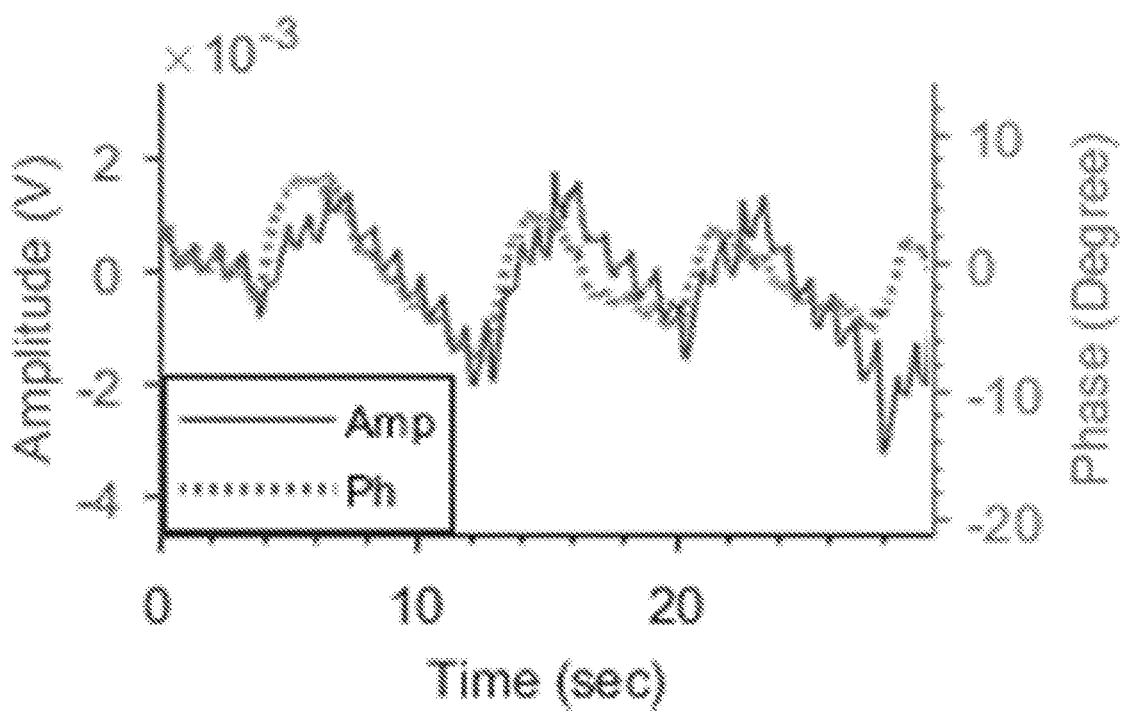
FIG. 35A is a graph of DC-filtered amplitude and phase data.

The surface and internal movements of the body, mainly composed of respiration and heartbeat signals during rest, were modulated on tag backscattering and could be retrieved by signal processing of demodulated digital data. Both amplitude and phase of NCS data capture respiration, heartbeat and motion information with different weightings. Phase was most sensitive to the whole tag motion, while amplitude was less sensitive to small tag motion but was a strong function of the antenna characteristics caused by the near-field coupling to the internal motion. FIG. 35A shows raw DC-filtered amplitude and phase data at rest.

Vital Signs

Figure 35B:
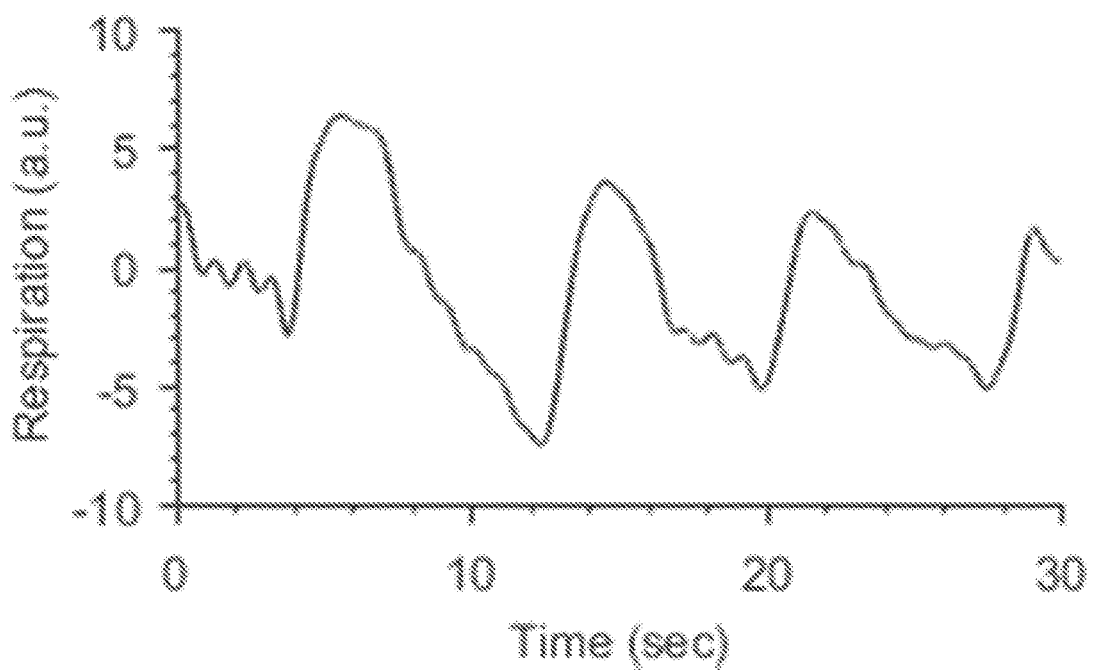
FIG. 35B is a graph showing respiration.
Figure 35C:
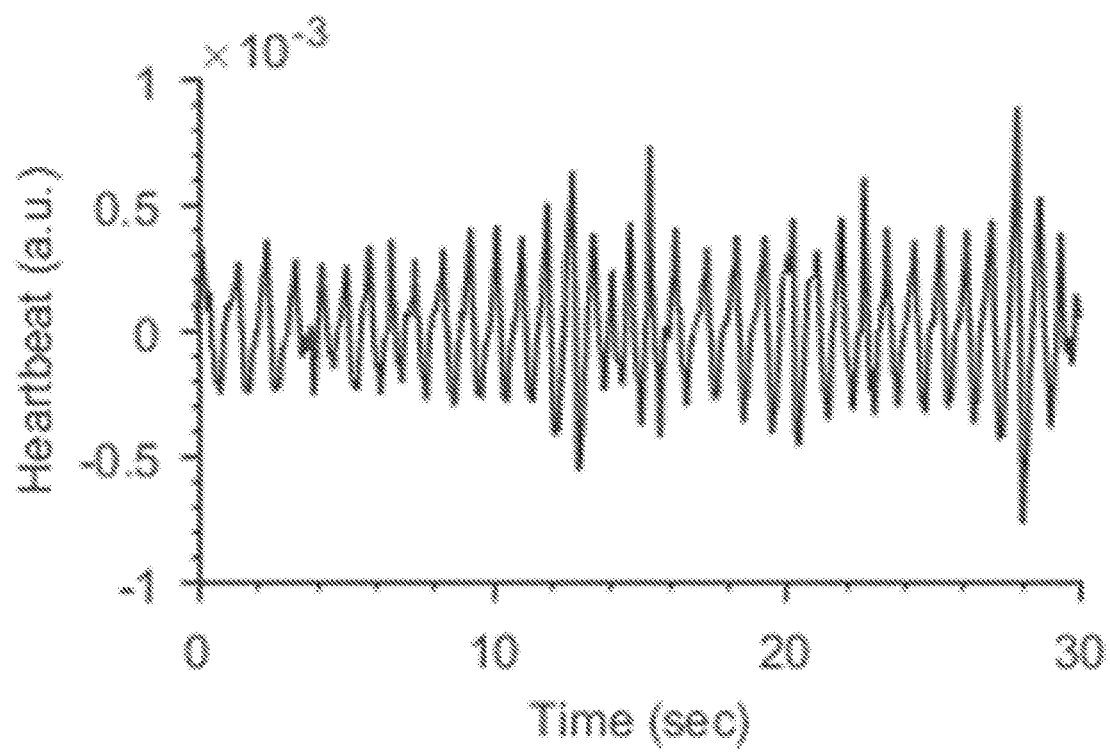
FIG. 35C is a graph showing heartbeat.

Respiration rhythm was clearly extracted from phase by simple filtering. A 20th-order Butterworth filter was used to pass frequencies between 0.01 Hz and 1 Hz in FIG. 35B. Heartbeat was extracted from NCS amplitude by removing frequency below 0.6 Hz containing spontaneous breathing information in FIG. 35C. A linear phase filter was used to remove all spectral content above 10 Hz.

Heartbeat signals can be seriously interfered by the breath signal during the event of shallow panting. Simple filtering can also distort signals in case of obstructive breathing.

Motion Detection

Figure 35D:
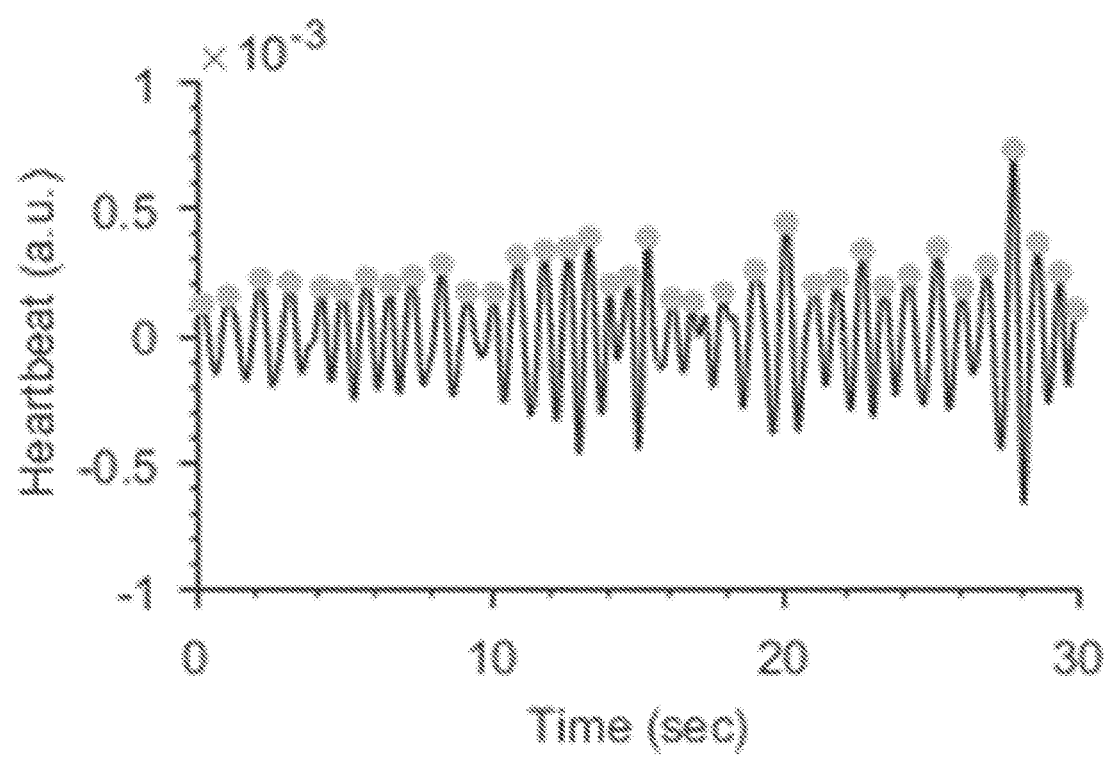
FIG. 35D is a graph of heartbeat showing peak detection.

Motion detection for sleep scoring with accurate heartbeat and respiration information was not directly achieved by simple filtering. Motion affects waveform features of both heartbeat and respiration, though accurate vital signals could be retrieved by correcting motion-affected signals. A beat-by-beat segmentation was performed to achieve finer time resolution of motion. Accurate peak detection is difficult in non-stationary heartbeat waveforms with multiple peaks. The present approach starts from multilevel 1-D wavelet decomposition using Daubechies 10-tap wavelet to identify the coefficient that results in maximum correlation with the heartbeat upon reconstruction. Reconstructed waveforms by the detail coefficient at level 8 (NCS-d8) containing the main component of heartbeat waveform are shown in FIG. 35D. Accurate peak detection could be performed at this stage with additional constraint of minimum peak distance determined by a maximum heart rate of 200 beats per minute.

Motion features were identified based on the difference between motion-affected waveforms and those obtained at rest. Also, features are advantageously robust to account for variation in breath, heartbeat, and signal amplitude over time. Relative beat interval and relative beat root mean square (RMS) are features based on the assumption that beat interval and RMS are not expected to vary significantly from beat to beat. Statistical mean, variance, skewness, and kurtosis are calculated to capture major differences between waveforms at motion and rest, where a heuristic window of five beats is applied. Normalized spectral power in the range of 0.6-10 Hz over the same window was used as another feature motion in addition to the harmonics of heartbeat.

Figure 36:
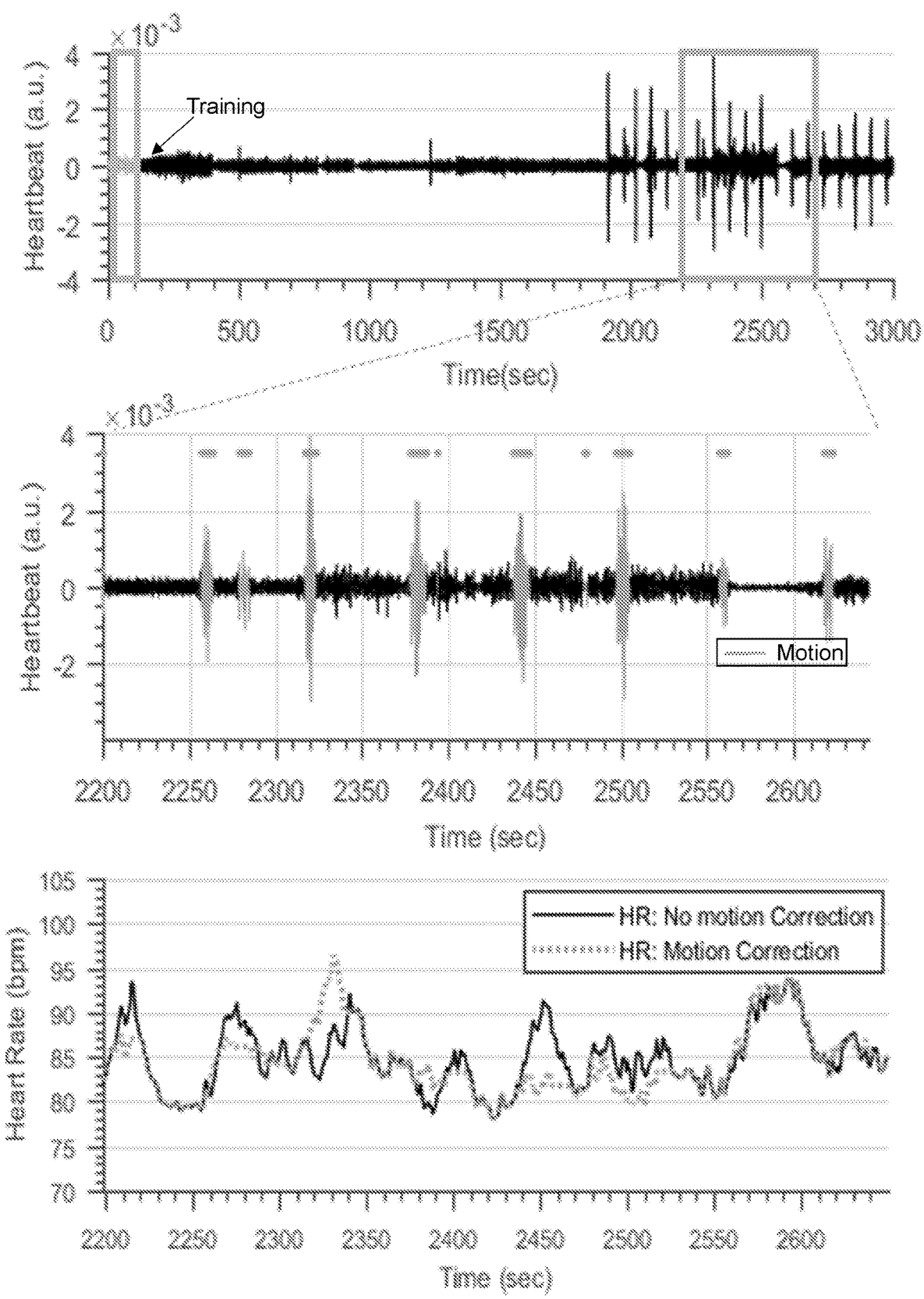
FIGS. 36A-36C are graphs showing heartbeat and corresponding motion detection obtained using NCS.

Motion classification was based on the above seven features. SVM with the radial basis function kernel has been adopted to detect motion. Semi-supervised learning was used for training the model, i.e., training was performed with data collected only at rest with spontaneous breathing. Exclusion of motion data for training reduces the problems of overfitting and generalizing the motion from redundant learning, as well as reduces the inconvenience to perform movement routines during training. FIGS. 36A and 36B show NCS heartbeat and corresponding motion detection. The performance of motion detection algorithm was evaluated by manually annotated results.

False Statistics

Table II shows the numbers of true positive (TP) and false negative (FN) cases for each category of motion. False positive (FP) represents cases when motion is signaled without actual occurrence, which is mainly attributed to irregular breathing pattern and beat detection error. A beat-by-beat motion classification gives accuracy of 97.58%, sensitivity of 88.28%, and specificity of 98.10%. Table III shows the confusion matrix with the number of beats in each category. FIG. 36C shows an example of the improved heart rate estimation after removing motion artifact. The heart rate was estimated with a moving average of 30-beat window length.

TABLE II

Motion Detection Results of the Proposed Algorithm

| Context | Performance Metric | | |
|---|---|---|---|
| | TP | FN | FP |
| Slight Torso Motion | 32 | 3 | 14 |
| Body Jerk | 48 | 1 | |
| Turning | 32 | 7 | |
| Total | 112 | 11 | 14 |

TABLE III

Beat-by-beat Analysis for Accurate Heart Rate

| | | Actual | |
|---|---|---|---|
| | | Motion | Rest |
| Predicted | Motion | 648 | 252 |
| | Rest | 86 | 12985 |

Body jerk motion can be detected with good accuracy, while slow turning can be misclassified as rest. The accuracy can depend on the training data and related algorithm. The experimental embodiment was trained with spontaneous breathing data at rest, including regular breathing with occasional deep breaths. Training with a regular breathing pattern increases the sensitivity to motion, but also results in increased FP in case of irregular breathing.

Small Animal Vital Signs

Current approaches to measuring animal vital signs often involve complicated and invasive preparation procedures and cause major discomfort to the animals under test to the degree that they often need to be anesthetized. For example, electrocardiogram (ECG) for heartbeat waveforms requires body electrodes with good electrical contact, and are therefore difficult to be applied to mammals with thick furs, reptiles with scutes or shells, birds with feathers, and fish with scales. Bare skin areas such as soles and lips often have insufficient electrical signals and can be sensitive to touch. Intramuscular electrodes can usually be performed with anesthetization. Similarly, body surface condition also causes intricacy in photoplethysmography (PPG) setup which limits its application to animals. Auscultation and ultrasound need tight skin touch or impedance-matching gels to obtain clear signals, which require high degrees of animal handling. Radio-frequency (RF) methods based on Doppler far-field backscattering of minute skin motion have non-specific wireless channels and are vulnerable to any ambient motion interference. Respiration is often the dominant signal and becomes a major interference to accurate heartbeat detection. RF methods based on the transmission-line model again require good impedance matching of the skin electrodes. Small animals pose further challenges for most of these previous RF methods due to the limited signal sensitivity.

Figure 37:
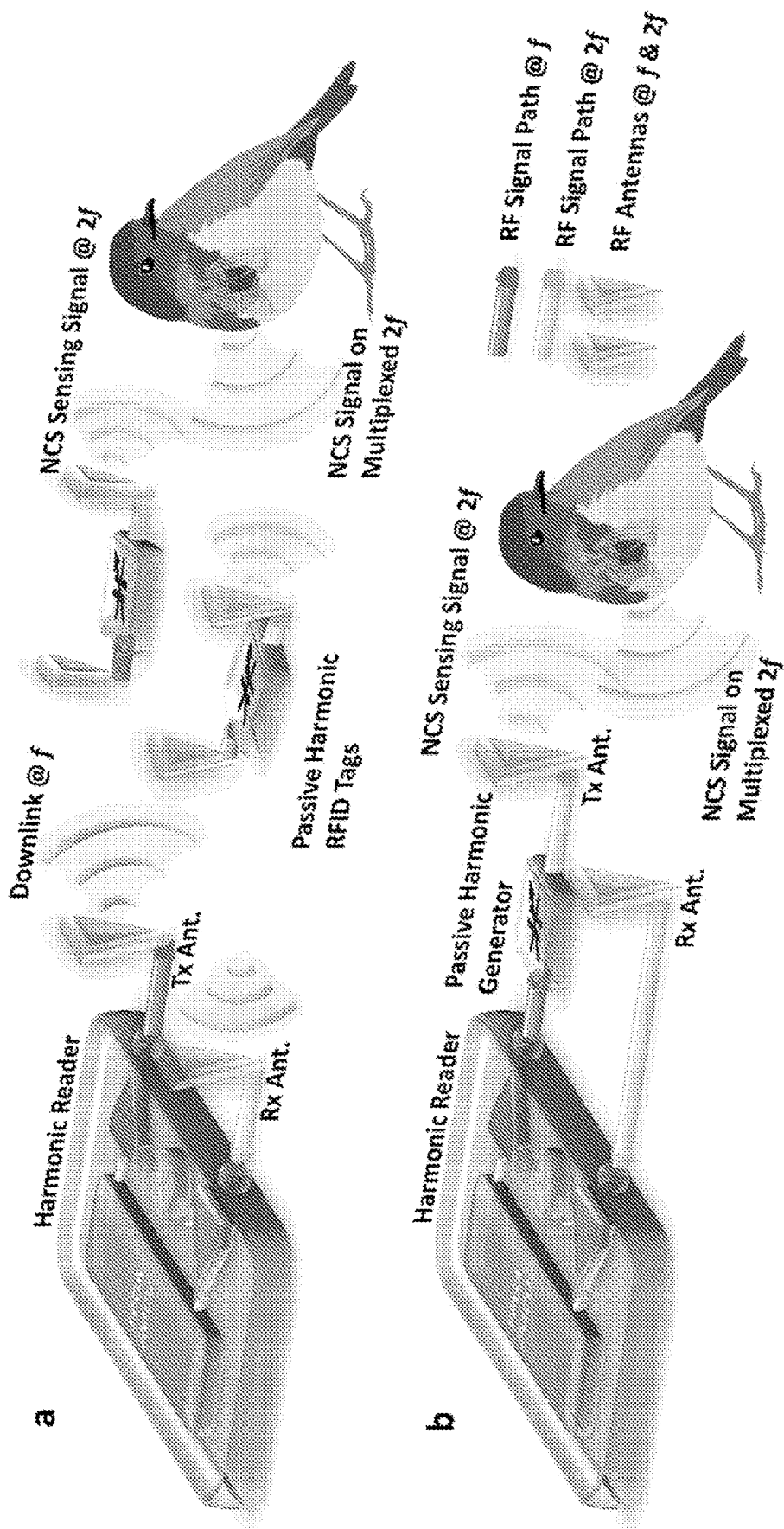
FIGS. 37A-37B. Two setups of near-field coherent sensing (NCS) for vital signs of small conscious animals. The signal is collected by the harmonic reader with digital baseband processing by the field-programmable gate array (FPGA) and microcontroller (MCU). (A) The wireless NCS system is realized by the harmonic RFID system with passive harmonic sensing tags. (B) The wired NCS system replaces the wireless links between the reader and the harmonic tag by RF cables for reduced interference and convenient indoor laboratory deployment.

The present NCS method by near-field modulation of the antenna characteristics on multiplexed radio signals requires no skin touch and offers an effective solution to long-term monitoring of the vital signs for small conscious animals. The schematics for two exemplary NCS setups suitable for use with small animals are shown in FIGS. 37A and 37B. The wireless sensing in FIG. 37A utilizes the harmonic RFID (radio frequency identification) architecture, which makes the passive sensing tag inexpensive and maintenance free, but a specific multiplexing reader is required. This version can be appropriate for deployment in natural habitats with weather-proof passive tags, and the vital signs are collected from a nearby reader on the operator or fixture. The use of the harmonic system reduces self-jamming by separating the bands of the transmitter (Tx) and receiver (Rx), improves the signal sensitivity as well as the signal-to-noise ratio (SNR), and decreases the required strength of the testing RF Tx signal, all of which are advantageous for sensing vital signs of small animals. The NCS signal impinged on the animal body is can be much lower than previous techniques, for example, 0.1 mW/cm$^2$ and 0.15 W/kg to comply to the health and safety standards in the rodent model. In FIG. 37A, the harmonic reader by Ettus X310 Software Defined Radio (SDR) transmits the downlink signal at f around 950 MHz through the reader Tx antenna. The downlink signal powers up the passive harmonic RFID tags and then is converted to the 2nd harmonic frequency at 2f as the NCS sensing signal in the near-field range of the target animal body. As long as the vital signals are within this near-field range (typically about one third of the employed wavelength) of the sensing tag antenna without requiring any skin touch, motion on and inside the animal body can be coupled to the backscattered signal to be received by the reader Rx antenna. The high SNR in NCS allows accurate measurement of minute internal motion such as human wrist pulse waveforms, which is advantageous for vital signs of small animals. The main overall tag antenna motion relative to the reader will be mostly reflected as phase modulation, which can be naturally separated from the magnitude modulation out of the dielectric boundary motion relative to the tag antenna in the near field. The signal originated from the sensing tag can contain a unique identification (ID) code to achieve code-division multiple access, which improves channel isolation against non-specific interference and enables simultaneous reading of multiple sensing tags. Manufacturing of the passive sensing tag is similar to the conventional RFID tag, which gives low-cost production and flexible substrate choices in addition to convenient deployment without need of maintenance.

Alternatively, the setup in FIG. 37B replaces the reader-to-tag channels with RF cables, which reduces interferences and can be appropriate for convenient deployment in an indoor lab with heavy operator traffic or with other interfering sources. The reader Tx antenna transmits the NCS sensing signal directly at 2f and is in the near-field range of the animal under test. Then the NCS signal modulated by the vital signs is received by the reader Rx antenna, which can be deployed according to the application under consideration.

Figure 38A:
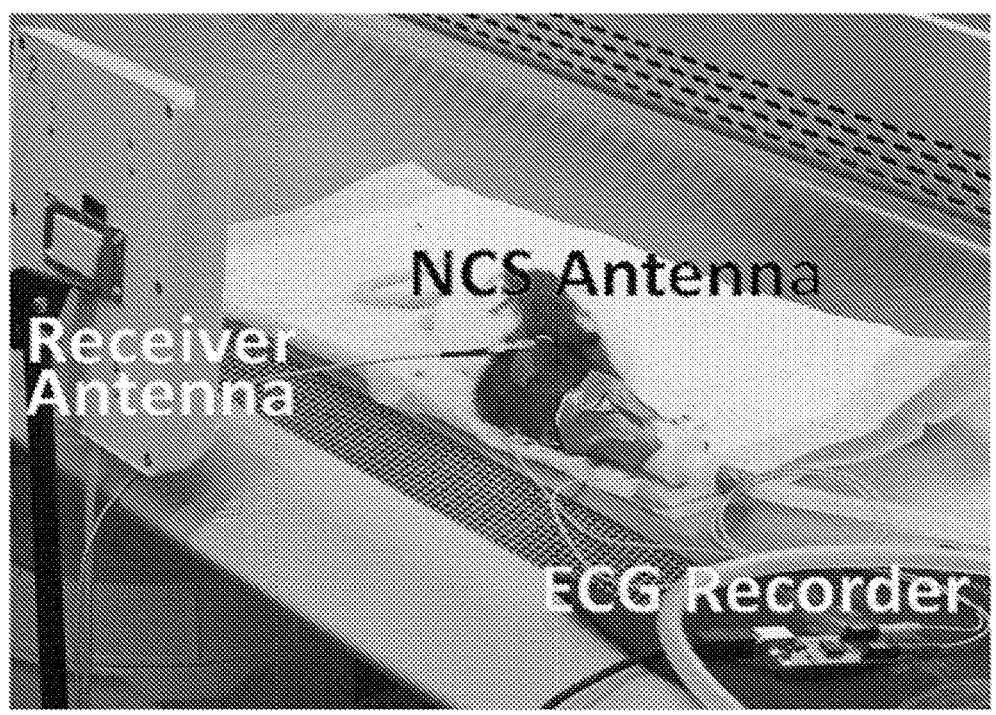
FIG. 38A is a photograph of an experimental setup with an anesthetized rat using synchronous NCS and ECG measurements.
Figure 38B:
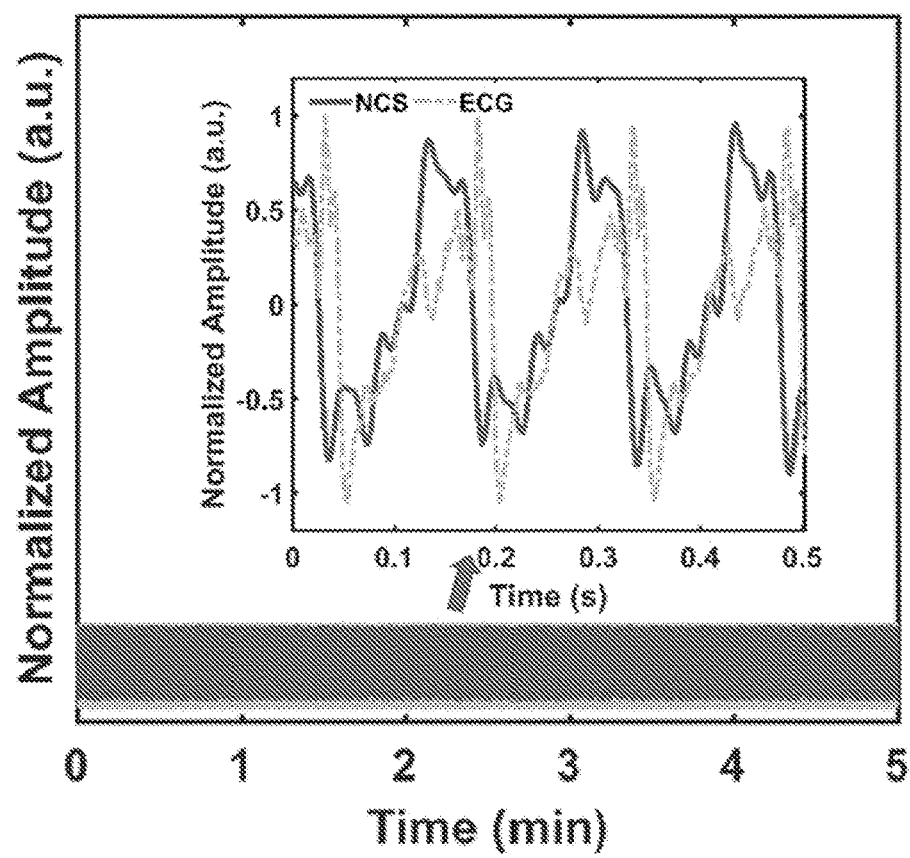
FIG. 38B shows a 5-minute data recording of NCS and ECG from the experimental setup of FIG. 38A. The inset shows waveform details at a selected half-second duration.
Figure 38C:
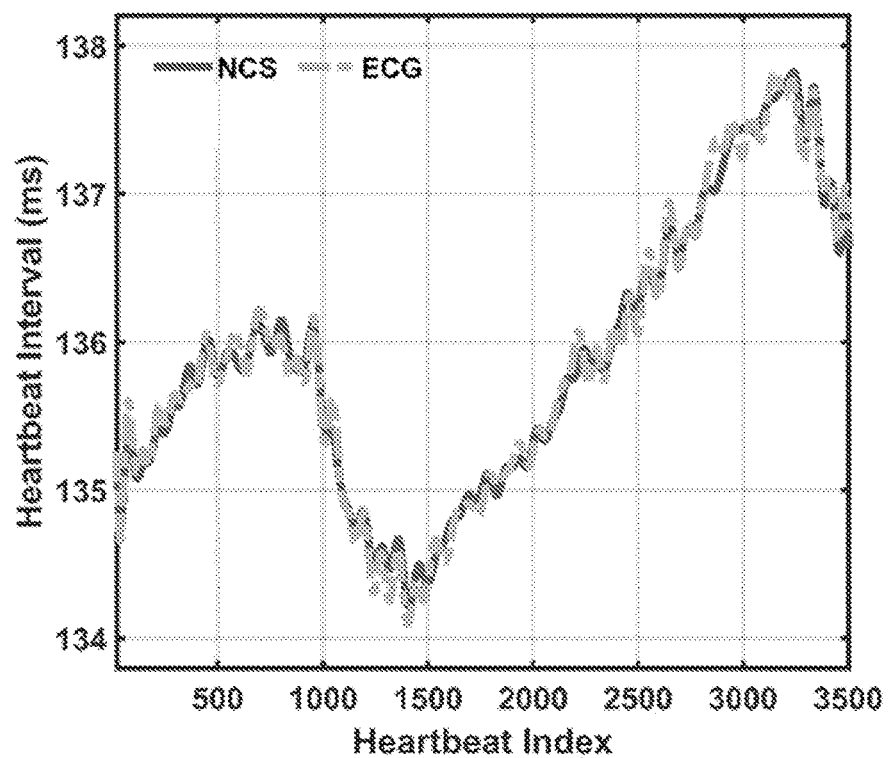
FIG. 38C shows a heartbeat interval extracted from NCS showing a close match to the ECG signal.
Figure 38D:
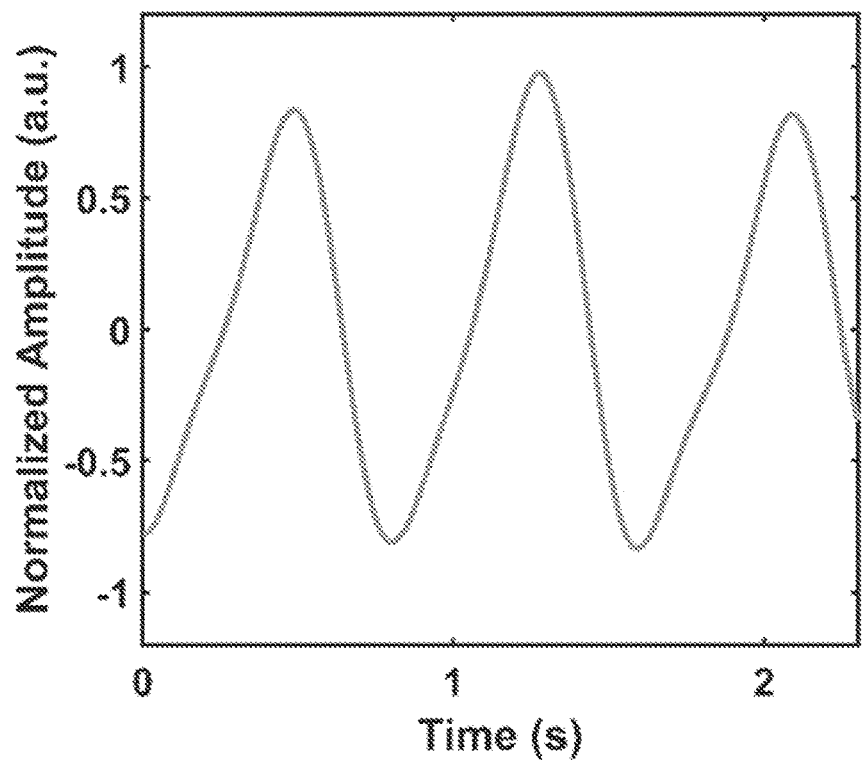
FIG. 38D shows representative respiration signals demodulated from the phase of the NCS signal at approximately the $3^{rd}$ to the $4^{th}$ second.

To compare the NCS vital signals on small animals for cardio waveforms, we first performed synchronized NCS and ECG measurements on a rodent model, which is not only important for clinical trials but also has much fainter and faster heartbeats, providing a more challenging test. A Long-Evans lab rat (*Rattus norvegicus*), coded #110, was anesthetized with complete belly hair removal by razor and Veet Gel cream for ECG electrode deployment, as shown in FIG. 38A. The use of alligator clips and conductive sticker pads on both paws was attempted, but the ECG signal was much weaker and noisier. The sensing tag antenna with the architecture in FIG. 38B was placed near the back of the neck area by a rubber harness without hair removal. Other antenna placements including along the tail, in front of the chest and along the back leg were also attempted with reasonable NCS signals. A representative 5-minute recording is shown in FIG. 38B, and the inset shows the waveform details within half a second within the $3^{rd}$ minute. The cardiogram waveforms of ECG and NCS in FIG. 38B rendered very similar beat-to-beat intervals as shown in FIG. 38C, but the detailed feature timing, for example, position of the NCS features to the timing between the S and T feature points of ECG may need further characterization. From timing comparison, NCS can replace ECG for behavior studies based on heart rate variation (HRV). The breath waveforms were synchronously collected by NCS with an additional 0.5-2.5 Hz low-pass filtering in FIG. 38D, allowing further cardiopulmonary analyses not achievable by ECG alone.

NCS measures the tag antenna characteristics modulated by the near-field geometrical changes, while ECG measures the body potential differences induced by the minute skin current further induced by the electrical heart stimulation and blood flow. In this perspective, NCS has a waveform similar to ballistocardiogram (BCG) and is a more direct measurement of heartbeat motion than ECG. NCS is also much less subject to variations from skin conditions and preparation steps.

Figure 39:
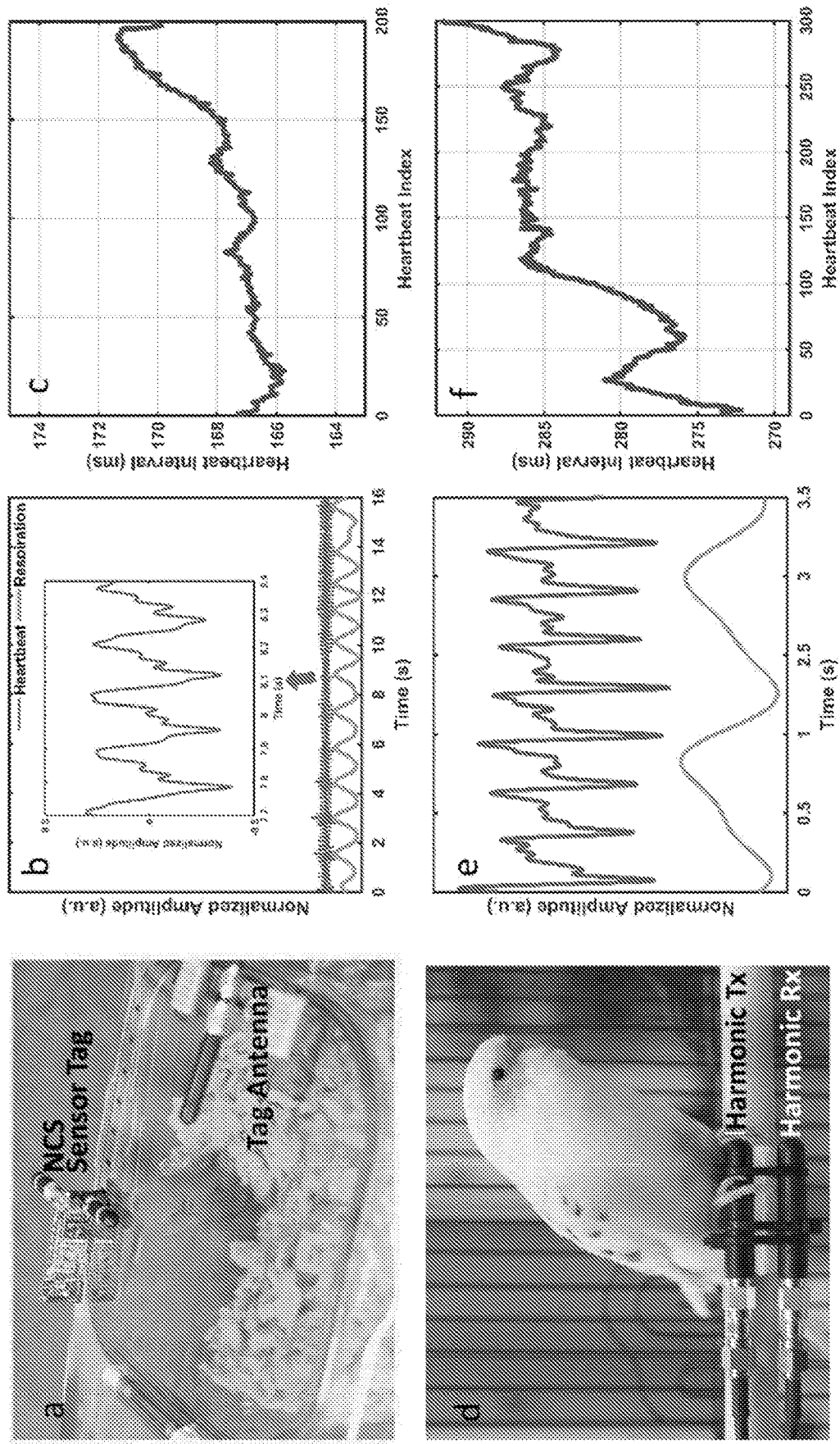
FIGS. 39A-39L show vital-sign monitoring of small conscious animals with non-invasive NCS setups. (A) The experimental setups for the hamster. (B) The heartbeat and respiration signals demodulated from the NCS signal. The inset shows the heartbeat waveform details around the 8th second. (C) The heartbeat interval for about 30 seconds. (D) The wired NCS setup for the parakeet. (E) The heartbeat and respiration signals demodulated from the NCS signal. (F) The extracted heartbeat intervals for about 1.5 minutes. (G) The NCS setup for the Russian tortoise similar to FIG. 39D, where the antennas are under the wood-chip flooring. (H) The normalized raw amplitude of the NCS signal for three minutes, which represents both breaths and heartbeats due to the shell structure. The inset shows the waveform details of the overlapped signals. The light-shaded sections indicate the heartbeats, while the dark-shaded sections the breaths. The strong breath signal will overwhelm the heartbeat signal during the overlap. (I) The on-line processed signals during the same period as (H) by continuous wavelet transform (CWT) show clear separation of heartbeats and breaths for accurate rate estimation. The inset shows the extracted waveform details, clearly indicating every peak in heartbeats and breaths. (J) The NCS setup similar to FIG. 39D for the betta fish. The Tx and Rx antennas are deployed in the water close to the fish. (K) The demodulated NCS phase signal caused by the pectoral fin movement where the inset shows the waveform details. (L) The demodulated NCS magnitude signal possibly caused by the heartbeat.
Figure 39:
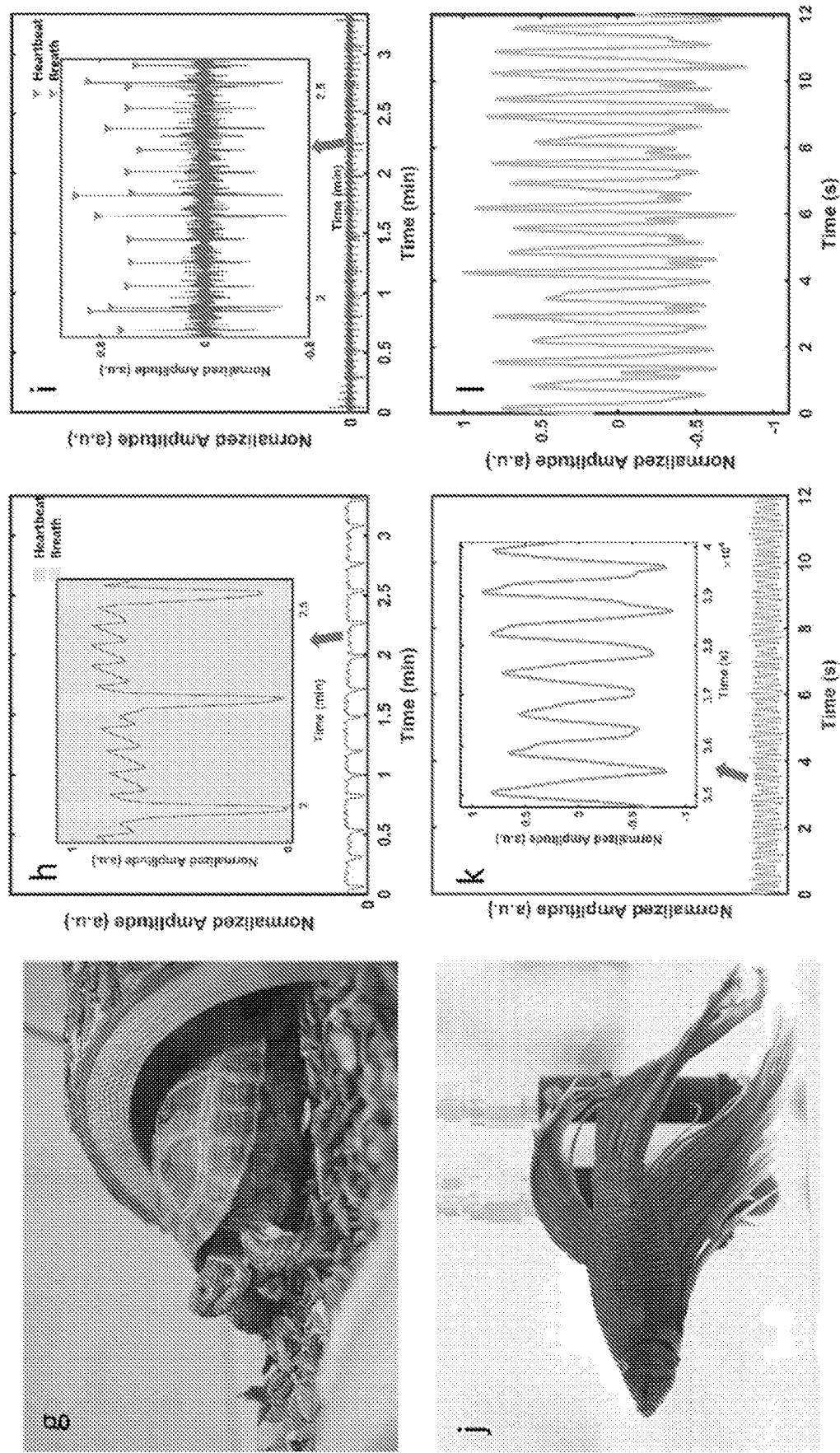

After confirming the cardiopulmonary signals on the anesthetized rat, we next demonstrate the possible noninvasive NCS setups in FIG. 39, which are very difficult, if not impossible, for ECG and other conventional techniques on small conscious animals. A pet golden hamster (Mesocricetus), named "Timo," was monitored in its cage sleeping quarter, as shown in FIG. 39A. Both wireless and wired NCS architectures in FIGS. 37A and 37B were applied outside the cage. For the wireless version, the passive harmonic tag was powered up by the downlink signal, part of which was converted to the $2^{nd}$ harmonic as the NCS sensing signal coupled into the hamster body. The reader Rx antenna was about 1.5 m away from the tag. For the wired version, the sensing antenna was mounted on the right side of the sleeping quarter, which transmits the NCS sensing signal directly. In FIG. 39B, the vital signs of breaths and heartbeats of the hamster were acquired without its notice. The amplitudes of the vital signals are normalized to the maximum values of the entire recording period. The inset shows the heartbeat waveform details around the $8^{th}$ second. The waveform features are similar not only for each heartbeat during the recording, but also to those in the anesthetized rat in FIG. 38B. The negative minimums of the waveform are extracted for the heartbeat interval, as shown in FIG. 39C after applying moving average with the window size of 20. The hamster heartbeat interval is about 20% longer than that of the rat. To demonstrate the NCS applicability to small birds, we measured a pet fancy parakeet (*Melopsittacus undulates*, also known as budgies), named "Banana," as shown in FIGS. 39D-39F. Vital-sign monitoring of conscious birds can enable new capabilities in behavior studies as well as ornithological health screening. FIG. 39D demonstrates the wired experimental setup. The harmonic Tx antenna transmitted the NCS sensing signal, which was coupled into the parakeet body. The harmonic Rx antenna was also integrated to the perch and was able to acquire detailed features of both heartbeat and respiration as shown in FIG. 3E with the extracted heartbeat intervals in FIG. 3F. The antenna deployment is very convenient for the wired NCS setup. After simple observation of the parakeet behavior, we identify, several positions on the perch where the bird usually stood. We chose the most frequent one and mounted the antennas. During the NCS measurement, there was no interference to the circadian rhythm of the pet parakeet.

The next demonstration was made on a pet Russian tortoise (*Agrionemys horsfieldii*, also known as Horsfield's tortoise or Central Asian tortoise), named "Blimp," as shown in FIGS. 39G-39I. Russian tortoises are the first vertebrate species to reach the moon orbits and are important for studies of long space travels due to their sub-hibernation capability, which makes the continuous long-term recording of the vital signs even more scientifically important. Turtles have a body structure of a hard shell and soft body tissues separated by small air gaps. Vital sign acquisition by ECG and ultrasound is only feasible with neck or intramuscular probes, both of which cause major discomfort to the animal. The physiological features of the shell and being ectothermic together with the lack of proper diagnostic methods thus made chelonian critical care very difficult. The hearts of birds and rodents have four chambers with two atria and two ventricles, similar to human, and thus the NCS waveforms in FIGS. 38B, 39B, and 39E have similar features. In comparison, tortoises have a three-chambered heart having two atria and one ventricle, and the NCS cardiogram has different features although the heart rate can still be accurately retrieved. The NCS setup is shown in FIG. 39G. A similar antenna pair in FIG. 39D was placed under the cedar-wood chips outside the glass cage. Due to the body structure, respiration and heartbeat signals are both embedded in the raw data of the NCS amplitude in FIG. 39H because there is no shell surface movement during breath. The signal of the heartbeats can be clear (as shown in the light-shade regions in the inset), but during the respiration period, it would be overwhelmed by the strong breath signal (the dark-shade regions) due to the relatively larger volume of the lungs. To separate the two overlapped signals for accurate rate estimation, the continuous wavelet transform (CWT) was employed to extract the peak features of both waveforms in FIG. 39I. We have also tried the antenna placement directly on the vertebral shell and plastron, where the NCS heartbeat and respiration signals can be clearly recorded as well.

Last but not least, RF signals can work in a short range in water, especially for near-field coupling. Although ECG telemetry is possible, the instrument implant procedure is only suitable for larger fish with a week-long recovery period before unbiased measurements can be performed. Ichthyologists thus have long sought after other non-invasive solutions to retrieve physiological information for behavior studies and evolution biology in small fish. We demonstrated the vital-sign measurements of a pet *Betta splendens* (*B. channoides*, also known as Siamese fighting fish), named "Glee," in FIGS. 39J-39L. The demodulated NCS phase signal is interpreted as pectoral fin movement in FIG. 39K, which has a periodic waveform with frequency confirmed by the unsynchronized video recording. It is believed that the demodulated NCS magnitude signal in FIG. 39L represents the periodical waveform originated from the heartbeat.

Hardware Configuration

As shown in FIGS. 37A and 37B, the harmonic reader was performed by a software defined radio (SDR). We used the combination of Ettus USRP X310 and UBX 160 MHz RF daughterboards. During our experiments, the lower-end Ettus USRP B200/210 could also have been configured as the harmonic reader for this application, but X310 has higher data sampling rates for high resolution of waveform details. To function as a coherent harmonic transceiver in FIGS. 37A and 37B, the Tx chain and the Rx chain share the same RF clock source. The synthesizer in the Rx chain configures the local oscillator (LO) frequency at two times of the LO frequency in the Tx chain. The Tx baseband signal are generated by the field-programmable gate array (FPGA), and the Rx baseband is fed into the FPGA to be demodulated for data recording and display.

Both the wireless and wired versions shown in FIGS. 37A and 37B can be applied for NCS. In the wireless version in FIG. 37A, the passive harmonic tag is designed with the modification of the Wireless Identification and Sensing Platform (WISP) and the nonlinear transmission line (NLTL). The NLTL is the ladder structure of inductors and varactors, so, we use the varactor symbol to represent the harmonic tag and harmonic generator. The harmonic tags operated under harvested RF power can be readily deployed in a large amount on many sensing targets or on multiple-points of the same target. Meanwhile, for single-point monitoring, the wired version in FIG. 37B is easier to apply to indoor animal labs. The harmonic generator here can still be the NLTL as before to provide high conversion efficiency. The low-pass filter at the input port of the NLTL isolates the direct harmonic reflection from NLTL to the reader, and the high-pass filter at the output port of the NLTL damps out the fundamental-frequency signal to the Tx antenna. However, without the tight power constraint as in the passive tag, any active or passive frequency doubler with proper frequency response can replace the NLTL in the wired version. During the experiments, we tried the custom diodes and commercial passive doubler (CRYSTEK CPPD-0.85-2) as the harmonic generator, both of which provide satisfactory performance. The wired NCS system can also be extended for multiple points with the reader CDMA technique, but the system cost will increase proportionally. The benefits of the harmonic system were demonstrated in our pervious works. As a brief summary, the harmonic system provides much better isolation between the Tx and Rx chains, so the Rx noise floor can be much lower to improve both SNR and reader Rx sensitivity. In turn, the Tx power can also be much lower to still maintain the SNR required for the vital signs sensing, which eliminates any further health concern about the RF power impinging to live tissues.

Software Configuration

The SDR is controlled by the computer with the LabVIEW interface. The sampling rates of the DAC (digital to analog converter) and ADC (analog to digital converter) are configured both at 10 MSps. The frequency of the baseband output from the DAC is 1 MHz. When the Tx LO frequency is 950 MHz, the signal output from the Tx is 951 MHz. After the harmonic conversion, the center frequency of the Rx signal will be 1902 MHz. The Rx LO at 1900 MHz is set to be two times of the Tx LO. Hence, the Rx baseband frequency is 2 MHz to be sampled by the ADC. The digitized baseband signal is down converted and down sampled in LabVIEW to the NCS sampling rate of 5 kSps.

Although the present disclosure has been described with respect to one or more particular embodiments, it will be understood that other embodiments of the present disclosure may be made without departing from the spirit and scope of the present disclosure.

What is claimed is:

1. A near-field coherent sensing system for measuring motion of an individual, comprising:
    a first tag comprising a first signal source for generating a first sensing signal using a downlink signal received by the first tag and a first near-field antenna in electrical communication with the first signal source, wherein the first near-field antenna is configured to be disposed within a first near-field coupling range of a first motion to be measured to generate a first measurement signal as the first sensing signal is modulated by the first motion; and
    a receiver for detecting the first measurement signal,
    wherein the first near-field coupling range is less than about one wavelength of the first near-field antenna, and
    wherein a frequency of the first sensing signal generated by the first signal source is a harmonic of a frequency of the downlink signal received by the first tag.

2. The system of claim 1, wherein the first motion a heart motion, a pulse, a respiration motion, a bowel motion, or an eye motion.

3. The system of claim 1, wherein the first sensing signal is an ID-modulated wave, an active radio link, or a backscattering RFID link.

4. The system of claim 1, where the receiver is a part of the first tag.

5. The system of claim 1, wherein the frequency of the first sensing signal is the first harmonic of the frequency of the downlink signal.

6. The system of claim 1, wherein the first tag modulates the downlink signal with an orthogonal ID, such that the first sensing signal is a CDMA signal.

7. The system of claim 1, further comprising a filter in communication with the receiver, wherein the filter is configured to demodulate and filter the first measurement signal to obtain a first motion signal.

8. The system of claim 7, wherein the filter is a processor programmed to sample, demodulate, and filter the first measurement signal to derive motion.

9. The system of claim 1, further comprising:
    a second tag comprising a second signal source for generating a second sensing signal and a second near-field antenna in electrical communication with the second signal source, wherein the second near-field antenna is configured to be disposed within a second near-field coupling range of a second motion to be measured to generate a second measurement signal as the second sensing signal is modulated by the second motion; and wherein the receiver is further configured to detect the second measurement signal, wherein the second near-field coupling range is less than about one wavelength of the second near-field antenna.

10. The system of claim 9, further comprising a processor for measuring a derivative value based on the detected first and second measurement signals.

11. The system of claim 10, wherein the derivative value is a blood pressure.

12. The system of claim 1, wherein the frequency of the first sensing signal is the second harmonic of the frequency of the downlink signal or the third harmonic of the frequency of the downlink signal.

13. The system of claim 1, wherein the first tag is configured to be integrated into a fabric.

14. The system of claim 1, wherein the receiver is configured to isolate a differential mode and a common mode from the first measurement signal and the first sensing signal.

15. The system of claim 1, wherein the first tag is configured to be disposed in water.

16. The system of claim 1, wherein the first near-field antenna comprises (i) a first antenna of the first tag configured to receive the downlink signal from a reader and (ii) a second antenna configured to backscatter an uplink signal to the reader of the first tag.

17. The system of claim 16, wherein the first antenna of the first tag is configured to harvest energy from the downlink signal to provide power to the first tag.

18. The system of claim 17, wherein the first tag further comprises:
  a microcontroller;
  a charge pump configured to harvest a first portion of energy from the downlink signal to operate an RF receiver and the microcontroller; and
  a nonlinear transmission line configured to couple a second portion of energy from the downlink signal for harmonic generation and backscattering through the second antenna of the first tag.

19. The system of claim 16, wherein the first antenna of the first tag and the second antenna of the first tag are mounted to a printed circuit board of the first tag.

20. The system of claim 1, further comprising a reader comprising a far-field antenna, disposed at a far-field distance from the first tag, configured to receive a harmonic signal from the first near-field antenna of the first tag.

* * * * *